US008728738B2

(12) United States Patent
Broet et al.

(10) Patent No.: US 8,728,738 B2
(45) Date of Patent: May 20, 2014

(54) METHOD FOR PREDICTING CLINICAL OUTCOME OF PATIENTS WITH NON-SMALL CELL LUNG CARCINOMA

(75) Inventors: Philippe Broet, Issy les Moulineaux (FR); Sophie Camilleri-Broet, Issy les Moulineaux (FR); Lance Miller, Winston-Salem, NC (US); Patrick Tan, Singapore (SG)

(73) Assignee: Assistance Publique-Hopitaux de Paris, Paris (FR)

( * ) Notice: Subject to any disclaimer, the term of this patent is extended or adjusted under 35 U.S.C. 154(b) by 639 days.

(21) Appl. No.: 13/001,081

(22) PCT Filed: Jul. 2, 2009

(86) PCT No.: PCT/EP2009/058315

§ 371 (c)(1), (2), (4) Date: Jul. 14, 2011

(87) PCT Pub. No.: WO2010/000796

PCT Pub. Date: Jan. 7, 2010

(65) Prior Publication Data

US 2011/0269637 A1 Nov. 3, 2011

Related U.S. Application Data

(60) Provisional application No. 61/077,566, filed on Jul. 2, 2008.

(51) Int. Cl.
*C12Q 1/68* (2006.01)

(52) U.S. Cl.
USPC .......................................... 435/6.14; 424/9.1

(58) Field of Classification Search
None
See application file for complete search history.

(56) References Cited

U.S. PATENT DOCUMENTS

2003/0224509 A1 12/2003 Moon et al.

FOREIGN PATENT DOCUMENTS

WO WO 2007/142936 12/2007

OTHER PUBLICATIONS

Chen, H.-Y. et al. "A Five Gene Signature and Clinical Outcome in Non-Small-Cell Ling Cancer" *The New England Journal of Medicine*, Jan. 4, 2007., pp. 11-20. vol. 356, No. 1, XP-009086044.

Masuya, D. et al. "The *HAUSP* gene plays an important role in non-small cell lung carcinogenesis through p53-dependent pathways" *Journal of Pathology*, 2006, pp. 724-732, vol. 208, XP-008111911.

Miyake, M. et al. "A novel molecular staging protocol for non-small cell lung cancer" *Oncogene*, 1999, pp. 2397-2404, vol. 18, XP-002455553.

Poulsen, T. T. et al. "Characterization of novel therapeutic receptor target candiates for treatment of small cell lung cancer." *Proc. Amer. Assoc. Cancer Res.*, 2004, pp. 1-2, vol. 45, XP-008111757, AACR Meeting Abstracts Online.

"Affymetrix GeneChip Human Genome U133 Array Set HG-U133A", GEO, Mar. 11, 2002, pp. 1-4, XP-002254749.

Jacquot, C. et al. "Effect of Four Genes (ALDH1, NRF1, JAM and KBL) on Proliferation Arrest in a Non-small Cell Bronchopulomonary Cancer Line" *Anticancer Research*, Jul. 2002, pp. 2229-2236, vol. 22, No. 4, XP-008111905.

Written Opinion in International Application No. PCT/EP2009/058315, Sep. 15, 2009, pp. 1-6.

*Primary Examiner* — Jim Ketter

(74) *Attorney, Agent, or Firm* — Saliwanchik, Lloyd & Eisenschenk

(57) ABSTRACT

The invention provides an in vitro method for predicting clinical outcome of a patient affected with a non-small cell lung carcinoma (NSCLC), which method comprises determining the expression level of at least 8 genes in a biological sample of said patient.

12 Claims, 2 Drawing Sheets

Figure 1:
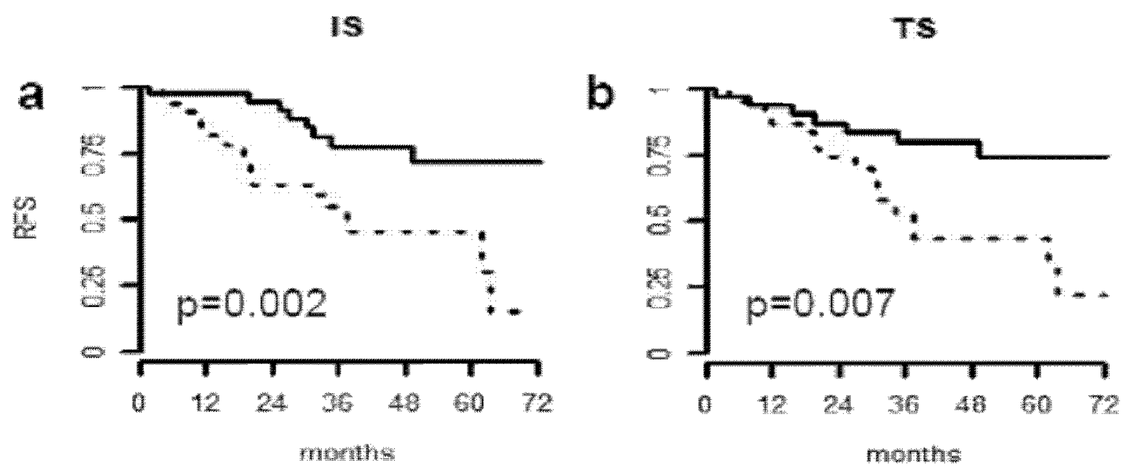

METHOD FOR PREDICTING CLINICAL OUTCOME OF PATIENTS WITH NON-SMALL CELL LUNG CARCINOMA

CROSS-REFERENCE TO RELATED APPLICATION

This application is the U.S. national stage application of International Patent Application No. PCT/EP2009/058315, filed Jul. 2, 2009, which claims the benefit of U.S. Provisional Patent Application No. 61/077,566, filed Jul. 2, 2008, the disclosures of which are hereby incorporated by reference in their entireties, including all figures, tables and amino acid or nucleic acid sequences.

The Sequence Listing for this application is labeled "Seq-List.txt" which was created on Dec. 21, 2010 and is 117 KB. The entire contents of the sequence listing is incorporated herein by reference in its entirety.

The present invention relates to a method for classifying patients affected with non-small cell lung carcinoma (NSCLC), and predicting responsiveness to a chemotherapeutic treatment.

Non-small cell lung carcinoma (NSCLC) is the most common cause of worldwide cancer mortality, with a global five-year survival rate of 15% for all NSCLC cases.

Correct staging of lung cancer is of paramount importance for the treatment planning process. Treatment choices are highly complex even for physicians with much experience in the field and they largely depend on the stage of the disease.

Lung cancer can start in various portions of the lung. From there it spreads in fairly predictable pattern. Typically, close-by lymph nodes are involved first by spreading cancer cells, followed by lymph nodes further away located between the lungs in a space called the mediastinum. In the mediastinum the lung cancer tends to first stay on the side where the original tumor started, once it crosses the midline, it becomes surgically unresectable.

Lung cancer can also spread to distant organs, for example, the liver or adrenal glands, which constitutes the most advanced stage of the disease called stage 1V. The results of staging are summarized in an internationally agreed upon shorthand notation system called the TNM system, where T stands for tumor, N for lymph node an M for distant metastasis (distant spread). Staging information which is obtained prior to surgery, for example by x-rays and endoscopic ultrasound, is called clinical staging and staging by surgery is known as pathological staging.

For patients with NSCLC early stage disease, the survival rate after surgery is 40% to 55% (Mountain et al, 1997; Adebonojo et al 1999; Duque et al 2005), raising the need to accurately identify subgroups who might benefit from additional adjuvant treatment. Adjuvant chemotherapy is currently not favored in stage IA NSCLC (Pignon et al., ASCO Annual Meeting 2006), while patients with stage II tumors routinely receive chemotherapy after resection. The utility of adjuvant chemotherapy for the stage IB tumors, however, remains controversial. Preliminary results of the CALGB 9633 trial suggested a potential survival benefit for adjuvant chemotherapy in Stage IB disease, but updated results from the same trial now show no benefit in overall survival (Strauss et al, ASCO Annual Meeting 2004/2006). One potential explanation for this apparent dilution of beneficial treatment effects over time is that stage IB tumors may actually represent a heterogenous mix of different clinical entities.

A few reports described genomic approaches to discriminate patients with early stage NSCLC. Recently, Potti et al, 2006, combined gene expression information with Bayesian statistics to describe a multi-factorial model for predicting clinical outcome in early stage NSCLC. Chen et al., 2007, also described a simpler 5-gene classifier for the same purchase. Although promising, these previous studies are also not without limitations. First, most of the signatures have been largely inferred by treating NSCLC as a single disease type, while in reality NSCLCs comprise a diverse mix of distinct histological subtypes including adenocarcinoma, squamous carcinoma, and large cell carcinoma, which differ radically in their global gene expression profiles (Garber et al, 2001) Furthermore, there is mounting evidence that different histological subtypes of NSCLC may in fact exhibit different optimal molecular signatures for survival (Raponi et al, 2006). This failure to incorporate histological subtype might reduce model robustness and predictive accuracy in the pure gene expression based models.

One major feature shared by many NSCLCs is chromosomal instability, which can result in the amplification and deletion of either specific genomic regions or even entire chromosomes. Regions exhibiting copy number alterations (CNAs) can affect the expression of cis-localized tumor suppressor genes and oncogenes. However, only few reports, using for most of them low-resolution technologies, have suggested a potential relationship between recurrent CNAs and NSCLC patient prognosis (Balsara et al 2002; Kim et al 2005).

Also, the architecture of CNAs are often complex and consist of multiple "subalterations" with varying degrees of copy number change and not all genes within a CNA region will necessarily show altered gene expression ("copy number driven expression") (Gelsi-Boyer 2005; Pollack et al, 2002). These observations suggest that a substantial proportion of genes within CNAs may be inconsequential for tumor behaviour, and including such genes into a survival model may only add noise and reduce predictive accuracy.

In light of the above, there is still a need for refining clinical staging in order to classify patients with NSCLC, and identify those who would benefit from a chemotherapeutic treatment, vs. those for whom a chemotherapeutic treatment is not recommended, or might even be detrimental.

SUMMARY OF THE INVENTION

The present invention provides a molecular signature for predicting clinical outcome in a patient affected with early stage non-small cell lung carcinoma (NSCLC).

More particularly the invention provides an in vitro method for predicting clinical outcome of a patient affected with a NSCLC, which method comprises determining the expression level of genes, the expression of which is associated with copy number alterations linked with outcome.

The invention provides an in vitro method for predicting clinical outcome of a patient affected with a non-small cell lung carcinoma (NSCLC), which method comprises determining the expression level of at least 8 genes in a biological sample of said patient, wherein said genes are GRM8, NRF1, USP7, PRO0149, TXNL48, GLG1, ZNRF1, and UBE2L3.

Advantageously, overexpression of said genes is indicative of a patient with poor clinical outcome or who would benefit from a chemotherapeutic treatment.

The invention further provides a diagnostic tool for implementing said method, e.g. a DNA chip comprising a solid support which carries nucleic acids that are specific to the cited genes from table A to E, including at least the following genes: GRM8, NRF1, USP7, PRO0149, TXNL48, GLG1, ZNRF1, and UBE2L3.

The combined expression profile of these genes is informative of the status of the patient who, before any chemotherapeutic treatment, can be classified as (i) at very early stage of the disease (e.g. Stage IA or close to Stage IA), and for whom a chemotherapeutic treatment is not recommended, or might even be detrimental, vs (ii) at advanced stage, i.e. exhibiting a poor clinical outcome and who would benefit from a chemotherapeutic treatment.

FIGURE LEGENDS

FIG. 1 shows the internal validation of the lung-cancer gene signatures.

Relapse-free survival (RFS) curves with (1*a*) the integrated genomic-transcriptomic signature (IS) and (1*b*) for the transcriptomic signature (TS) for the optimal feature selection threshold with their corresponding p-values.

Figure 2:
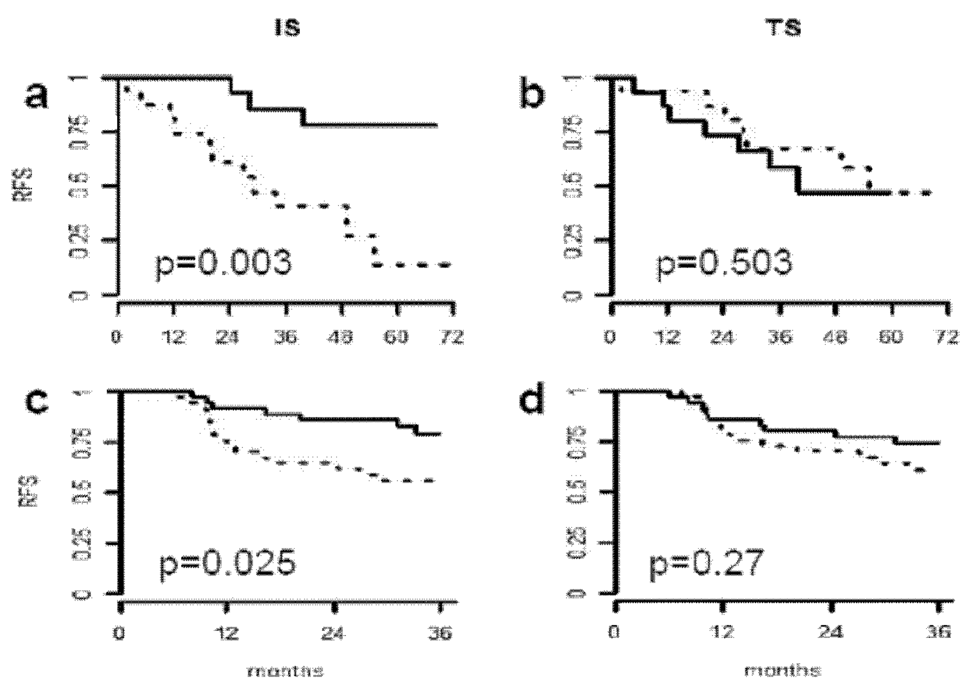

FIG. 2 shows the external validation of the consensus signatures.

External validation of the consensus IS and TS signatures for Duke (2*a*-2*b*) and Michigan series (2*c*-2*d*).

Figure 3:
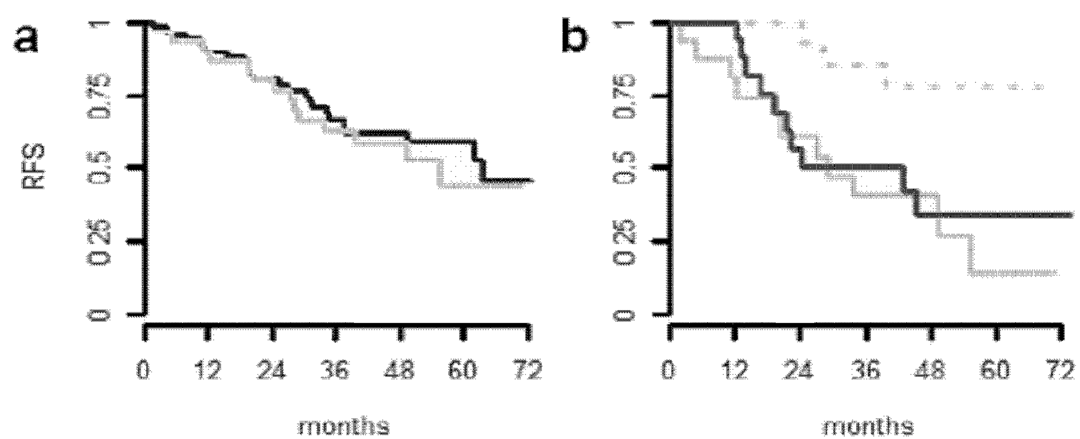

FIG. 3 shows RFS from high-risk group stage I and stage II patients.

(3*a*) RFS curves for our series (dark line) and the stage I adenocarcinoma patients from the Duke series (light grey). (3*b*) High (light grey) and low (dashed line) risk group patients according to the IS for stage I patients from the Duke series with the RFS for stage II patients from the same series (dark line) shown superimposed.

DETAILED DESCRIPTION OF THE INVENTION

The inventors have developed an integrative strategy combining both genomic CNA and transcriptomic copy-number driven expression. They applied this strategy to a cohort of stage IB lung adenocarcinomas profiled using both high-resolution array-CGH and gene expression platforms. They found that an integrated signature was an accurate predictor of relapse-free survival in the original cohort, and also robustly predicted survival in two other independent cohorts.

On this basis, the inventors propose to determine the expression level of the so-identified genes, in order to predict the clinical outcome of patients affected with NSCLC.

Patients

The term "patient" refers to any subject (preferably human) afflicted with a NSCLC. The patient may be a man or a woman.

NSCLC is the most common kind of lung cancer. NSCLCs are grouped together because their prognosis and management are similar, up to now. The three main sub-types defined in the WHO classification (Travis et al, IARC press 2004), i.e. squamous cell lung carcinoma, adenocarcinoma and large cell lung carcinoma, are encompassed in the present invention. Accounting for about a third of lung cancers, squamous cell carcinoma (SCC) comprises 44% of lung cancers in men, and 25% in women. It is defined as a malignant epithelial tumour showing keratinization and/or intercellular bridges that arises from bronchial epithelium. Adenocarcinoma accounts for 28% of cases in men and 42% in women. It usually originates in peripheral lung tissue. Accounting for 9% of lung cancers, large cell carcinoma is by definition undifferentiated non-small cell carcinoma that lacks the cytologic and architectural features of small cell carcinoma and glandular or squamous differentiation.

Lung cancer staging is an assessment of the degree of spread of the cancer from its original source. It is an important factor affecting the prognosis and potential treatment of lung cancer. Non-small cell lung carcinoma is staged from IA ("one A", best prognosis) to IV ("four", worst prognosis) (Mountain et al, 1997). Small cell lung carcinoma is classified as limited stage if it is confined to one half of the chest and within the scope of a single radiotherapy field. Otherwise it is extensive stage (Collins et al, 2007).

In the method of the invention, the patient is preferably affected with a NSCLC (adenocarcinoma, large cell carcinoma or squamous cell carcinoma, preferably with Stage I carcinoma), more particularly with a Stage IA or Stage IB carcinoma.

In practice, the determination of the expression level of said genes, e.g. by a quantitative PCR or microarrays, offers a powerful tool for classifying patients and identifying those who are of worst prognostic and would benefit from a chemotherapeutic treatment.

The method of the invention preferably comprises the step of comparing the combined expression level of said genes with reference values, preferably by using computer tools.

Said "expression level of genes" corresponds to the combined expression profile of said genes, in the targeted population. In the context of determining the quantity of mRNA, the "reference value" is the mean of expression level determined in a whole cohort of NSCLC patients.

In the context of determining the number of gene copies, amplification of the number of gene copies in Chromosome 7 is correlated to a poor clinical outcome ("high risk" patients), whereas deletion of the number of gene copies in Chromosome 16 is correlated with a better clinical outcome.

Clinical Outcome

In the context of the present invention, the term "clinical outcome" refers to the risk of disease's recurrence in the tested patient. More particularly, the present invention allows it to identify "high risk" Stage IB NSCLC patients who would benefit from a chemotherapeutic treatment, similar to Stage II patients. By extension, Stage IB patients designated 'low risk' by the integrated signature might consider not undergoing chemotherapy treatment. The chemotherapy that is herein contemplated is more preferably an adjuvant chemotherapy, i.e. a chemotherapy treatment combined with or set after a surgical intervention.

The Sets of Predictive Genes

All the genes identified are known per se, and listed in the below tables A to E.

Table A presents the set of eight genes whose combined expression profile has been shown to be the most informative with regard to the clinical outcome of the patients; i.e. GRM8, NRF1, USP7, PRO0149, TXNL48, GLG1, ZNRF1, and UBE2L3.

Overexpression of said genes is indicative of a patient with poor clinical outcome or who would benefit from a chemotherapeutic treatment.

In particular, overexpression may reflect an increased number of gene copies.

TABLE A

| subset of 8 genes | | | |
|---|---|---|---|
| Gene | GENBANK access number | Full Name | Seq ID NO: |
| GRM8 | NM_000845 | glutamate receptor, metabotropic 8 | 1 |
| NRF1 | NM_005011 | nuclear respiratory factor 1 | 3 |
| USP7 | NM_003470 | ubiquitin specific peptidase 7 (herpes virus-associated) | 5 |
| PRO0149 | AF090898 | PRO0149 | 7 |
| TXNL4B | NM_017853 | thioredoxin-like 4B | 9 |
| GLG1 | NM_012201 | golgi apparatus protein 1 | 11 |

TABLE A-continued

| subset of 8 genes | | | |
|---|---|---|---|
| Gene | GENBANK access number | Full Name | Seq ID NO: |
| ZNRF1 | NM_032268 | zinc and ring finger 1 | 13 |
| UBE2L3 | NM_003347 | ubiquitin-conjugating enzyme E2L 3 | 15 |

In a particular embodiment, the method of the invention further comprises determining the expression level of the genes of Table B, or of a subcombination thereof (combined with the set of eight genes as defined in Table A):

TABLE B

| Other genes of interest for the predictive method (integrative signature by probe set) | | | | | |
|---|---|---|---|---|---|
| chromosome | Gene | Affymetrix reference | Genbank access Number | Expression (*) | Relevance (**) |
| 7 | PTPRZ1 | 204469_at | NM_002851 | − | −0.0677 |
| 7 | FLJ35834 | 1568924_a_at | — | + | 0.214 |
| 7 | ASB15 | 1564679_at | NM_080928 | + | 0.108 |
| 7 | WASL | 224813_at | NM_003941 | + | 0.448 |
| 7 | WASL | 205809_s_at | NM_003941 | + | 0.584 |
| 7 | WASL | 205810_s_at | NM_003941 | + | 0.515 |
| 7 | WASL | 230340_s_at | NM_003941 | + | 0.449 |
| 7 | — | 227010_at | AL110181 | + | 0.41 |
| 7 | — | 231125_at | — | + | 0.712 |
| 7 | HYAL4 | 220249_at | NM_012269 | + | 0.646 |
| 7 | GPR37 | 214586_at | NM_005302 | + | 0.608 |
| 7 | GPR37 | 209631_s_at | NM_005302 | + | 0.227 |
| 7 | POT1 | 204354_at | NM_015450 | + | 0.768 |
| 7 | POT1 | 204353_s_at | NM_015450 | − | −0.13 |
| 7 | GRM8 | 1556800_a_at | NM_000845 | + | 1.29 |
| 7 | MGC27345 | 231844_at | CR604729 | + | 0.502 |
| 7 | IMPDH1 | 204169_at | NM_000883 | + | 0.737 |
| 7 | IRF5 | 239412_at | NM_002200 | − | −0.0865 |
| 7 | TNPO3 | 212317_at | NM_012470 | + | 0.676 |
| 7 | TNPO3 | 212318_at | NM_012470 | + | 1.03 |
| 7 | TNPO3 | 214550_s_at | NM_012470 | + | 0.81 |
| 7 | MAP2K2 | 202424_at | NM_030662 | + | 0.597 |
| 7 | TSPAN33 | 225775_at | NM_178562 | + | 0.179 |
| 7 | KIAA0828 | 212814_at | NM_015328 | − | −0.0546 |
| 7 | FAM40B | 1555292_at | NM_020704 | + | 0.408 |
| 7 | FAM40B | 231880_at | NM_020704 | + | 0.148 |
| 7 | LOC641819 | 235967_at | — | + | 0.793 |
| 7 | NRF1 | 1570314_at | NM_005011 | − | −0.262 |
| 7 | NRF1 | 211279_at | NM_005011 | + | 1.13 |
| 16 | HBM | 240336_at | NM_001003938 | + | 0.419 |
| 16 | LUC7L | 223295_s_at | NM_201412 | + | 0.54 |
| 16 | ITFG3 | 224749_at | NM_032039 | + | 0.232 |
| 16 | ARHGDIG | 206888_s_at | NM_001176 | + | 0.675 |
| 16 | MRPL28 | 204599_s_at | NM_006428 | + | 0.141 |
| 16 | DECR2 | 219664_s_at | NM_020664 | + | 0.836 |
| 16 | SOLH | 230295_at | NM_005632 | + | 0.485 |
| 16 | C16orf34 | 212109_at | NM_144570 | + | 0.382 |
| 16 | C16orf34 | 212115_at | NM_144570 | + | 0.00292 |
| 16 | NME3 | 204862_s_at | NM_002513 | + | 1.04 |
| 16 | MRPS34 | 218112_at | NM_023936 | + | 0.589 |
| 16 | EME2 | 1569868_s_at | NM_001010865 | + | 0.443 |
| 16 | SPSB3 | 46256_at | NM_080861 | + | 0.468 |
| 16 | NUBP2 | 218227_at | NM_012225 | + | 0.801 |
| 16 | HAGH | 205012_s_at | NM_005326 | + | 0.193 |
| 16 | FAHD1 | 226767_s_at | NM_001018104 | + | 0.568 |
| 16 | FAHD1 | 227960_s_at | NM_001018104 | + | 0.743 |
| 16 | MGC35212 | 237265_at | NM_152764 | + | 0.167 |
| 16 | SEPX1 | 217977_at | NM_016332 | + | 0.0385 |
| 16 | NDUFB10 | 228301_x_at | NM_004548 | + | 0.988 |
| 16 | C16orf68 | 218945_at | NM_024109 | + | 1.54 |
| 16 | ABAT | 206527_at | NM_020686 | − | −0.187 |
| 16 | C16orf51 | 204676_at | NM_015421 | + | 0.632 |
| 16 | PMM2 | 203201_at | NM_000303 | + | 0.867 |
| 16 | CARHSP1 | 224910_at | NM_014316 | + | 0.873 |
| 16 | CARHSP1 | 218384_at | NM_014316 | + | 0.556 |
| 16 | CARHSP1 | 1566135_at | NM_014316 | + | 0.121 |
| 16 | USP7 | 222032_s_at | NM_003470 | + | 0.736 |

TABLE B-continued

| Other genes of interest for the predictive method (integrative signature by probe set) | | | | | |
|---|---|---|---|---|---|
| chromosome | Gene | Affymetrix reference | Genbank access Number | Expression (*) | Relevance (**) |
| 16 | USP7 | 201498_at | NM_003470 | + | 1.62 |
| 16 | USP7 | 201499_s_at | NM_003470 | + | 0.455 |
| 16 | USP7 | 230761_at | NM_003470 | + | 0.62 |
| 16 | — | 236260_at | — | + | 0.647 |
| 16 | — | 1555237_at | — | + | 0.872 |
| 16 | PRO0149 | 225183_at | AF090898 | + | 1.5 |
| 16 | PRO0149 | 238011_at | AF090898 | + | 0.517 |
| 16 | PRO0149 | 217682_at | AF090898 | + | 0.89 |
| 16 | PRO0149 | 225197_at | AF090898 | + | 0.0997 |
| 16 | PRO0149 | 228373_at | AF090898 | + | 0.388 |
| 16 | ATF7IP2 | 219870_at | NM_024997 | − | −0.0374 |
| 16 | EMP2 | 225078_at | NM_001424 | + | 0.00665 |
| 16 | EMP2 | 204975_at | NM_001424 | − | −0.0688 |
| 16 | NUBP1 | 203978_at | NM_002484 | − | −0.11 |
| 16 | CIITA | 210925_at | NM_000246 | + | 0.402 |
| 16 | KIAA0350 | 212786_at | NM_015226 | + | 0.102 |
| 16 | KIAA0350 | 231221_at | NM_015226 | + | 0.901 |
| 16 | PRM1 | 206358_at | NM_002761 | + | 0.348 |
| 16 | MGC24665 | 226456_at | NM_152308 | + | 0.0264 |
| 16 | — | 244889_at | — | + | 0.683 |
| 16 | LITAF | 200704_at | NM_004862 | + | 0.319 |
| 16 | TXNDC11 | 223325_at | NM_015914 | + | 0.125 |
| 16 | GSPT1 | 215438_x_at | NM_002094 | + | 0.693 |
| 16 | LOC440338 | 229978_at | AK000877 | + | 0.0924 |
| 16 | — | 1556619_at | — | − | −0.234 |
| 16 | — | 235215_at | — | + | 0.04 |
| 16 | MKL2 | 1562497_at | NM_014048 | − | −0.0577 |
| 16 | MKL2 | 1558777_at | NM_014048 | + | 0.33 |
| 16 | MKL2 | 218259_at | NM_014048 | + | 0.381 |
| 16 | RRN3 | 222204_s_at | NM_018427 | + | 0.0144 |
| 16 | ZNF19 | 213934_s_at | NM_006961 | + | 0.179 |
| 16 | ZNF19 | 228958_at | NM_006961 | + | 0.611 |
| 16 | ZNF19 | 234953_x_at | NM_006961 | − | −0.401 |
| 16 | CHST4 | 220446_s_at | NM_005769 | + | 0.185 |
| 16 | AP1G1 | 225754_at | AK128078 | + | 0.218 |
| 16 | AP1G1 | 225771_at | AK128078 | − | −0.122 |
| 16 | AP1G1 | 203350_at | AK128078 | + | 0.444 |
| 16 | CA12 | 215867_x_at | NM_001218 | + | 0.197 |
| 16 | LOC146517 | 226095_s_at | AK025339 | − | −0.269 |
| 16 | LOC146517 | 227373_at | AK025339 | + | 0.362 |
| 16 | KIAA0174 | 200851_s_at | NM_014761 | + | 0.073 |
| 16 | — | 1562848_at | — | − | −0.594 |
| 16 | DHODH | 213632_at | NM_001361 | + | 1.1 |
| 16 | HP | 206697_s_at | NM_005143 | + | 0.0181 |
| 16 | HP | 208470_s_at | NM_005143 | − | −0.026 |
| 16 | HPR | 208471_at | NM_020995 | − | −0.048 |
| 16 | TXNL4B | 222748_s_at | NM_017853 | + | 0.84 |
| 16 | TXNL4B | 218794_s_at | NM_017853 | + | 1.16 |
| 16 | DHX38 | 209178_at | NM_014003 | + | 0.233 |
| 16 | — | 226137_at | — | + | 0.222 |
| 16 | ATBF1 | 235785_at | NM_006885 | + | 1.43 |
| 16 | PSMD7 | 201705_at | NM_002811 | + | 0.216 |
| 16 | PSMD7 | 244515_at | NM_002811 | + | 0.273 |
| 16 | — | 228688_at | BC037579 | + | 0.55 |
| 16 | LOC146346 | 225918_at | AL833498 | + | 0.6 |
| 16 | GLG1 | 212045_at | NM_012201 | + | 1.03 |
| 16 | GLG1 | 214730_s_at | NM_012201 | + | 0.253 |
| 16 | GLG1 | 207966_s_at | NM_012201 | + | 1.05 |
| 16 | MLKL | 238025_at | NM_152649 | + | 0.0192 |
| 16 | WDR59 | 218505_at | NM_030581 | − | −0.00777 |
| 16 | ZNRF1 | 223382_s_at | NM_032268 | + | 0.793 |
| 16 | ZNRF1 | 223383_at | NM_032268 | + | 0.408 |
| 16 | ZNRF1 | 225959_s_at | NM_032268 | + | 0.609 |
| 16 | ZNRF1 | 225962_at | NM_032268 | + | 0.318 |
| 16 | ZNRF1 | 231092_s_at | NM_032268 | + | 1.77 |
| 16 | LDHD | 229241_at | NM_194436 | + | 0.478 |
| 16 | ZFP1 | 234810_at | NM_153688 | + | 1.15 |
| 16 | ZFP1 | 226807_at | NM_153688 | + | 0.0997 |
| 16 | BCAR1 | 223116_at | NM_014567 | + | 1.2 |
| 16 | CFDP1 | 203166_at | NM_006324 | + | 0.529 |
| 16 | — | 236588_at | — | + | 0.968 |
| 16 | CFDP1 | 210701_at | NM_006324 | + | 0.121 |
| 16 | LOC124491 | 227586_at | NM_145254 | + | 0.037 |
| 16 | LOC124491 | 228505_s_at | NM_145254 | + | 1.18 |
| 16 | CHST6 | 223786_at | NM_021615 | + | 0.384 |

TABLE B-continued

| Other genes of interest for the predictive method (integrative signature by probe set) | | | | | |
|---|---|---|---|---|---|
| chromosome | Gene | Affymetrix reference | Genbank access Number | Expression (*) | Relevance (**) |
| 16 | COTL1 | 221059_s_at | NM_021149 | + | 0.0675 |
| 16 | CHST5 | 219182_at | NM_024533 | + | 0.174 |
| 16 | CHST5 | 64900_at | NM_024533 | + | 0.193 |
| 16 | GABARAPL2 | 209046_s_at | NM_007285 | – | –0.174 |
| 16 | ADAT1 | 219384_s_at | NM_012091 | – | –0.211 |
| 16 | KARS | 200840_at | NM_005548 | + | 1.21 |
| 16 | KARS | 200079_s_at | NM_005548 | + | 0.058 |
| 16 | TERF2IP | 201174_s_at | NM_018975 | + | 0.216 |
| 16 | RPL18 | 200022_at | NM_000979 | – | –0.4 |
| 16 | MAF | 206363_at | NM_005360 | + | 0.138 |
| 16 | MAF | 209348_s_at | NM_005360 | + | 0.172 |
| 16 | — | 229327_s_at | — | + | 0.3 |
| 20 | — | 230294_at | — | + | 0.0492 |
| 20 | RALY | 201271_s_at | NM_016732 | + | 0.268 |
| 22 | DGCR5 | 215244_at | NR_002733 | + | 0.216 |
| 22 | DGCR5 | 1558118_at | NR_002733 | + | 0.708 |
| 22 | DGCR9 | 215003_at | DQ581778 | + | 0.693 |
| 22 | DGCR5 | 1563243_at | — | – | –0.165 |
| 22 | DGCR2 | 214198_s_at | NM_005137 | + | 0.637 |
| 22 | DGCR2 | 227028_s_at | NM_005137 | + | 0.415 |
| 22 | DGCR11 | 215725_at | L77561 | – | –0.68 |
| 22 | DGCR12 | 1566235_at | — | + | 0.0214 |
| 22 | — | 217275_at | — | + | 0.346 |
| 22 | DGCR13 | 217285_at | — | + | 0.269 |
| 22 | DGCR14 | 32029_at | NM_022719 | + | 0.45 |
| 22 | DGCR14 | 204383_at | NM_022719 | + | 0.285 |
| 22 | DGCR14 | 216285_at | NM_022719 | + | 0.833 |
| 22 | CLTCL1 | 205944_s_at | NM_007098 | + | 0.566 |
| 22 | MRPL40 | 203152_at | NM_003776 | + | 0.503 |
| 22 | HIRA | 227086_at | NM_003325 | + | 0.868 |
| 22 | DKFZp434N035 | 223628_at | NM_032262 | + | 0.456 |
| 22 | HIC2 | 1559600_at | NM_015094 | + | 0.0363 |
| 22 | HIC2 | 212964_at | NM_015094 | + | 0.361 |
| 22 | HIC2 | 212965_at | NM_015094 | + | 0.671 |
| 22 | HIC2 | 212966_at | NM_015094 | + | 0.173 |
| 22 | UBE2L3 | 200682_s_at | NM_003347 | + | 0.0359 |
| 22 | UBE2L3 | 200683_s_at | NM_003347 | + | 0.0732 |
| 22 | UBE2L3 | 200684_s_at | NM_003347 | + | 0.782 |
| 22 | UBE2L3 | 200676_s_at | NM_003347 | + | 0.238 |

(*) (-) means that underexpression of the gene is correlated with a poor clinical outcome and identifies patients who would benefit from a chemotherapeutic treatment
(+) means that overexpression of the gene is correlated with a poor clinical outcome and 5 identifies patients who would benefit from a chemotherapeutic treatment
(**) relevance (or weight) is calculated as described in the below example.

Tables C-E: Subgroups of Genes of Interest for the Predictive Method

TABLE C

| Integrative signature (by gene) | | | |
|---|---|---|---|
| chromosome | Gene | Affymetrix reference | Expression * |
| 7 | PTPRZ1 | 204469_at | – |
| 7 | FLJ35834 | 1568924_a_at | + |
| 7 | ASB15 | 1564679_at | + |
| 7 | WASL | 224813_at;205809_s_at;205810_s_at; | + |
| 7 | HYAL4 | 220249_at | + |
| 7 | GPR37 | 214586_at;209631_s_at | + |
| 7 | POT1 | 204354_at;204353_s_at | + |
| 7 | GRM8 | 1556800_a_at | + |
| 7 | MGC27345 | 231844_at | + |
| 7 | IMPDH1 | 204169_at | + |
| 7 | IRF5 | 239412_at | – |
| 7 | TNPO3 | 212317_at;212318_at;214550_s_at | + |
| 7 | MAP2K2 | 202424_at | + |
| 7 | TSPAN33 | 225775_at | + |
| 7 | KIAA0828 | 212814_at | – |
| 7 | FAM40B | 1555292_at;231880_at | + |
| 7 | LOC641819 | 235967_at | + |
| 7 | NRF1 | 1570314_at;211279_at | – |
| 16 | HBM | 240336_at | + |

TABLE C-continued

| Integrative signature (by gene) | | | |
|---|---|---|---|
| chromosome | Gene | Affymetrix reference | Expression * |
| 16 | LUC7L | 223295_s_at | + |
| 16 | ITFG3 | 224749_at | + |
| 16 | ARHGDIG | 206888_s_at | + |
| 16 | MRPL28 | 204599_s_at | + |
| 16 | DECR2 | 219664_s_at | + |
| 16 | SOLH | 230295_at | + |
| 16 | C16orf34 | 212109_at;212115_at | + |
| 16 | NME3 | 204862_s_at | + |
| 16 | MRPS34 | 218112_at | + |
| 16 | EME2 | 1569868_s_at | + |
| 16 | SPSB3 | 46256_at | + |
| 16 | NUBP2 | 218227_at | + |
| 16 | HAGH | 205012_s_at | + |
| 16 | FAHD1 | 226767_s_at;227960_s_at | + |
| 16 | MGC35212 | 237265_at | + |
| 16 | SEPX1 | 217977_at | + |
| 16 | NDUFB10 | 228301_x_at | + |
| 16 | C16orf68 | 218945_at | + |
| 16 | ABAT | 206527_at | − |
| 16 | C16orf51 | 204676_at | + |
| 16 | PMM2 | 203201_at | + |
| 16 | CARHSP1 | 224910_at;218384_at;1566135_at | + |
| 16 | USP7 | 222032_s_at;201498_at;201499_s_at;230761_at | + |
| 16 | PRO0149 | 225183_at;238011_at;217682_at;225197_at;228373_at | + |
| 16 | ATF7IP2 | 219870_at | − |
| 16 | EMP2 | 225078_at;204975_at | + |
| 16 | NUBP1 | 203978_at | − |
| 16 | CIITA | 210925_at | + |
| 16 | KIAA0350 | 212786_at;231221_at | + |
| 16 | PRM1 | 206358_at | + |
| 16 | MGC24665 | 226456_at | + |
| 16 | LITAF | 200704_at | + |
| 16 | TXNDC11 | 223325_at | + |
| 16 | GSPT1 | 215438_x_at | + |
| 16 | LOC440338 | 229978_at | + |
| 16 | MKL2 | 1562497_at;_1558777_at;218259_at | − |
| 16 | RRN3 | 222204_s_at | + |
| 16 | ZNF19 | 213934_s_at;228958_at;234953_x_at | + |
| 16 | CHST4 | 220446_s_at | + |
| 16 | AP1G1 | 225754_at;225771_at;203350_at | + |
| 16 | CA12 | 215867_x_at | + |
| 16 | LOC146517 | 226095_s_at;227373_at | − |
| 16 | KIAA0174 | 200851_s_at | + |
| 16 | DHODH | 213632_at | + |
| 16 | HP | 206697_s_at;208470_s_at | + |
| 16 | HPR | 208471_at | − |
| 16 | TXNL4B | 222748_s_at;218794_s_at | + |
| 16 | DHX38 | 209178_at | + |
| 16 | ATBF1 | 235785_at | + |
| 16 | PSMD7 | 201705_at;244515_at | + |
| 16 | LOC146346 | 225918_at | + |
| 16 | GLG1 | 212045_at;214730_s_at;207966_s_at | + |
| 16 | MLKL | 238025_at | + |
| 16 | WDR59 | 218505_at | − |
| 16 | ZNRF1 | 223382_s_at;223383_at;225959_s_at;225962_at;231092_s_at | + |
| 16 | LDHD | 229241_at | + |
| 16 | ZFP1 | 234810_at;226807_at | + |
| 16 | BCAR1 | 223116_at | + |
| 16 | CFDP1 | 203166_at;210701_at | + |
| 16 | LOC124491 | 227586_at;228505_s_at | + |
| 16 | CHST6 | 223786_at | + |
| 16 | COTL1 | 221059_s_at | + |
| 16 | CHST5 | 219182_at;64900_at | + |
| 16 | GABARAPL2 | 209046_s_at | − |
| 16 | ADAT1 | 219384_s_at | − |
| 16 | KARS | 200840_at;200079_s_at | + |
| 16 | TERF2IP | 201174_s_at | + |
| 16 | RPL18 | 200022_at | − |
| 16 | MAF | 206363_at;209348_s_at | + |
| 20 | RALY | 201271_s_at | + |
| 22 | DGCR5 | 215244_at;1558118_at;1563243_at; | + |
| 22 | DGCR9 | 215003_at; | + |
| 22 | DGCR2 | 214198_s_at;227028_s_at | + |
| 22 | DGCR11 | 215725_at | − |
| 22 | DGCR12 | 1566235_at | + |
| 22 | DGCR13 | 217285_at | + |

TABLE C-continued

| Integrative signature (by gene) | | | |
|---|---|---|---|
| chromosome | Gene | Affymetrix reference | Expression * |
| 22 | DGCR14 | 32029_at;204383_at;216285_at | + |
| 22 | CLTCL1 | 205944_s_at | + |
| 22 | MRPL40 | 203152_at | + |
| 22 | HIRA | 227086_at | + |
| 22 | DKFZp434N035 | 223628_at | + |
| 22 | HIC2 | 1559600_at;212964_at;212965_at;212966_at | + |
| 22 | UBE2L3 | 200682_s_at;200683_s_at;200684_s_at;200676_s_at | + |

* (−) means that underexpression of the gene is correlated with a poor clinical outcome and identifies patients who would benefit from a chemotherapeutic treatment
(+) means that overexpression of the gene is correlated with a poor clinical outcome and identifies patients who would benefit from a chemotherapeutic treatment

TABLE D

| subgroup with relevance >0.5 | | |
|---|---|---|
| chromosome | Gene | Expression * |
| 7 | WASL | + |
| 7 | HYAL4 | + |
| 7 | GPR37 | + |
| 7 | POT1 | + |
| 7 | GRM8 | + |
| 7 | MGC27345 | + |
| 7 | IMPDH1 | + |
| 7 | TNPO3 | + |
| 7 | MAP2K2 | + |
| 7 | LOC641819 | + |
| 7 | NRF1 | + |
| 16 | LUC7L | + |
| 16 | ARHGDIG | + |
| 16 | DECR2 | + |
| 16 | NME3 | + |
| 16 | MRPS34 | + |
| 16 | NUBP2 | + |
| 16 | FAHD1 | + |
| 16 | MGC35212 | + |
| 16 | NDUFB10 | + |
| 16 | C16orf68 | + |
| 16 | C16orf51 | + |
| 16 | PMM2 | + |
| 16 | CARHSP1 | + |
| 16 | USP7 | + |
| 16 | PRO0149 | + |
| 16 | KIAA0350 | + |
| 16 | GSPT1 | + |
| 16 | ZNF19 | + |
| 16 | DHODH | + |
| 16 | TXNL4B | + |
| 16 | ATBF1 | + |
| 16 | LOC146346 | + |
| 16 | GLG1 | + |
| 16 | ZNRF1 | + |
| 16 | ZFP1 | + |
| 16 | BCAR1 | + |
| 16 | CFDP1 | + |
| 16 | LOC124491 | + |
| 16 | KARS | + |
| 22 | DGCR5 | + |
| 22 | DGCR9 | + |
| 22 | DGCR2 | + |
| 22 | DGCR14 | + |
| 22 | CLTCL1 | + |
| 22 | MRPL40 | + |
| 22 | HIRA | + |
| 22 | HIC2 | + |
| 22 | UBE2L3 | + |

* (−) means that underexpression of the gene is correlated with a poor clinical outcome and identifies patients who would benefit from a chemotherapeutic treatment
(+) means that overexpression of the gene is correlated with a poor clinical outcome and identifies patients who would benefit from a chemotherapeutic treatment

TABLE E

| subgroup of genes with relevance >1 | | |
|---|---|---|
| chromosome | Gene | Expression * |
| 7 | GRM8 | + |
| 7 | NRF1 | + |
| 16 | NME3 | + |
| 16 | C16orf68 | + |
| 16 | USP7 | + |
| 16 | PRO0149 | + |
| 16 | DHODH | + |
| 16 | TXNL4B | + |
| 16 | ATBF1 | + |
| 16 | GLG1 | + |
| 16 | ZNRF1 | + |
| 16 | ZFP1 | + |
| 16 | BCAR1 | + |
| 16 | LOC124491 | + |
| 16 | KARS | + |
| 22 | UBE2L3 | + |

* (−) means that underexpression of the gene is correlated with a poor clinical outcome and identifies patients who would benefit from a chemotherapeutic treatment
(+) means that overexpression of the gene is correlated with a poor clinical outcome and identifies patients who would benefit from a chemotherapeutic treatment

Determination of Expression Level

Determination of the expression level of a gene can be performed by a variety of techniques, from a biological sample. The term "biological sample" means any biological sample derived from a patient, preferably a sample which contains nucleic acids. Examples of such samples include fluids, tissues, cell samples, organs, biopsies, etc. Most preferred samples are tumor samples. Blood, plasma, saliva, urine, seminal fluid, etc, may also be used. The biological sample may be treated prior to its use, e.g. in order to render nucleic acids available. Techniques of cell or protein lysis, concentration or dilution of nucleic acids, are known by the skilled person.

Generally, the expression level as determined is a relative expression level.

More preferably, the determination comprises contacting the sample with selective reagents such as probes, primers or ligands, and thereby detecting the presence, or measuring the amount, of polypeptide or nucleic acids of interest originally in the sample. Contacting may be performed in any suitable device, such as a plate, microtiter dish, test tube, well, glass, column, and so forth In specific embodiments, the contacting is performed on a substrate coated with the reagent, such as a nucleic acid array or a specific ligand array. The substrate may be a solid or semi-solid substrate such as any suitable support comprising glass, plastic, nylon, paper, metal, polymers and the like. The substrate may be of various forms and sizes, such as a slide, a membrane, a bead, a column, a gel, etc. The contacting may be made under any condition suitable for a detectable complex, such as a nucleic acid hybrid or an antibody-antigen complex, to be formed between the reagent and the nucleic acids or polypeptides of the sample.

In a particular embodiment, the expression level may be determined by determining the quantity of mRNA.

Methods for determining the quantity of mRNA are well known in the art. For example the nucleic acid contained in the samples (e.g., cell or tissue prepared from the patient) is first extracted according to standard methods, for example using lytic enzymes or chemical solutions or extracted by nucleic-acid-binding resins following the manufacturer's instructions. The extracted mRNA is then detected by hybridization (e.g., Northern blot analysis) and/or amplification (e.g., RT-PCR). Preferably quantitative or semi-quantitative RT-PCR is preferred. Real-time quantitative or semi-quantitative RT-PCR is particularly advantageous.

Other methods of Amplification include ligase chain reaction (LCR), transcription-mediated amplification (TMA), strand displacement amplification (SDA) and nucleic acid sequence based amplification (NASBA).

Nucleic acids having at least 10 nucleotides and exhibiting sequence complementarity or homology to the mRNA of interest herein find utility as hybridization probes or amplification primers. It is understood that such nucleic acids need not be identical, but are typically at least about 80% identical to the homologous region of comparable size, more preferably 85% identical and even more preferably 90-95% identical. In certain embodiments, it will be advantageous to use nucleic acids in combination with appropriate means, such as a detectable label, for detecting hybridization. A wide variety of appropriate indicators are known in the art including, fluorescent, radioactive, enzymatic or other ligands (e.g. avidin/biotin).

Probes typically comprise single-stranded nucleic acids of between 10 to 1000 nucleotides in length, for instance of between 10 and 800, more preferably of between 15 and 700, typically of between 20 and 500. Primers typically are shorter single-stranded nucleic acids, of between 10 to 25 nucleotides in length, designed to perfectly or almost perfectly match a nucleic acid of interest, to be amplified. The probes and primers are "specific" to the nucleic acids they hybridize to, i.e. they preferably hybridize under high stringency hybridization conditions (corresponding to the highest melting temperature Tm, e.g., 50 (Y0 formamide, 5× or 6×SCC. SCC is a 0.15 M NaCl, 0.015 M Na-citrate).

The nucleic acid primers or probes used herein may be assembled as a kit. Such a kit includes consensus primers and molecular probes. A preferred kit also includes the components necessary to determine if amplification has occurred. The kit may also include, for example, PCR buffers and enzymes; positive control sequences, reaction control primers; and instructions for amplifying and detecting the specific sequences.

In another embodiment, the expression level is determined by DNA chip analysis. Such DNA chip or nucleic acid microarray consists of different nucleic acid probes that are chemically attached to a substrate, which can be a microchip, a glass slide or a microsphere-sized bead. A microchip may be constituted of polymers, plastics, resins, polysaccharides, silica or silica-based materials, carbon, metals, inorganic glasses, or nitrocellulose. Probes comprise nucleic acids such as cDNAs or oligonucleotides that may be about 10 to about 60 base pairs. To determine the expression level, a sample from a test subject, optionally first subjected to a reverse transcription, is labelled and contacted with the microarray in hybridization conditions, leading to the formation of complexes between target nucleic acids that are complementary to probe sequences attached to the microarray surface. The labelled hybridized complexes are then detected and can be quantified or semi-quantified. Labelling may be achieved by various methods, e.g. by using radioactive or fluorescent labelling. Many variants of the microarray hybridization technology are available to the man skilled in the art.

In a particular embodiment, the expression level is determined by determining the number of copies of the genes.

Comparative genomic hybridization (CGH) was developed to survey DNA copy-number variations across a whole genome. With CGH, differentially labelled test and reference genomic DNAs are co-hybridized to normal metaphase chromosomes, and fluorescence ratios along the length of chromosomes provide a cytogenetic representation of DNA copy-number variation. Array-based CGH, in which fluorescence ratios at arrayed DNA elements provide a locus-by-locus measure of DNA copy-number variation, represents another means of achieving increased mapping resolution.

A cDNA microarray-based CGH method is described e.g. in Pollack et al, 1999.

In a particular embodiment, the invention provides an in vitro method for predicting clinical outcome of a patient affected with a Stage I non-small cell lung adenocarcinoma, which method comprises determining the number of gene copies of at least 8 genes in a biological sample of said patient, wherein said genes are GRM8, NRF1, USP7, PRO0149, TXNL48, GLG1, ZNRF1, and UBE2L3.

In this context, the invention further provides a DNA chip comprising a solid support which carries nucleic acids that are specific to GRM8, NRF1, USP7, PRO0149, TXNL48, GLG1, ZNRF1, and UBE2L3 genes.

Chips which further carries nucleic acids that are specific to any or all of the genes listed in any of Tables B, C, D, E, or a subcombination thereof, are also useful in the present invention.

Other methods for determining the expression level of said genes include the determination of the quantity of proteins encoded by said genes.

Such methods comprise contacting a biological sample with a binding partner capable of selectively interacting with a marker protein present in the sample. The binding partner is generally an antibody, that may be polyclonal or monoclonal, preferably monoclonal.

The presence of the protein can be detected using standard electrophoretic and immunodiagnostic techniques, including immunoassays such as competition, direct reaction, or sandwich type assays. Such assays include, but are not limited to, Western blots; agglutination tests; enzyme-labeled and mediated immunoassays, such as ELISAs; biotin/avidin type assays; radioimmunoassays; immunoelectrophoresis; immunoprecipitation, etc. Also, the protein expression may be detected by immunohistochemistry on tissue section of the tumor sample (e.g. frozen or formalin-fixed paraffin embedded material). The reactions generally include revealing labels such as fluorescent, chemiluminescent, radioactive, enzymatic labels or dye molecules, or other methods for detecting the formation of a complex between the antigen and the antibody or antibodies reacted therewith.

The aforementioned assays generally involve separation of unbound protein in a liquid phase from a solid phase support to which antigen-antibody complexes are bound. Solid supports which can be used in the practice of the invention include substrates such as nitrocellulose (e.g., in membrane or microtiter well form); polyvinylchloride (e.g., sheets or microtiter wells); polystyrene latex (e.g., beads or microtiter plates); polyvinylidine fluoride; diazotized paper; nylon membranes; activated beads, magnetically responsive beads, and the like.

More particularly, an ELISA method can be used, wherein the wells of a microtiter plate are coated with an antibody against the protein to be tested. A biological sample containing or suspected of containing the marker protein is then added to the coated wells. After a period of incubation sufficient to allow the formation of antibody-antigen complexes, the plate(s) can be washed to remove unbound moieties and a detectably labeled secondary binding molecule added. The secondary binding molecule is allowed to react with any captured sample marker protein, the plate washed and the presence of the secondary binding molecule detected using methods well known in the art.

The example illustrates the invention without limiting its scope.

Example

Prediction of Clinical Outcome in Multiple Lung Cancer Cohorts By Integrative Genomics: Implications for Chemotherapy Selection

METHODS

Patients and Tumor Samples

This study was based on a series of 85 consecutive chemotherapy-naive patients who underwent surgery at the Hôtel-Dieu Hospital (AP-HP, France) between August 2000 and February 2004 for stage IB (pT2N0) primary adenocarcinoma or large cell lung carcinoma of peripheral location. For all cases, pathological slides were reviewed without any information regarding the outcome. Following clinical and pathological parameters were collected: age, sex, tobacco exposure, type of resection, laterality, necrosis, size of the tumor (as measured in macroscopy), histological subtype, differentiation (well, moderate, poor), vessel invasion, visceral pleura involvement; TTF-1 expression. Patients with bronchioloalveolar adenocarcinomas or large cell neuroendocrine carcinomas were excluded from this study. The quality of frozen tissue was checked by cytological apposition on microscopic glass slide, followed by May Gruñwald Giemsa staining; only tissue samples with tumor content >50% were selected. This study was approved by institutional ethics committees.

Array-based comparative genomic hybridization (aCGH) and gene expression microarrays were both performed.

DNA was extracted from frozen samples using the Nucleon DNA extraction kit (BACC2, Amersham Biosciences, Buckinghamshire, UK), according to the manufacturer's procedures. Briefly, frozen tumor sections were cut into small pieces and digested in proteinase K overnight at 42° C. Deproteinisation was carried out in 5M sodium perchlorate followed by extraction in Chloroform/Alcohol isomamylique. After centrifugation, the upper phase was precipitated in cold Alcohol 100. DNA pellets were dried and re-suspended in tris-EDTA. For each tumor, two micrograms of tumor and reference genomic DNAs (unrelated male DNA) were directly labeled with Cy3-dCTP or Cy5-dCTP respectively and hybridized onto CGH microarrays containing 32,000 DOP-PCR amplified Bacterial Artificial Chromosome (BAC) genomic clones providing tiling coverage of the human genome (spotted on two arrays). Hybridizations were performed using a MAUI hybridization station, and after washing, the slides were scanned on a GenePix 4000B scanner, as described previously (Ishkanian et al, 2002).

Total RNA was extracted from frozen (−80° C.) tumor samples using a standard Trizol procedure. Frozen samples were shattered in liquid nitrogen and homogenized in 1 ml TRIzol (Invitrogen, Carlsbad, USA). Extraction was performed using a standard chloroform/isopropanol method. RNA pellets were resuspended in RNase-free water, subjected to a Qiagen clean up step and stored at −80° C. For gene expression analyses, the Human U133Plus 2.0 oligonucleotide arrays (Affymetrix, Santa Clara, Calif.) containing a total of 47,000 transcripts with 61,000 probe sets were used, according to the manufacturer's protocol. In this study, RNA from 74 samples out of the 85 tumors was of sufficient quality to enable reliable gene expression analysis. The array datasets have been deposited in NCB's Gene Expression Omnibus (GEO, http://www.ncbi.nlm.nih.gov/geo/) and are accessible through GEO Series accession number GSE10445.

Preprocessing of the Array Data

The aCGH signal intensities were normalized using a two-channel microarray normalization procedure (Yang et al, 2002) implemented in Genedata Expressionist Pro software (Basel, Switzerland). BAC genomic clones mapping to sex chromosomes (X and Y) were not considered for the analysis. Inferences about the gain/loss/modal status of each BAC clone for each sample was obtained using the CGHmix classification procedure (Broët et al, 2006) which computes the posterior probabilities of a clone belonging to either of three defined genomic states (loss, modal/unaltered and gain copy state). The inventors assigned each clone to one of two modified copy-number allocation states (loss or gain copy state) if its corresponding posterior probability was above a defined threshold value, otherwise the clone was assigned to the modal/unaltered copy state. This latter threshold value was selected to obtain a similar FDR of 5% for each sample, where false discovery here corresponded to a clone incorrectly defined as amplified or deleted by our allocation rule. Clones with an absolute fluorescence intensity log ratio of higher than 0.5 and a posterior probability of being amplified greater than 70% were defined as high-level amplifications/deletions.

The expression microarray data were standardized and normalized using the robust multi-array average (RMA) procedure (Irizarry et al, 2003). Genes whose maximum expression did not exceed the median value of expression or whose interquartile range (IQR) did not exceed the first quartile of the IQR distribution were excluded. A total of 37,771 probe sets were considered for analysis.

Defining Patterns of Copy Number Alterations (CNAs)

To analyze the propensity of each genomic region (defined by a BAC clone) to be deleted or amplified across a homogeneous group of tumor samples, the inventors modeled the distribution of the number of observed deletions, modal (unaltered loci) and amplifications for all the genomic regions using a latent class model relying on a finite mixture of multinomial distributions (McLchlan et al, 2000). Here, the inventors considered a latent class model with three (low, intermediate, high) levels for both amplification and deletion representing in total nine (32) chromosomal patterns. Each of these nine chromosomal patterns describes the joint propensity of a given genomic region for being deleted/unmodified/amplified. From our series, the inventors estimated for each genomic region its posterior probabilities for each of the nine chromosomal patterns using Monte Carlo Markov chain techniques. Then, a classification rule was applied which assigned each genomic region to the chromosomal pattern to which it had the highest probability of belonging. From the nine chromosomal patterns, the one corresponding to the highest frequency for amplification and lowest for deletion was defined as an "exclusively amplified" recurrent CNA, and vice versa ("exclusively deleted" recurrent CNA).

Statistical Analysis to Identify Copy-Number-Driven Genes

To identify copy-number-driven genes, each probe set was assigned to the nearest mapped BAC clone. For each probe set, a classical linear regression model was applied where gene expression was the dependent variable and DNA copy number change was the explanatory variable (coded as −1, 0, 1 for loss, modal and gain, respectively). From the resulting test statistics, we calculated the posterior probability of relationship between genomic and transcriptomic changes using the Gmix procedure (Broët et al, 2004), a fully Bayesian Normal mixture model with an unknown number of components. A probe set was classified as a copy-number-driven gene if its posterior probability of relationship between genomic and transcriptomic changes was greater than 0.5, according to the Bayes rule.

Relapse-Free Survival: Assessing Prognostic Impact of Genomic and Transcriptomic Changes Relapse-free survival (RFS) time was calculated from the date of the patients' surgery until either disease-related death, disease recurrence (either local or distant) or last follow-up examination. To analyze the prognostic impact of either genomic or transcriptomic changes, the inventors computed two sets of univariate score test statistics based on the semi-parametric Cox proportional hazards model (Cox et al, 1972). Here, the null hypothesis corresponded to the absence of a relationship between the instantaneous hazard rate for relapse and either genomic (copy number) status or gene expression measurement. To increase statistical power, the inventors also used information from our analysis of chromosomal patterns. Specifically, for a genomic clone considered as an exclusively amplified recurrent CNA, the few deleted samples for this clone were gathered with those having a modal genomic status. The converse was also performed for a clone considered as an exclusively deleted recurrent CNA. Using the Gmix procedure (Broët et al, 2004), the posterior probabilities of RFS being related to either the genomic status (genomic-survival posterior probabilities) or gene expression measurements (transcriptomic-survival posterior probabilities) were calculated.

Gene Signature Building Procedure Overview

The inventors designed a gene selection strategy to construct a copy-number driven gene expression signature, termed integrated signature (IS) in the following text, to predict RFS. In parallel, the inventors also constructed a conventional transcriptomic signature (TS), with the aim of comparing the performance of the IS to that of a more conventionally-derived expression signature not restricted to specific pathological properties of the cancer. For both signatures, a two-step procedure was considered: (i) In the first step (feature selection), the genomic clones or genes were individually ranked based on either their genomic-survival or transcriptomic-survival posterior probabilities. For IS (as seen below), the inventors also take into account for the relationship between genomic and transcriptomic changes. From these results, gene subset selections were performed. (ii) In the second step (signature development), a linear combination of the genes belonging to the selected subsets was computed leading to a gene expression signature.

Feature Selection

The major difference between the IS and TS feature selection step is that the former (IS) incorporates genomic information. For the IS, the inventors first selected genomic clones based on their genomic-survival posterior probabilities. Among the genes localized to those high-priority genomic areas, we then restricted our feature selection only to genes exhibiting copy-number-driven expression. In the classical way, for the TS the inventors selected the genes based on their transcriptomic-survival posterior probabilities. In practice, we selected the clones/genes in a top-down manner, starting with a genomic/transcriptomic-survival posterior probability of 99% and decreasing down to 75% with regular spacings (0.05 unit). This operation generated a series of nested gene/clone feature sets of different sizes depending on the chosen posterior probability threshold. This ranking approach is conceptually similar to previous reports (Beer et al, 2002; Raponi et al, 2006) but considers posterior probabilities rather than p-values.

Signature Development

The survival-associated gene expression signatures (IS, TS) were defined as linear combinations of the gene expression measurements of the selected genes weighted by their estimated Cox proportional hazards model regression coefficients (association between gene expression and RFS). More precisely, for feature gene sets (obtained in the feature selection step), the IS and TS signatures for each patient i were calculated as follows:

$$IS_{(i)}=\Sigma_{j\in\Omega}[\beta_j Z_{i,j}] \text{ and } TS_{(i)}=\Sigma_{j\in\Psi}[\beta^*_j Z^*_{i,j}]$$

Where $\beta_j$ (resp. $\beta^*_j$ for TS) was the transcriptomic Cox's regression coefficient for a gene j belonging to the feature sets $\Omega$ for IS (resp. $\Psi$) and $Z_{i,j}$ (resp. $Z^*_{i,j}$) was the gene expression measurement of a gene j for the patient i over $\Omega$. (resp. $\Psi$).

These signatures can be viewed as a compound covariate predictor for survival data (Simon et al, 2003; Tukey et al, 1993). Using these signatures, we classified patients into low- or high-risk profile groups using a cut-off value determined by the median of the estimated scores obtained through the cross-validation procedure described below.

Performance Evaluation of the Signature Building Processes

The discriminating ability of each signature building process (IS and TS) to separate high-risk from low-risk patients was evaluated at different posterior probability thresholds, leading to different feature gene set sizes. At each threshold, the entire process of feature gene selection, signature computation and high/low-risk group allocation was assessed using a five-fold cross-validation strategy for both signatures. At the end of the cross-validation procedure, each patient had an associated cross-validated predicted group membership and the logrank score statistic (as a measure of separation between high/low risk group) was calculated (Peto et al, 1972). For both signatures, the posterior probability threshold leading to the best performance in terms of logrank score statistic was retained and regarded as the optimal threshold for that signature.

To establish if the differences between the two survival distributions (low/high risk) were statistically significant (ie, the gene signature's performance is better than chance), the inventors randomly permuted the survival times (and associated censoring indicators) among the tumor samples, repeated the entire cross-validation procedure, and calculated a logrank score statistic as described above. Then, the inventors calculated the proportion of permutations having a logrank statistic greater or equal to the real (unpermuted) data [18] and used to detect a significant difference at the 5% level.

External Validation of the Consensus Gene Signatures

Since individual cross-validation runs can output distinct feature sets, we defined consensus feature sets for IS and TS comprising genes that were selected in at least two out of five of the cross-validated gene sets obtained at their optimal posterior probability thresholds. Finally, the IS and TS consensus feature sets were re-applied to the present series to determine consensus gene weightage scores for the final consensus IS and TS signatures.

The external validation or the transportability of the two consensus signatures (IS and TS) were tested on two independent publicly available microarray expression datasets, performed on either Affymetrix U133 Plus 2.0 or U133A oligonucleotide arrays. The first dataset (GEO accession number GSE3141) from Duke University (Bild et al, 2006) included a subselection of 31 stage I lung adenocarcinomas. The second independent dataset (GEO accession number GSE4573) from Michigan University (Raponi et al, 2006) included a subselection of 73 patients having stage I squamous cell lung carcinomas. For both datasets, the MASS-calculated signal intensities were normalized using quantile normalization.

To quantify the amount by which the consensus weights differ from the optimally trained weights (defined as the weights derived from each independent data sets), we computed the dispersion over the IS and TS gene sets by averaging the squared distance of the consensus weights from the optimal ones.

Results

This study was based on a homogeneous series of 85 lung cancer patients diagnosed with stage IB (pT2N0) primary adenocarcinoma or peripheral large cell carcinoma (Table 2).

TABLE 2

Patient clinicopathological characteristics

| Characteristic (N = 85) | N (%) |
|---|---|
| **Age at diagnosis** | |
| Median | 63 |
| Range | 42-84 |
| **Gender** | |
| Male | 63 (74) |
| Female | 22 (26) |
| **Tabacco (N = 78)** | |
| Smokers | 73 (86) |
| Non smokers | 5 (6) |
| **Type of resection** | |
| Wedge-resection/segmentectomy | 4 (5) |
| Lobectomy/bilobectomy | 78 (92) |
| Pneumonectomy | 3 (3) |
| Necrosis | 54 (64) |
| **Histology** | |
| Adenocarcinomas of mixed subtype | 56 (66) |
| Other adenocarcinomas | 9 (11) |
| Large cell carcinomas/others | 20 (23) |
| **Histological differentiation** | |
| Well differentiated | 42 (49) |
| Moderate differentiated | 7 (8) |
| Poorly/no differentiated | 36 (43) |
| Other histological paramaters | |
| Lymphatic invasion | 44 (52) |
| Blood vessel invasion | 53 (62) |
| Visceral pleura invasion (N = 84) | 53 (63) |
| TTF-1 expression (N = 84) | 51 (61) |

N = number

As the impact of comorbidity on survival after surgical resection of stage I NSCLC patients has been recognized (Moro-Sibilot et al, 2005), the inventors focused on relapse-free survival (RFS) as a clinical endpoint. The median follow-up was 46 months. At the time of analysis, 29 disease-related deaths or tumor relapses had occurred. For the entire cohort, the RFS rate was 79.3% [CI95%: 70.8-88.9] at 24 months, similar to previous observations (Yang et al, 2005). No significant relationships between RFS and classical clinicopathological variables (age, pleural involvement, vascular invasion) was found.

Patterns of CNAs

Using BAC array-CGH technology, the inventors analyzed the frequencies of genomic amplification/deletion events in the present series. The global copy number patterns observed in the present series were concordant with those of previous lung cancer studies, showing amplification of 5q, 6q, 7 and 8q and deletions at 3p, 5q13 and 16q (Balsara et al, 2002; Garnis et al, 2006; Weir et al, 2007; Tonon et al, 2005). Strikingly, the majority of oncogenes and tumor suppressor genes known to be associated with quantitative genomic changes in NSCLC were commonly found in close proximity to the central peaks of recurrent CNAs. An advantage of the high-resolution array-CGH platform is its ability to interrogate regions of large chromosomal aberration to reveal fine-scale alterations. The inventors observed a focal amplification spanning the well known CCND1 (Cyclin D1) gene in 19% of cases (Garnis et al, 2006). Also, at the chromosome 5p where a single recurrent amplicon was previously reported (Garnis et al, 2006; Tonon et al, 2005); the inventors detected two distinct amplification events centered on the hTERT and SKP2 genes, in 56.5% and 40% of cases, respectively. The inventors defined patterns of recurrent CNAs that reflect the propensity of each genomic region to be amplified or deleted. From this chromosomal patterns analysis, 14.4% and 20.9% of the clones were classified as "exclusively amplified" or "exclusively deleted" recurrent CNAs, respectively. The most frequent exclusively amplified CNAs were observed at chromosome 1q, 5p, 6p, 7, 8q and 20, while the most frequent exclusively deleted CNAs occurred at 3p, 5q, 6q, 8p, 13, 15, 16q, 17p and 18q. The PIK3CA gene, located at 3q26.3 locus, has been reported to be exclusively amplified in squamous cell carcinoma (Balsara et al, 2002; Tonon et al, 2005) and, as expected, was not identified as a recurrent CNA in our adenocarcinoma series. In a similar vein, the inventors observed recurrent gains of 6p and recurrent losses of 13, both of which have been shown to occur in lung adenocarcinomas (Kim et al, 2005; Garnis et al, 2006).

Copy-Number-Driven Genes

Using a Bayesian Normal mixture model approach (Broët et al, 2004), the inventors quantified for each gene its posterior probability for having expression changes correlated with copy number changes using the seventy-four samples for which both array-CGH and expression microarrays had been performed. The distribution of the linear correlation-based statistics formed a normal-shaped curve shifted towards positive values. Though the inventors observed several competing mixture models that provided a good fit to the data, the estimated component means of normal distributions for these mixture models were always positive, consistent with the notion that amplifications are associated with increased expression, and deletions with loss of expression. Applying the Bayes allocation rule, 42% of the genes were classified as copy-number-driven, consistent with a global influence of DNA copy number alterations on gene expression in lung cancer. Similar observations have been reported for breast cancer (Pollack et al, 2002). An example of a positive correlation validated at the DNA, mRNA and protein levels is shown for CCND1. Consistent with a high positive correlation between genomic and transcriptomic changes for CCND1 (p<0.0001), protein-level analysis using immunohistochemistry was statistically related with gene amplification (p=0.02).

Prognostic Impact of Genomic Changes

The prognostic impact of copy number changes on RFS was calculated using a classical univariate Cox proportional hazard model. At a FDR (false discovery rate) threshold of 10%, the clones with the highest posterior probabilities of being correlated to the time to relapse were located in the following regions: 1p36, 7p12, 7q11, 7q31-33, 8q22, 11q12, 14q21, 16p11-13, 16q22-q24, 20q11, 21q21-22, and 22q11-12. Of note, a highly significant increased risk for relapse was found for the amplified region 7q31-33 known to contain several genes that have been related to cancer aggressiveness (MET, POT1, CAV1 and CAV2). Paradoxically, a significant decreased risk for relapse was found for deletion of chromosome 16q containing the tumor suppressor gene WWOX. However, this region also contains the oncogene MAF whose deletion may act to reduce cancer progression, and thus explain the protective effect of this chromosomal loss. This observation highlights the fact that genes with both positive and negative tumorigenic effects may localize to the same areas of genomic alteration leading to complex biological interactions that influence clinical outcomes.

The prognostic impact of global gene expression changes on RFS was also calculated. Unlike the survival score statistics for the BAC genomic clones, the gene expression statistics did not show a clear trend over the chromosomes. For a global 10% FDR, the selected scores were exclusively positive, indicating that overexpression increases relapse risk, while underexpression decreases relapse risk.

Construction and Internal Validation of Prognostic Gene Signatures

Next the inventors sought to build an "integrated" predictive model of RFS based solely on the expressed portions of the most clinically relevant cytogenetic abnormalities. For this purpose, the inventors restricted the gene selection specifically to copy-number-driven genes located within exclusively amplified or deleted recurrent CNAs, the latter having posterior probabilities of being associated with RFS above a defined statistical threshold (see Methods). The inventors then constructed a compound covariate predictor, termed the integrated signature (IS), using an approach similar to that of Simon et al, 2003. We performed five-fold cross-validation to evaluate the two classifier-building processes (feature selection and signature construction) with respect to their discriminatory capabilities. To compare the IS with a more conventionally-derived expression signature not restricted to specific pathological properties of the cancer, the inventors also constructed a transcriptomic signature (TS) using the same methodology, with the exception of feature selection. To select genes for constructing the TS, the inventors considered all genes irrespective of their genomic status, and ranked them based solely on their expression correlations with RFS. They found that both the IS and TS processes were able to select signatures that provided statistically significant discrimination between low and high risk patients. Nevertheless, the IS process showed higher and more stable discriminating power than the TS process when increasing or decreasing the feature selection threshold (posterior probability) which relates to the number of selected clones/gene across the different cross-validation runs.

Based on the cross-validation curves, the inventors defined optimal threshold values (0.92 for IS and 0.88 for TS) that strike a balance between having a good discriminating ability and allowing for a minimum number of selected genes. Thus, the IS defined low and high risk groups with RFS rates at 24 months of 94.5% [CI95%: 87.3-100.0] and 63.7% [CI95%: 48.2-84.2], respectively (FIG. 1*a*). Similarly, the TS defined low and high risk groups with RFS rates at 24 months of 87.1% [CI95%: 76.1-99.7] and 74.0% [CI95%: 60.6-90.3], respectively (FIG. 1*b*). By doing random permutations, we found that the survival differences between the low and high risk groups defined by the IS and TS were significantly better than expected by chance (p=0.02 and p=0.05, respectively). Finally, as individual cross-validation runs can sometimes yield signatures with different sets of genes, we identified final consensus gene sets for the IS and TS comprising genes that were commonly selected in repeated cross-validations. The consensus IS was composed of 171 probe sets representing 103 unique genes located on chromosomes 7, 16, 20 and 22 (Table B).

The consensus TS was composed of 58 probe sets representing 43 unique genes scattered over the genome (Table 3).

TABLE 3

| Transcriptomic signature | | | |
|---|---|---|---|
| chromosome | Gene | Affy | weights |
| 1 | — | 225934_at | 0.945 |
| 1 | — | 213114_at | 1.15 |
| 1 | UROD | 208970_s_at | 1.66 |
| 1 | — | 239982_at | 1.49 |
| 1 | — | 230433_at | 0.987 |
| 1 | — | 229798_s_at | 0.783 |
| 1 | SLAMF9 | 1553770_a_at | 1.09 |
| 1 | — | 1561530_at | 2.64 |
| 2 | — | 226765_at | 1.11 |
| 2 | LOC647115 | 231698_at | 1.06 |
| 2 | IFIH1 | 216020_at | 2.7 |
| 2 | C2orf10 | 215767_at | 1.17 |
| 3 | MAP4 | 200835_s_at | 1.47 |
| 3 | PTK9L | 202009_at | 2.64 |
| 4 | C4orf10 | 214123_s_at | 1.46 |
| 4 | LOC92689 | 226697_at | 0.957 |
| 5 | PDLIM4 | 218691_s_at | 0.862 |
| 5 | SRA1 | 224364_at | 1.42 |
| 5 | DKFZp586C072 | 2319S7_at | 1.97 |
| 5 | RGS14 | 38290_at | 1.39 |
| 5 | MGAT1 | 232690_at | 1.8 |
| 6 | — | 239303_at | 1.07 |
| 7 | GNA12 | 231309_at | 2.03 |
| 7 | — | 209972_s_at | 0.776 |
| 7 | HSPC047 | 220692_at | 0.959 |
| 7 | MKLN1 | 242984_at | 2.09 |
| 7 | BPGM | 238724_at | 0.949 |
| 7 | PRR8 | 1554096_a_at | 1.04 |
| 10 | LOC653458 | 226802_s_at | 1.28 |
| 12 | PTK9 | 214008_at | 1.52 |
| 12 | IKIP | 236249_at | 1.05 |
| 13 | — | 221995_s_at | 0.839 |
| 13 | — | 228913_at | 1.36 |
| 14 | MRPL52 | 221997_s_at | 0.744 |
| 14 | ARG2 | 203945_at | 0.96 |
| 14 | — | 230790_x_at | 0.767 |
| 14 | CINP | 217598_at | 1.3 |
| 15 | TMED3 | 208337_at | 1.21 |
| 16 | C16orf68 | 218945_at | 1.54 |
| 16 | CD2BP2 | 202257_s_at | 1.42 |
| 16 | SLC7A6OS | 232057_at | 1.17 |
| 17 | — | 233466_at | 1.74 |
| 17 | SLC16A3 | 213522_s_at | 0.872 |
| 19 | FLJ21742 | 232730_at | 2.09 |
| 19 | IL11 | 206924_at | 0.722 |
| 20 | PANK2 | 228966_at | 2.02 |
| 20 | — | 228309_at | 0.805 |
| 20 | NTSR1 | 207360_s_at | 1.47 |
| 20 | SLC2A4RG | 227362_at | 1.78 |
| 21 | U2AF1 | 242499_at | 1.57 |
| 22 | TXNRD2 | 211177_s_at | 0.79 |
| 22 | C22orf25 | 23539S_at | 1.45 |
| 22 | GAS2L1 | 209729_at | 1.1 |

TABLE 3-continued

| Transcriptomic signature | | | |
|---|---|---|---|
| chromosome | Gene | Affy | weights |
| 22 | — | 1568623_a_at | 1.25 |
| 22 | C22orf5 | 202027_at | 1.29 |
| 22 | TOMM22 | 229076_s_at | 1.79 |
| 22 | MAPK11 | 211499_s_at | 1.77 |
| 22 | — | 2133S3_at | 2.2 |

Not surprisingly, these two signatures included completely different sets of genes (only one gene in common) suggesting that they may reflect different biological aspects of carcinogenesis.

External Validation of the Consensus IS and TS Signatures

Next, the inventors assessed the transportability of the present consensus IS and TS in two independent lung cancer datasets. Importantly, the inventors did not re-train the weights on the new datasets, but rather directly applied the original gene weights as derived from their series (Table 4 and Table B).

TABLE 4

| Identification of known gene alterations | | | |
|---|---|---|---|
| Gene name | Alteration | Cytoband | N (%) |
| FHIT | D | 3p14.2 | 44 (51.8) |
| LIMD1 | D | 3p21.3 | 30 (35.3) |
| PIK3CA | A | 3q26.3 | 10 (11.8) |
| hTERT | A | 5p15.33 | 48 (56.5) |
| SKP2 | A | 5p13 | 34 (40) |
| EGFR-1 | A | 7p11.2 | 18 (21.2) |
| CMET | A | 7q31 | 18 (21.2) |
| MYC | A | 8q24.12-q24.13 | 34 (40) |
| CDKN2A | D | 9p21 | 22 (25.9) |
| PTEN | D | 10q23.3 | 18 (21.2) |
| FGF3 | A | 11q13 | 18 (21.2) |
| CCND1 | A | 11q13 | 16 (19) |
| CDK4 | A | 12q13.3-q14.1 | 10 (11.8) |
| MDM2 | A | 12q15 | 1 (8.2) |
| RB | D | 13q14.2 | 39 (45.9) |
| WWOX | D | 16q23.3-24.1 | 33 (38.8) |
| P53 | D | 17p13.1 | 32 (37.6) |
| TRAF4 | A | 17q11-q12 | 15 (17.6) |
| ERBB2 | A | 17q12 | 12 (14.1) |
| SMAD4 | D | 18q21-1 | 29 (34.1) |
| E2F | A | 20q11.2 | 20 (23.5) |

A: amplification, D; Deletion, N: number of tumor sample with the CNA.

In the Duke dataset subselection (consisting of 31 stage I lung adenocarcinomas analyzed on the same microarray platform U133Plus 2.0, [23]), the consensus IS showed a statistically significant difference in RFS between low and high risk patients (p=0.003), whereas the TS did not (FIG. 2a-2b). It is worth noting that varying the number of genes for the TS improved neither its internal nor external prognostic performance.

Since the locations and frequencies of recurrent CNAs are highly similar between adenocarcinomas and squamous cell carcinomas (SCCs) (Tonon et al, 2005), the inventors then wondered if the IS retained its prognostic significance when applied to SCCs as well. Specifically, they tested a series of 73 patients with stage I squamous cell carcinomas from a Michigan University study Raponi et al, 2006. Since the Michigan series was analyzed on the Affymetrix U133A microarray, only 93 of 171 probe sets for the IS, and 27 of 58 for the TS could be applied in validation. Nevertheless, the consensus IS showed a statistically significant difference in RFS between low and high risk patients (p=0.025), whereas the TS did not (FIG. 2c-2d).

To investigate the disparity between IS and TS performance, we analyzed the squared distance between the original consensus weights and optimally trained ones derived from the Duke and Michigan series. The distances were markedly smaller for the IS (Duke: 1.19, Michigan: 0.58) compared to the TS (Duke: 3.06, Michigan: 1.67) indicating that on the whole, the genes comprising the IS are more reproducibly associated with patient outcome in the independent series than the genes of the TS, which explains, in part, the better transportability of the IS. Together, these findings demonstrate a robust prognostic performance of the IS in predicting outcome in stage I NSCLC.

Discussion

In this work, the inventors combined genomic and gene expression information to derive a survival model rooted in recurrent CNAs associated with NSCLC. By restricting the model only to genes exhibiting copy-number driven expression, they generated a reproducible and transportable predictor of outcome in a subgroup of early stage lung cancer patients for which there is clearly a need for new prognostic factors. Specifically, the integrated signature accurately distinguished patients with high and low risk of relapse in our initial series, and was transportable to two independent stage I NSCLC series. These results clearly demonstrate that genome copy number information can be effectively used for generating prognostic models of lung cancer survival.

Other reports described genomic approaches to discriminate patients with early stage NSCLC. The inventors found that two published pure-gene expression based models, the 5- and 16-gene signatures from Chen et al. 2007 and a 50-gene prognostic signature from Beer et al., 2002 and Raponi et al, 2006 were not able to significantly discriminate between low and high-risk patients in the present cohort (data not shown). In contrast, the survival associated recurrent CNAs described in the present report are well-known to be observed across multiple NSCLC subtypes, such as amplifications of chromosome 7 and deletion of 16q (Tonon et al, 2005). The commonality of these CNAs may explain why our integrated predictor was also applicable to a squamous cell lung carcinoma cohort, despite it being built on an initial cohort of pure adenocarcinoma and large cell carcinomas.

From a clinical aspect, it is worth considering the potential impact of the present study on the treatment of Stage IB NSCLC patients—an important clinical population where treatment options are controversial. In a preliminary analysis, we found that in the Duke series, the clinical outcome of Stage I patients classified as 'high risk' and stage II patients were similar (FIG. 3b). This observation raises the potential implication that stage IB patients classified as 'high risk' by the integrated signature should be treated with chemotherapy similar to Stage II patients, as the benefit of chemotherapy treatment has already been conclusively shown in the latter group. By extension, Stage IB patients designated 'low risk' by the integrated signature might consider not undergoing chemotherapy treatment.

In conclusion, the inventors have described herein an integrative genomic strategy combining information regarding recurrent CNAs with genes exhibiting copy-number dependent expression for the creation of survival models. The inventors then demonstrated the robustness and transportability of this integrated signature for stratifying stage IB NSCLC patients. Their results conclusively show that genome abnormalities in copy number are likely to exert a profound influence in determining patient prognosis in NSCLC, and that this influence can be discerned by confining one's analysis to genes whose expression is affected by copy number.

REFERENCES

Adebonojo S A, Bowser A N, Moritz D M, Corcoran P C. Impact of revised stage classification of lung cancer on survival: a military experience. Chest 1999; 115:1507-13.

Balsara B R, Testa J R. Chromosomal imbalances in human lung cancer. Oncogene 2002; 21:6877-83.

Beer D G, Kardia S L, Huang C C, Giordano T J, Levin A M, Misek D E, et al. Gene-expression profiles predict survival of patients with lung adenocarcinoma. Nat Med 2002; 8:816-24.

Bild A H, Yao G, Chang J T, Wang Q, Potti A, Chasse D, et al. Oncogenic pathway signatures in human cancers as a guide to targeted therapies. Nature 2006; 439:353-7.

Broët P, Lewin A, Richardson S, Dalmasso C, Magdelenat H. A mixture model-based strategy for selecting sets of genes in multiclass response microarray experiments. Bioinformatics 2004; 20:2562-71

Broët P, Richardson S. Detection of gene copy number changes in CGH microarrays using a spatially correlated mixture model. Bioinformatics 2006; 22: 911-8.

Chen H Y, Yu S L, Chen C H, Chang G C, Chen C Y, Yuan A, et al. A five-gene signature and clinical outcome in non-small-cell lung cancer. N Engl J Med 2007; 356:11-20.

Collins, L G; Haines C, Perkel R, Enck R E Lung cancer: diagnosis and management. American Family Physician, 2007, 75 (1): 56-63.

Cox D R. Regression models and life tables (with discussion). J Royal Stat Soc B 1972; 74:187-220.

Duque J K, Lopez-Encuentra A, Porta R R, Bronchogenic Carcinoma Cooperative Group. Survival of 2,991 patients with surgical lung cancer: the denominator effect in survival. Chest 2005; 128: 2274-81.

Garber M E, Troyanskaya O G, Schluens K, Petersen S, Thaesler Z, Pacyna-Gengelbach M, et al. Diversity of gene expression in adenocarcinoma of the lung. Proc Natl Acad Sci. 2001; 98:13784-9.

Garnis C, Lockwood W W, Vucic E, Ge Y, Girard L, Minna J D, et al. High resolution analysis of non-small cell lung cancer cell lines by whole genome tiling path array CGH. Int J Cancer 2006; 118:1556-64.

Gelsi-Boyer V, Orsetti B, Cervera N, Finetti P, Sircoulomb F, et al. Comprehensive profiling of 8p11-12 amplification in breast cancer. Mol Cancer Res 2005; 3:655-67.

Irizarry R A, Hobbs B, Collin F, Beazer-Barclay Y D, Antonellis K J, Scherf U, et al. Exploration, normalization, and summaries of high density oligonucleotide array probe level data. Biostatistics 2003; 4: 249-64.

Ishkanian A S, Malloff C A, Watson S K, deLeeuw R J, Chi B, Coe B P, et al. A tiling resolution DNA microarray with complete coverage of the human genome. Nature Genetics 2004; 36:299-303.

Kim T M, Yim S H, Lee J S, Kwon M S, Ryu J W, et al. Genome-wide screening of genomic alterations and their clinicopathologic implications in non-small cell lung cancers. Clin Cancer Res 2005; 11:8235-42.

McLachlan G J, Peel D. Finite Mixture Models. New York: Wiley; 2000.

Moro-Sibilot D, Aubert A, Diab S, Lantuejoul S, Fourneret P, Brambilla E, et al. Comorbidities and Charlson score in resected stage I nonsmall cell lung cancer. Eur Respir J 2005; 26:480-6.

Mountain C F. Revisions in the International System for Staging Lung Cancer. Chest 1997; 111:1710-7.

Peto R, Peto J Asymptotically efficent rank. invariant test procedures (with discussion). J Royal Stat Soc A 1972; 135:185-207.

Pollack J R, Perou C M, Alizadeh A A, Eisen M B, Pergamenschikov A, Williams C F, Jeffrey S S, Botstein D, Brown P O. Genome-wide analysis of DNA copy-number changes using cDNA microarrays. Nat Genet. 1999 September; 23(1):41-6.

Pollack J R, Sorlie T, Perou C M, Rees C A, Jeffrey S S, Lonning P E, et al. Microarray analysis reveals a major direct role of DNA copy number alteration in the transcriptional program of human breast tumors. Proc Natl Acad Sci USA 2002; 99:12963-8.

Potti A, Mukherjee S, Petersen R, Dressman H K, Bild A, Koontz J, et al. A genomic strategy to refine prognosis in early-stage non-small-cell lung cancer. N Engl J Med 2006; 355:570-80.

Raponi M, Zhang Y, Yu J, Chen G, Lee G, Taylor J M, et al. Gene expression signatures for predicting prognosis of squamous cell and adenocarcinomas of the lung. Cancer Res 2006; 66:7466-72.

Simon R, Korn E, McShane L, Radmacher M, Wright G, Zhao Y. Design and Analysis of DNA Microarray Investigations, New York: Springer-Verlag; 2003. p 96-119.

Subramanian, J; Govindan R. Lung cancer in never smokers: a review. Journal of Clinical Oncology 2007, 25 (5): 561-570.

Tonon G, Wong K K, Maulik G, Brennan C, Feng B, Zhang Y, et al. High-resolution genomic profiles of human lung cancer. Proc Natl Acad Sci USA 2005; 102:9625-30.

Travis W D, Brambilla E, Muller-Mermelink H K, Harris C C Eds. Pathology & Genetics: Tumors of the Lung, Pleura, Thymus, & Heart. Geneva: IARC Press; 2004.

Tukey J W. Tightening the clinical trial. Control Clin Trials 1993; 14:266-85.

Weir B A, Woo M S, Getz G, Perner S, Ding L, Beroukhim R, et al. Characterizing the cancer genome in lung adenocarcinoma. Nature 2007; 450:893-8.

Yang Y H, Dudoit S, Luu P, Lin D M, Peng V, Ngai J, et al. Normalization for cDNA microarray data: a robust composite method addressing single and multiple slide systematic variation. Nucleic Acids Res 2002; 30:e15

Yang P, Allen M S, Aubry M C, Wampfler J A, Marks R S, Edell E S, et al. Clinical features of 5,628 primary lung cancer patients: experience at Mayo Clinic from 1997 to 2003. Chest 2005; 128: 452-62.

The invention claimed is:

1. An in vitro method for predicting clinical outcome of a patient affected with a non-small cell lung carcinoma (NSCLC), which method comprises determining the expression level of at least 8 genes in a biological sample of said patient, wherein said genes are GRM8, NRF1, USP7, PRO0149, TXNL48, GLG1, ZNRF1, and UBE2L3, wherein the expression level of said at least 8 genes is determined by determining the number of gene copies of said genes and the number of gene copies of said genes is quantified by a microarray-based comparative genomic hybridization (CGH) method or by a DNA chip based method.

2. The method of claim 1, wherein the patient is affected with an adenocarcinoma.

3. The method of claim 1, wherein the patient is affected with squamous cell carcinoma.

4. The method of claim 1, wherein the patient was diagnosed with a Stage I carcinoma.

5. The method of claim 4, wherein the patient was diagnosed with a Stage IB carcinoma.

6. The method of claim 1, further comprising the step of comparing the combined expression level of said genes with reference values.

7. The method of claim 1, wherein overexpression of said genes is used to assign a prognosis to a patient or assign a patient to a chemotherapeutic treatment.

8. The method of claim 1, wherein the biological sample is a tumor sample.

9. The method of claim 1, further comprising determining the expression level of the genes listed in Table B, or of a subcombination thereof.

10. The method of claim 9, comprising determining the expression level of any or all of the genes listed in Table C.

11. The method of claim 10, comprising determining the expression level of any or all of the genes listed in Table D.

12. The method of claim 11, comprising determining the expression level of any or all of the genes listed in Table E.

* * * * *

UNITED STATES PATENT AND TRADEMARK OFFICE

CERTIFICATE OF CORRECTION

PATENT NO. : 8,728,738 B2
APPLICATION NO. : 13/001081
DATED : May 20, 2014
INVENTOR(S) : Philippe Broet et al.

It is certified that error appears in the above-identified patent and that said Letters Patent is hereby corrected as shown below:

In the Specification

Column 1,
Line 40, "stage 1V." should read --stage IV.--.

Column 9,
Footnote (+), "and 5 identifies" should read --and identifies--.

Column 11,
Column "Gene" Row MKL2, "1562497_at;_1558777_at;218259_at" should read --1562497_at;1558777_at;218259_at--.

Column 15,
Line 45, "50 (Y0 formamide" should read --50% formamide--.

Column 18,
Line 15, "NCB's" should read --NCBIs--.

Column 21,
Lines 15-16, "MASS-calculated" should read --MAS5-calculated--.
Line 40, "Tabacco" should read --Tobacco--.
Line 57, "paramaters" should read --parameters--.

Column 24,
Line 38, Row "SRA1", Column "Affy", "224364_at" should read --224864_at--.
Line 39, Row "DKFZp586C072", Column "Affy", "2319S7_at" should read --231987_at--.
Line 41, Row "6", Column "Affy", "239303_at" should read --239903_at--.
Line 54, Row "TMED3", Column "Affy", "208337_at" should read --208837_at--.
Line 65, Row "C22orf25", Column "Affy", "23539S_at" should read --235396_at--.

Signed and Sealed this
Thirty-first Day of March, 2015

Michelle K. Lee
*Director of the United States Patent and Trademark Office*

Column 25,
Line 9, "2133S3_at" should read --213383_at--.
Line 38, Column "N (%)", "1 (8.2)" should read --7 (8.2)--.

SEQUENCE LISTING

```
<160> NUMBER OF SEQ ID NOS: 16

<210> SEQ ID NO 1
<211> LENGTH: 3572
<212> TYPE: DNA
<213> ORGANISM: Homo sapiens
<220> FEATURE:
<221> NAME/KEY: CDS
<222> LOCATION: (312)..(3038)
```

```
<400> SEQUENCE: 1

gaataattct gctacaaggc tgatttcaag gacatgaatt gttgacctca tcccaacatc      60

agaacctcag atgttctaat ttttgcacca ttccaggcaa gttgatctta taaggaaata     120

aaattgaacc ttaggggtct gatggaaatt cactgtgaca ttcaaatcaa gaaaacttgc     180

taatgcccac agagcctttt ccccatgggc cctgatggta gcctccagaa ggtgcagcct     240

caggtggtgc cctttcttct gtggcaagaa taaactttgg gtcttggatt gcaataccac     300

ctgtggagaa a atg gta tgc gag gga aag cga tca gcc tct tgc cct tgt      350
             Met Val Cys Glu Gly Lys Arg Ser Ala Ser Cys Pro Cys
             1               5                   10

ttc ttc ctc ttg acc gcc aag ttc tac tgg atc ctc aca atg atg caa       398
Phe Phe Leu Leu Thr Ala Lys Phe Tyr Trp Ile Leu Thr Met Met Gln
    15                  20                  25

aga act cac agc cag gag tat gcc cat tcc ata cgg gtg gat ggg gac       446
Arg Thr His Ser Gln Glu Tyr Ala His Ser Ile Arg Val Asp Gly Asp
30                  35                  40                  45

att att ttg ggg ggt ctc ttc cct gtc cac gca aag gga gag aga ggg       494
Ile Ile Leu Gly Gly Leu Phe Pro Val His Ala Lys Gly Glu Arg Gly
                50                  55                  60

gtg cct tgt ggg gag ctg aag aag gaa aag ggg att cac aga ctg gag       542
Val Pro Cys Gly Glu Leu Lys Lys Glu Lys Gly Ile His Arg Leu Glu
            65                  70                  75

gcc atg ctt tat gca att gac cag att aac aag gac cct gat ctc ctt       590
Ala Met Leu Tyr Ala Ile Asp Gln Ile Asn Lys Asp Pro Asp Leu Leu
        80                  85                  90

tcc aac atc act ctg ggt gtc cgc atc ctc gac acg tgc tct agg gac       638
Ser Asn Ile Thr Leu Gly Val Arg Ile Leu Asp Thr Cys Ser Arg Asp
    95                  100                 105

acc tat gct ttg gag cag tct cta aca ttc gtg cag gca tta ata gag       686
Thr Tyr Ala Leu Glu Gln Ser Leu Thr Phe Val Gln Ala Leu Ile Glu
110                 115                 120                 125

aaa gat gct tcg gat gtg aag tgt gct aat gga gat cca ccc att ttc       734
Lys Asp Ala Ser Asp Val Lys Cys Ala Asn Gly Asp Pro Pro Ile Phe
                130                 135                 140

acc aag ccc gac aag att tct ggc gtc ata ggt gct gca gca agc tcc       782
Thr Lys Pro Asp Lys Ile Ser Gly Val Ile Gly Ala Ala Ala Ser Ser
            145                 150                 155

gtg tcc atc atg gtt gct aac att tta aga ctt ttt aag ata cct caa       830
Val Ser Ile Met Val Ala Asn Ile Leu Arg Leu Phe Lys Ile Pro Gln
        160                 165                 170

atc agc tat gca tcc aca gcc cca gag cta agt gat aac acc agg tat       878
Ile Ser Tyr Ala Ser Thr Ala Pro Glu Leu Ser Asp Asn Thr Arg Tyr
    175                 180                 185

gac ttt ttc tct cga gtg gtt ccg cct gac tcc tac caa gcc caa gcc       926
Asp Phe Phe Ser Arg Val Val Pro Pro Asp Ser Tyr Gln Ala Gln Ala
190                 195                 200                 205

atg gtg gac atc gtg aca gca ctg gga tgg aat tat gtt tcg aca ctg       974
Met Val Asp Ile Val Thr Ala Leu Gly Trp Asn Tyr Val Ser Thr Leu
                210                 215                 220

gct tct gag ggg aac tat ggt gag agc ggt gtg gag gcc ttc acc cag      1022
Ala Ser Glu Gly Asn Tyr Gly Glu Ser Gly Val Glu Ala Phe Thr Gln
            225                 230                 235

atc tcg agg gag att ggt ggt gtt tgc att gct cag tca cag aaa atc      1070
Ile Ser Arg Glu Ile Gly Gly Val Cys Ile Ala Gln Ser Gln Lys Ile
        240                 245                 250

cca cgt gaa cca aga cct gga gaa ttt gaa aaa att atc aaa cgc ctg      1118
Pro Arg Glu Pro Arg Pro Gly Glu Phe Glu Lys Ile Ile Lys Arg Leu
    255                 260                 265
```

-continued

```
cta gaa aca cct aat gct cga gca gtg att atg ttt gcc aat gag gat      1166
Leu Glu Thr Pro Asn Ala Arg Ala Val Ile Met Phe Ala Asn Glu Asp
270                 275                 280                 285

gac atc agg agg ata ttg gaa gca gca aaa aaa cta aac caa agt ggg      1214
Asp Ile Arg Arg Ile Leu Glu Ala Ala Lys Lys Leu Asn Gln Ser Gly
                290                 295                 300

cat ttt ctc tgg att ggc tca gat agt tgg gga tcc aaa ata gca cct      1262
His Phe Leu Trp Ile Gly Ser Asp Ser Trp Gly Ser Lys Ile Ala Pro
            305                 310                 315

gtc tat cag caa gag gag att gca gaa ggg gct gtg aca att ttg ccc      1310
Val Tyr Gln Gln Glu Glu Ile Ala Glu Gly Ala Val Thr Ile Leu Pro
        320                 325                 330

aaa cga gca tca att gat gga ttt gat cga tac ttt aga agc cga act      1358
Lys Arg Ala Ser Ile Asp Gly Phe Asp Arg Tyr Phe Arg Ser Arg Thr
    335                 340                 345

ctt gcc aat aat cga aga aat gtg tgg ttt gca gaa ttc tgg gag gag      1406
Leu Ala Asn Asn Arg Arg Asn Val Trp Phe Ala Glu Phe Trp Glu Glu
350                 355                 360                 365

aat ttt ggc tgc aag tta gga tca cat ggg aaa agg aac agt cat ata      1454
Asn Phe Gly Cys Lys Leu Gly Ser His Gly Lys Arg Asn Ser His Ile
                370                 375                 380

aag aaa tgc aca ggg ctg gag cga att gct cgg gat tca tct tat gaa      1502
Lys Lys Cys Thr Gly Leu Glu Arg Ile Ala Arg Asp Ser Ser Tyr Glu
            385                 390                 395

cag gaa gga aag gtc caa ttt gta att gat gct gta tat tcc atg gct      1550
Gln Glu Gly Lys Val Gln Phe Val Ile Asp Ala Val Tyr Ser Met Ala
        400                 405                 410

tac gcc ctg cac aat atg cac aaa gat ctc tgc cct gga tac att ggc      1598
Tyr Ala Leu His Asn Met His Lys Asp Leu Cys Pro Gly Tyr Ile Gly
    415                 420                 425

ctt tgt cca cga atg agt acc att gat ggg aaa gag cta ctt ggt tat      1646
Leu Cys Pro Arg Met Ser Thr Ile Asp Gly Lys Glu Leu Leu Gly Tyr
430                 435                 440                 445

att cgg gct gta aat ttt aat ggc agt gct ggc act cct gtc act ttt      1694
Ile Arg Ala Val Asn Phe Asn Gly Ser Ala Gly Thr Pro Val Thr Phe
                450                 455                 460

aat gaa aac gga gat gct cct gga cgt tat gat atc ttc cag tat caa      1742
Asn Glu Asn Gly Asp Ala Pro Gly Arg Tyr Asp Ile Phe Gln Tyr Gln
            465                 470                 475

ata acc aac aaa agc aca gag tac aaa gtc atc ggc cac tgg acc aat      1790
Ile Thr Asn Lys Ser Thr Glu Tyr Lys Val Ile Gly His Trp Thr Asn
        480                 485                 490

cag ctt cat cta aaa gtg gaa gac atg cag tgg gct cat aga gaa cat      1838
Gln Leu His Leu Lys Val Glu Asp Met Gln Trp Ala His Arg Glu His
    495                 500                 505

act cac ccg gcg tct gtc tgc agc ctg ccg tgt aag cca ggg gag agg      1886
Thr His Pro Ala Ser Val Cys Ser Leu Pro Cys Lys Pro Gly Glu Arg
510                 515                 520                 525

aag aaa acg gtg aaa ggg gtc cct tgc tgc tgg cac tgt gaa cgc tgt      1934
Lys Lys Thr Val Lys Gly Val Pro Cys Cys Trp His Cys Glu Arg Cys
                530                 535                 540

gaa ggt tac aac tac cag gtg gat gag ctg tcc tgt gaa ctt tgc cct      1982
Glu Gly Tyr Asn Tyr Gln Val Asp Glu Leu Ser Cys Glu Leu Cys Pro
            545                 550                 555

ctg gat cag aga ccc aac atg aac cgc aca ggc tgc cag ctt atc ccc      2030
Leu Asp Gln Arg Pro Asn Met Asn Arg Thr Gly Cys Gln Leu Ile Pro
        560                 565                 570

atc atc aaa ttg gag tgg cat tct ccc tgg gct gtg gtg cct gtg ttt      2078
Ile Ile Lys Leu Glu Trp His Ser Pro Trp Ala Val Val Pro Val Phe
    575                 580                 585
```

```
gtt gca ata ttg gga atc atc gcc acc acc ttt gtg atc gtg acc ttt      2126
Val Ala Ile Leu Gly Ile Ile Ala Thr Thr Phe Val Ile Val Thr Phe
590                 595                 600                 605

gtc cgc tat aat gac aca cct atc gtg agg gct tca gga cgc gaa ctt      2174
Val Arg Tyr Asn Asp Thr Pro Ile Val Arg Ala Ser Gly Arg Glu Leu
                610                 615                 620

agt tac gtg ctc cta acg ggg att ttt ctc tgt tat tca atc acg ttt      2222
Ser Tyr Val Leu Leu Thr Gly Ile Phe Leu Cys Tyr Ser Ile Thr Phe
            625                 630                 635

tta atg att gca gca cca gat aca atc ata tgc tcc ttc cga cgg gtc      2270
Leu Met Ile Ala Ala Pro Asp Thr Ile Ile Cys Ser Phe Arg Arg Val
        640                 645                 650

ttc cta gga ctt ggc atg tgt ttc agc tat gca gcc ctt ctg acc aaa      2318
Phe Leu Gly Leu Gly Met Cys Phe Ser Tyr Ala Ala Leu Leu Thr Lys
    655                 660                 665

aca aac cgt atc cac cga ata ttt gag cag ggg aag aaa tct gtc aca      2366
Thr Asn Arg Ile His Arg Ile Phe Glu Gln Gly Lys Lys Ser Val Thr
670                 675                 680                 685

gcg ccc aag ttc att agt cca gca tct cag ctg gtg atc acc ttc agc      2414
Ala Pro Lys Phe Ile Ser Pro Ala Ser Gln Leu Val Ile Thr Phe Ser
                690                 695                 700

ctc atc tcc gtc cag ctc ctt gga gtg ttt gtc tgg ttt gtt gtg gat      2462
Leu Ile Ser Val Gln Leu Leu Gly Val Phe Val Trp Phe Val Val Asp
            705                 710                 715

ccc ccc cac atc atc att gac tat gga gag cag cgg aca cta gat cca      2510
Pro Pro His Ile Ile Ile Asp Tyr Gly Glu Gln Arg Thr Leu Asp Pro
        720                 725                 730

gag aag gcc agg gga gtg ctc aag tgt gac att tct gat ctc tca ctc      2558
Glu Lys Ala Arg Gly Val Leu Lys Cys Asp Ile Ser Asp Leu Ser Leu
    735                 740                 745

att tgt tca ctt gga tac agt atc ctc ttg atg gtc act tgt act gtt      2606
Ile Cys Ser Leu Gly Tyr Ser Ile Leu Leu Met Val Thr Cys Thr Val
750                 755                 760                 765

tat gcc att aaa acg aga ggt gtc cca gag act ttc aat gaa gcc aaa      2654
Tyr Ala Ile Lys Thr Arg Gly Val Pro Glu Thr Phe Asn Glu Ala Lys
                770                 775                 780

cct att gga ttt acc atg tat acc acc tgc atc att tgg tta gct ttc      2702
Pro Ile Gly Phe Thr Met Tyr Thr Thr Cys Ile Ile Trp Leu Ala Phe
            785                 790                 795

atc ccc atc ttt ttt ggt aca gcc cag tca gca gaa aag atg tac atc      2750
Ile Pro Ile Phe Phe Gly Thr Ala Gln Ser Ala Glu Lys Met Tyr Ile
        800                 805                 810

cag aca aca aca ctt act gtc tcc atg agt tta agt gct tca gta tct      2798
Gln Thr Thr Thr Leu Thr Val Ser Met Ser Leu Ser Ala Ser Val Ser
    815                 820                 825

ctg ggc atg ctc tat atg ccc aag gtt tat att ata att ttt cat cca      2846
Leu Gly Met Leu Tyr Met Pro Lys Val Tyr Ile Ile Ile Phe His Pro
830                 835                 840                 845

gaa cag aat gtt caa aaa cgc aag agg agc ttc aag gct gtg gtg aca      2894
Glu Gln Asn Val Gln Lys Arg Lys Arg Ser Phe Lys Ala Val Val Thr
                850                 855                 860

gct gcc acc atg caa agc aaa ctg atc caa aaa gga aat gac aga cca      2942
Ala Ala Thr Met Gln Ser Lys Leu Ile Gln Lys Gly Asn Asp Arg Pro
            865                 870                 875

aat ggc gag gtg aaa agt gaa ctc tgt gag agt ctt gaa acc aac act      2990
Asn Gly Glu Val Lys Ser Glu Leu Cys Glu Ser Leu Glu Thr Asn Thr
        880                 885                 890

tcc tct acc aag aca aca tat atc agt tac agc aat cat tca atc tga      3038
Ser Ser Thr Lys Thr Thr Tyr Ile Ser Tyr Ser Asn His Ser Ile
    895                 900                 905
```

```
aacagggaaa tggcacaatc tgaagagatg tggtatatga tcttaaatga tgaacatgag   3098

accgcaaaaa ttcactcctg gagatctccg tagactacaa tcaatcaaat caatagtcag   3158

tcttgtaagg aacaaaaatt agccatgagc caaaagtatc aataaacggg gagtgaagaa   3218

acccgtttta tacaataaaa ccaatgagtg tcaagctaaa gtattgctta ttcatgagca   3278

gttaaaacaa atcacaaaag gaaaactaat gttagctcgt gaaaaaaaat gctgttgaaa   3338

taaataatgt ctgatgttat tcttgtattt ttctgtgatt gtgagaactc ccgttcctgt   3398

cccacattgt ttaacttgta taagacaatg agtctgtttc ttgtaatggc tgaccagatt   3458

gaagccctgg gttgtgctaa aaataaatgc aatgattgat gcatgcaatt ttttatacaa   3518

ataatttatt tctaataata aaggaatgtt ttgcaaatgt taaaaaaaaa aaaa         3572


<210> SEQ ID NO 2
<211> LENGTH: 908
<212> TYPE: PRT
<213> ORGANISM: Homo sapiens

<400> SEQUENCE: 2

Met Val Cys Glu Gly Lys Arg Ser Ala Ser Cys Pro Cys Phe Phe Leu
1               5                   10                  15

Leu Thr Ala Lys Phe Tyr Trp Ile Leu Thr Met Met Gln Arg Thr His
            20                  25                  30

Ser Gln Glu Tyr Ala His Ser Ile Arg Val Asp Gly Asp Ile Ile Leu
        35                  40                  45

Gly Gly Leu Phe Pro Val His Ala Lys Gly Glu Arg Gly Val Pro Cys
    50                  55                  60

Gly Glu Leu Lys Lys Glu Lys Gly Ile His Arg Leu Glu Ala Met Leu
65                  70                  75                  80

Tyr Ala Ile Asp Gln Ile Asn Lys Asp Pro Asp Leu Leu Ser Asn Ile
                85                  90                  95

Thr Leu Gly Val Arg Ile Leu Asp Thr Cys Ser Arg Asp Thr Tyr Ala
            100                 105                 110

Leu Glu Gln Ser Leu Thr Phe Val Gln Ala Leu Ile Glu Lys Asp Ala
        115                 120                 125

Ser Asp Val Lys Cys Ala Asn Gly Asp Pro Pro Ile Phe Thr Lys Pro
    130                 135                 140

Asp Lys Ile Ser Gly Val Ile Gly Ala Ala Ala Ser Ser Val Ser Ile
145                 150                 155                 160

Met Val Ala Asn Ile Leu Arg Leu Phe Lys Ile Pro Gln Ile Ser Tyr
                165                 170                 175

Ala Ser Thr Ala Pro Glu Leu Ser Asp Asn Thr Arg Tyr Asp Phe Phe
            180                 185                 190

Ser Arg Val Val Pro Pro Asp Ser Tyr Gln Ala Gln Ala Met Val Asp
        195                 200                 205

Ile Val Thr Ala Leu Gly Trp Asn Tyr Val Ser Thr Leu Ala Ser Glu
    210                 215                 220

Gly Asn Tyr Gly Glu Ser Gly Val Glu Ala Phe Thr Gln Ile Ser Arg
225                 230                 235                 240

Glu Ile Gly Gly Val Cys Ile Ala Gln Ser Gln Lys Ile Pro Arg Glu
                245                 250                 255

Pro Arg Pro Gly Glu Phe Glu Lys Ile Ile Lys Arg Leu Leu Glu Thr
            260                 265                 270

Pro Asn Ala Arg Ala Val Ile Met Phe Ala Asn Glu Asp Asp Ile Arg
        275                 280                 285
```

```
Arg Ile Leu Glu Ala Ala Lys Lys Leu Asn Gln Ser Gly His Phe Leu
    290                 295                 300

Trp Ile Gly Ser Asp Ser Trp Gly Ser Lys Ile Ala Pro Val Tyr Gln
305                 310                 315                 320

Gln Glu Glu Ile Ala Glu Gly Ala Val Thr Ile Leu Pro Lys Arg Ala
                325                 330                 335

Ser Ile Asp Gly Phe Asp Arg Tyr Phe Arg Ser Arg Thr Leu Ala Asn
            340                 345                 350

Asn Arg Arg Asn Val Trp Phe Ala Glu Phe Trp Glu Glu Asn Phe Gly
        355                 360                 365

Cys Lys Leu Gly Ser His Gly Lys Arg Asn Ser His Ile Lys Lys Cys
    370                 375                 380

Thr Gly Leu Glu Arg Ile Ala Arg Asp Ser Ser Tyr Glu Gln Glu Gly
385                 390                 395                 400

Lys Val Gln Phe Val Ile Asp Ala Val Tyr Ser Met Ala Tyr Ala Leu
                405                 410                 415

His Asn Met His Lys Asp Leu Cys Pro Gly Tyr Ile Gly Leu Cys Pro
            420                 425                 430

Arg Met Ser Thr Ile Asp Gly Lys Glu Leu Leu Gly Tyr Ile Arg Ala
        435                 440                 445

Val Asn Phe Asn Gly Ser Ala Gly Thr Pro Val Thr Phe Asn Glu Asn
    450                 455                 460

Gly Asp Ala Pro Gly Arg Tyr Asp Ile Phe Gln Tyr Gln Ile Thr Asn
465                 470                 475                 480

Lys Ser Thr Glu Tyr Lys Val Ile Gly His Trp Thr Asn Gln Leu His
                485                 490                 495

Leu Lys Val Glu Asp Met Gln Trp Ala His Arg Glu His Thr His Pro
            500                 505                 510

Ala Ser Val Cys Ser Leu Pro Cys Lys Pro Gly Glu Arg Lys Lys Thr
        515                 520                 525

Val Lys Gly Val Pro Cys Cys Trp His Cys Glu Arg Cys Glu Gly Tyr
    530                 535                 540

Asn Tyr Gln Val Asp Glu Leu Ser Cys Glu Leu Cys Pro Leu Asp Gln
545                 550                 555                 560

Arg Pro Asn Met Asn Arg Thr Gly Cys Gln Leu Ile Pro Ile Ile Lys
                565                 570                 575

Leu Glu Trp His Ser Pro Trp Ala Val Val Pro Val Phe Val Ala Ile
            580                 585                 590

Leu Gly Ile Ile Ala Thr Thr Phe Val Ile Val Thr Phe Val Arg Tyr
        595                 600                 605

Asn Asp Thr Pro Ile Val Arg Ala Ser Gly Arg Glu Leu Ser Tyr Val
    610                 615                 620

Leu Leu Thr Gly Ile Phe Leu Cys Tyr Ser Ile Thr Phe Leu Met Ile
625                 630                 635                 640

Ala Ala Pro Asp Thr Ile Ile Cys Ser Phe Arg Arg Val Phe Leu Gly
                645                 650                 655

Leu Gly Met Cys Phe Ser Tyr Ala Ala Leu Leu Thr Lys Thr Asn Arg
            660                 665                 670

Ile His Arg Ile Phe Glu Gln Gly Lys Lys Ser Val Thr Ala Pro Lys
        675                 680                 685

Phe Ile Ser Pro Ala Ser Gln Leu Val Ile Thr Phe Ser Leu Ile Ser
    690                 695                 700

Val Gln Leu Leu Gly Val Phe Val Trp Phe Val Val Asp Pro Pro His
705                 710                 715                 720
```

```
Ile Ile Ile Asp Tyr Gly Glu Gln Arg Thr Leu Asp Pro Glu Lys Ala
                725                 730                 735

Arg Gly Val Leu Lys Cys Asp Ile Ser Asp Leu Ser Leu Ile Cys Ser
            740                 745                 750

Leu Gly Tyr Ser Ile Leu Leu Met Val Thr Cys Thr Val Tyr Ala Ile
        755                 760                 765

Lys Thr Arg Gly Val Pro Glu Thr Phe Asn Glu Ala Lys Pro Ile Gly
    770                 775                 780

Phe Thr Met Tyr Thr Thr Cys Ile Ile Trp Leu Ala Phe Ile Pro Ile
785                 790                 795                 800

Phe Phe Gly Thr Ala Gln Ser Ala Glu Lys Met Tyr Ile Gln Thr Thr
                805                 810                 815

Thr Leu Thr Val Ser Met Ser Leu Ser Ala Ser Val Ser Leu Gly Met
            820                 825                 830

Leu Tyr Met Pro Lys Val Tyr Ile Ile Ile Phe His Pro Glu Gln Asn
        835                 840                 845

Val Gln Lys Arg Lys Arg Ser Phe Lys Ala Val Val Thr Ala Ala Thr
    850                 855                 860

Met Gln Ser Lys Leu Ile Gln Lys Gly Asn Asp Arg Pro Asn Gly Glu
865                 870                 875                 880

Val Lys Ser Glu Leu Cys Glu Ser Leu Glu Thr Asn Thr Ser Ser Thr
                885                 890                 895

Lys Thr Thr Tyr Ile Ser Tyr Ser Asn His Ser Ile
            900                 905


<210> SEQ ID NO 3
<211> LENGTH: 3540
<212> TYPE: DNA
<213> ORGANISM: Homo sapiens
<220> FEATURE:
<221> NAME/KEY: CDS
<222> LOCATION: (118)..(1629)

<400> SEQUENCE: 3

ggcggcagaa gcggcagcgc tcgccattgc cgctggtggc aggaggctgc gaggagccgg      60

cgcggtcgca gtctccacgg cgcaggccca cggtagcgca gccgctctga gaacttc        117

atg gag gaa cac gga gtg acc caa acc gaa cat atg gct acc ata gaa       165
Met Glu Glu His Gly Val Thr Gln Thr Glu His Met Ala Thr Ile Glu
1               5                   10                  15

gca cat gca gtg gcc cag caa gtg cag cag gtc cat gtg gct act tac       213
Ala His Ala Val Ala Gln Gln Val Gln Gln Val His Val Ala Thr Tyr
            20                  25                  30

acc gag cat agt atg ctg agt gct gat gaa gac tcg cct tct tct ccc       261
Thr Glu His Ser Met Leu Ser Ala Asp Glu Asp Ser Pro Ser Ser Pro
        35                  40                  45

gag gac acc tct tac gat gac tca gat ata ctc aac tcc aca gca gct       309
Glu Asp Thr Ser Tyr Asp Asp Ser Asp Ile Leu Asn Ser Thr Ala Ala
    50                  55                  60

gat gag gtg aca gct cat ctg gca gct gca ggt cct gtg gga atg gcc       357
Asp Glu Val Thr Ala His Leu Ala Ala Ala Gly Pro Val Gly Met Ala
65                  70                  75                  80

gct gct gct gct gtg gca aca gga aag aaa cgg aaa cgg cct cat gta       405
Ala Ala Ala Ala Val Ala Thr Gly Lys Lys Arg Lys Arg Pro His Val
                85                  90                  95

ttt gag tct aat cca tct atc cgg aag agg caa caa aca cgt ttg ctt       453
Phe Glu Ser Asn Pro Ser Ile Arg Lys Arg Gln Gln Thr Arg Leu Leu
            100                 105                 110
```

```
cgg aaa ctt cga gcc acg tta gat gaa tat act act cgt gtg gga cag      501
Arg Lys Leu Arg Ala Thr Leu Asp Glu Tyr Thr Thr Arg Val Gly Gln
        115                 120                 125

caa gct att gtc ctc tgt atc tca ccc tcc aaa cct aac cct gtc ttt      549
Gln Ala Ile Val Leu Cys Ile Ser Pro Ser Lys Pro Asn Pro Val Phe
    130                 135                 140

aaa gtg ttt ggt gca gca cct ttg gag aat gtg gtg cgt aag tac aag      597
Lys Val Phe Gly Ala Ala Pro Leu Glu Asn Val Val Arg Lys Tyr Lys
145                 150                 155                 160

agc atg atc ctg gaa gac ctg gag tct gct ctg gca gaa cac gcc cct      645
Ser Met Ile Leu Glu Asp Leu Glu Ser Ala Leu Ala Glu His Ala Pro
                165                 170                 175

gcg cca cag gag gtt aac tca gaa ctg ccg cct ctc acc atc gac gga      693
Ala Pro Gln Glu Val Asn Ser Glu Leu Pro Pro Leu Thr Ile Asp Gly
            180                 185                 190

att cca gtc tct gtg gac aaa atg acc cag gcc cag ctt cgg gca ttt      741
Ile Pro Val Ser Val Asp Lys Met Thr Gln Ala Gln Leu Arg Ala Phe
        195                 200                 205

atc cca gag atg ctc aag tac tct aca ggt cgg gga aaa cca ggc tgg      789
Ile Pro Glu Met Leu Lys Tyr Ser Thr Gly Arg Gly Lys Pro Gly Trp
    210                 215                 220

ggg aaa gaa agc tgc aag ccc atc tgg tgg cct gaa gat atc ccc tgg      837
Gly Lys Glu Ser Cys Lys Pro Ile Trp Trp Pro Glu Asp Ile Pro Trp
225                 230                 235                 240

gca aat gtc cgg agt gat gtc cgc aca gaa gag caa aag cag agg gtt      885
Ala Asn Val Arg Ser Asp Val Arg Thr Glu Glu Gln Lys Gln Arg Val
                245                 250                 255

tca tgg acc cag gca cta cgg acc ata gtt aaa aac tgt tat aaa cag      933
Ser Trp Thr Gln Ala Leu Arg Thr Ile Val Lys Asn Cys Tyr Lys Gln
            260                 265                 270

cat ggg cgg gaa gac ctt ttg tat gcc ttt gaa gat cag caa acg caa      981
His Gly Arg Glu Asp Leu Leu Tyr Ala Phe Glu Asp Gln Gln Thr Gln
        275                 280                 285

aca cag gcc aca gcc aca cat agt ata gct cat ctt gta cca tca cag     1029
Thr Gln Ala Thr Ala Thr His Ser Ile Ala His Leu Val Pro Ser Gln
    290                 295                 300

act gta gtc cag act ttt agt aac cct gat ggc act gtc tca ctt atc     1077
Thr Val Val Gln Thr Phe Ser Asn Pro Asp Gly Thr Val Ser Leu Ile
305                 310                 315                 320

cag gtt ggt acg ggg gca aca gta gcc aca ttg gct gat gct tca gaa     1125
Gln Val Gly Thr Gly Ala Thr Val Ala Thr Leu Ala Asp Ala Ser Glu
                325                 330                 335

ttg cca acc acg gtc acc gtt gcc caa gtg aat tat tct gcc gtg gct     1173
Leu Pro Thr Thr Val Thr Val Ala Gln Val Asn Tyr Ser Ala Val Ala
            340                 345                 350

gat gga gag gtg gaa caa aat tgg gcc acg tta cag gga ggt gag atg     1221
Asp Gly Glu Val Glu Gln Asn Trp Ala Thr Leu Gln Gly Gly Glu Met
        355                 360                 365

acc atc cag acg acg caa gca tca gag gcc acc cag gcg gtg gca tcg     1269
Thr Ile Gln Thr Thr Gln Ala Ser Glu Ala Thr Gln Ala Val Ala Ser
    370                 375                 380

ttg gca gag gcc gca gtg gca gct tct cag gag atg cag cag gga gct     1317
Leu Ala Glu Ala Ala Val Ala Ala Ser Gln Glu Met Gln Gln Gly Ala
385                 390                 395                 400

aca gtc act atg gcg ctt aac agc gaa gct gcc gcc cat gct gtc gcc     1365
Thr Val Thr Met Ala Leu Asn Ser Glu Ala Ala Ala His Ala Val Ala
                405                 410                 415

acc ctg gct gag gcc acc tta caa ggt ggg gga cag atc gtc ttg tct     1413
Thr Leu Ala Glu Ala Thr Leu Gln Gly Gly Gly Gln Ile Val Leu Ser
            420                 425                 430
```

```
ggg gaa acc gca gca gcc gtc gga gca ctt act gga gtc caa gat gct     1461
Gly Glu Thr Ala Ala Ala Val Gly Ala Leu Thr Gly Val Gln Asp Ala
        435                 440                 445

aat ggc ctg gtc cag atc cct gtg agc atg tac cag act gtg gtg acc     1509
Asn Gly Leu Val Gln Ile Pro Val Ser Met Tyr Gln Thr Val Val Thr
    450                 455                 460

agc ctc gcc cag ggc aac gga cca gtg cag gtg gcc atg gcc cct gtg     1557
Ser Leu Ala Gln Gly Asn Gly Pro Val Gln Val Ala Met Ala Pro Val
465                 470                 475                 480

acc acc agg ata tca gac agc gca gtc acc atg gac ggc caa gct gtg     1605
Thr Thr Arg Ile Ser Asp Ser Ala Val Thr Met Asp Gly Gln Ala Val
                485                 490                 495

gag gtg gtg aca ttg gaa cag tga catacagcca tattatggca tcgttttcta    1659
Glu Val Val Thr Leu Glu Gln
            500

gtctacttca aaatttttta cacgtttgca gaggtgcaat caaatggaat taagtctctc   1719

gactttggaa ggaaagtttt gttaaccttt tttttttaa aaggaagaaa gcggattttg    1779

gaattgcatt ttttaaagca ccactcttga ttttctggga ttggtgaaga aactgcattg   1839

tcaatttcac tgtcccaaaa aagccaaatt gtggcaggac ttctttctgc ggaaatgtgt   1899

gtgtatactt atgtgtgtgt atgtgtgagt gtgaatatat gtatatgtgt acatatggac   1959

atacacattt acatatatat aaagtatata tatacatata tatatatata tatgtatgaa   2019

acccgcatgg aattatctgt atgaaatcaa ggtgcgctgt ggaaacaata attcacccag   2079

tttagtgggt ggtagggtac gtggccagac acagtcaccc agtttttgtt cataccaggg   2139

tcatgcgttg agctactgac aaactcaggc ggaggtgacc atgcccttca ccaaagctgc   2199

ctcccagtgg ccacacagaa ctctccctgc tggactcacc tgaggaaaga ggctccagca   2259

tggggtgggt cagagatgtg cttgcaaggt ccagggactg cgtggtctgc cagctgagat   2319

gctcctcggg ctggcccagg tgctgacctt gccacaggca gatgaatgtc ttgaaagctc   2379

ccgggcctca gcctcccatc tcctctcctt cccaggaatc cttgatctca tgactattaa   2439

aatgttgctc tggttttaag gtcagtcctg aattgctcgt atatatgaac tgaaggtaac   2499

cgaagtatta ggggtttgag gagtgcgtgc gtgtaagtgt gcttgtgtgt gtgcgtgcat   2559

ggtgggggag aggatgggaa gggggcgggg gcagtggaag ggaaaggaag gaaagaaaaa   2619

tcgtcctaga ccaggataca cccgtgggag caattttctc tactgtctgt agcttcacag   2679

aggaggcgct ggaatgaaca agaagagaca tctggtctgt ggccacagca ccctgaacgc   2739

ccctgatctt gtgtgatctt ggaagctaag cttggttggg cccggtcagt acgcggaagg   2799

gaagaaggga cacctggcca tagaaaacag ctgagggtgt ttgctgtgtt cctggatcag   2859

gccctgcttc agaagggact cctggaggcc catgttcctt gatgcaacct cgtggcccag   2919

gccgggagca gcttgcctcc tcagaggtgt tgactatctg ggtgttcttg gtaaccgtta   2979

actctgtctt tctcagctgc aagccctgag tctccagtag ctgaattcac ctgacttttc   3039

aacaggccaa atctctgaac cttgagtaca gggacagctc ctcctccctc ctcccagctc   3099

tccccatgtg tgtgatggtg tatttaatgt gttttttaa tgcgacatta aaagattctc    3159

cacgtcttgc tcaacctttg agagaagttt cagattcttg tatttgcttg ttttatataa   3219

aactatctaa tgttctttat atgttctttt ctgtacgtaa tggggggagg ggagggaaat   3279

ttacatataa atagtcctag ttctacaatt tgttattttt ttaattatta ttttttatcg   3339

tcattgtgaa gttgtccagg gactttaaag tccatgttcc tttgtggtga aataacctcc   3399

aaatagtttg agaagttgcc aagacgaaga aaaaagcaaa accccagtag cagagcatgg   3459
```

```
attctgtgtt gtttcccatt ctgtctttga ctgcctcatt caataaatag ttaaaaatgt   3519

ggcaacagga aaaaaaaaaa a                                             3540


<210> SEQ ID NO 4
<211> LENGTH: 503
<212> TYPE: PRT
<213> ORGANISM: Homo sapiens

<400> SEQUENCE: 4

Met Glu Glu His Gly Val Thr Gln Thr Glu His Met Ala Thr Ile Glu
1               5                   10                  15

Ala His Ala Val Ala Gln Gln Val Gln Gln Val His Val Ala Thr Tyr
            20                  25                  30

Thr Glu His Ser Met Leu Ser Ala Asp Glu Asp Ser Pro Ser Ser Pro
        35                  40                  45

Glu Asp Thr Ser Tyr Asp Asp Ser Asp Ile Leu Asn Ser Thr Ala Ala
    50                  55                  60

Asp Glu Val Thr Ala His Leu Ala Ala Ala Gly Pro Val Gly Met Ala
65                  70                  75                  80

Ala Ala Ala Ala Val Ala Thr Gly Lys Lys Arg Lys Arg Pro His Val
                85                  90                  95

Phe Glu Ser Asn Pro Ser Ile Arg Lys Arg Gln Gln Thr Arg Leu Leu
            100                 105                 110

Arg Lys Leu Arg Ala Thr Leu Asp Glu Tyr Thr Thr Arg Val Gly Gln
        115                 120                 125

Gln Ala Ile Val Leu Cys Ile Ser Pro Ser Lys Pro Asn Pro Val Phe
    130                 135                 140

Lys Val Phe Gly Ala Ala Pro Leu Glu Asn Val Val Arg Lys Tyr Lys
145                 150                 155                 160

Ser Met Ile Leu Glu Asp Leu Glu Ser Ala Leu Ala Glu His Ala Pro
                165                 170                 175

Ala Pro Gln Glu Val Asn Ser Glu Leu Pro Pro Leu Thr Ile Asp Gly
            180                 185                 190

Ile Pro Val Ser Val Asp Lys Met Thr Gln Ala Gln Leu Arg Ala Phe
        195                 200                 205

Ile Pro Glu Met Leu Lys Tyr Ser Thr Gly Arg Gly Lys Pro Gly Trp
    210                 215                 220

Gly Lys Glu Ser Cys Lys Pro Ile Trp Trp Pro Glu Asp Ile Pro Trp
225                 230                 235                 240

Ala Asn Val Arg Ser Asp Val Arg Thr Glu Glu Gln Lys Gln Arg Val
                245                 250                 255

Ser Trp Thr Gln Ala Leu Arg Thr Ile Val Lys Asn Cys Tyr Lys Gln
            260                 265                 270

His Gly Arg Glu Asp Leu Leu Tyr Ala Phe Glu Asp Gln Gln Thr Gln
        275                 280                 285

Thr Gln Ala Thr Ala Thr His Ser Ile Ala His Leu Val Pro Ser Gln
    290                 295                 300

Thr Val Val Gln Thr Phe Ser Asn Pro Asp Gly Thr Val Ser Leu Ile
305                 310                 315                 320

Gln Val Gly Thr Gly Ala Thr Val Ala Thr Leu Ala Asp Ala Ser Glu
                325                 330                 335

Leu Pro Thr Thr Val Thr Val Ala Gln Val Asn Tyr Ser Ala Val Ala
            340                 345                 350

Asp Gly Glu Val Glu Gln Asn Trp Ala Thr Leu Gln Gly Gly Glu Met
        355                 360                 365
```

```
Thr Ile Gln Thr Thr Gln Ala Ser Glu Ala Thr Gln Ala Val Ala Ser
    370                 375                 380

Leu Ala Glu Ala Ala Val Ala Ala Ser Gln Glu Met Gln Gln Gly Ala
385                 390                 395                 400

Thr Val Thr Met Ala Leu Asn Ser Glu Ala Ala Ala His Ala Val Ala
                405                 410                 415

Thr Leu Ala Glu Ala Thr Leu Gln Gly Gly Gly Gln Ile Val Leu Ser
            420                 425                 430

Gly Glu Thr Ala Ala Ala Val Gly Ala Leu Thr Gly Val Gln Asp Ala
        435                 440                 445

Asn Gly Leu Val Gln Ile Pro Val Ser Met Tyr Gln Thr Val Val Thr
    450                 455                 460

Ser Leu Ala Gln Gly Asn Gly Pro Val Gln Val Ala Met Ala Pro Val
465                 470                 475                 480

Thr Thr Arg Ile Ser Asp Ser Ala Val Thr Met Asp Gly Gln Ala Val
                485                 490                 495

Glu Val Val Thr Leu Glu Gln
            500


<210> SEQ ID NO 5
<211> LENGTH: 5412
<212> TYPE: DNA
<213> ORGANISM: Homo sapiens
<220> FEATURE:
<221> NAME/KEY: CDS
<222> LOCATION: (200)..(3508)

<400> SEQUENCE: 5

gtacgtgcgc gtctccctgc cgccgccgcc gcccgccgcg ggccgccccg gggccgccgt      60

cgccgacgac gcgcgggagg aggaggagga ggccgccccg ccgccgccgc cgccgccgcc     120

gccccggctc gccgccgccc gcccgccggg ctcgcagccc cggcccccgg ccgcaggcga     180

ggcccaggcc gcggccgac atg aac cac cag cag cag cag cag cag cag aaa      232
                     Met Asn His Gln Gln Gln Gln Gln Gln Gln Lys
                     1               5                   10

gcg ggc gag cag cag ttg agc gag ccc gag gac atg gag atg gaa gcg       280
Ala Gly Glu Gln Gln Leu Ser Glu Pro Glu Asp Met Glu Met Glu Ala
            15                  20                  25

gga gat aca gat gac cca cca aga att act cag aac cct gtg atc aat       328
Gly Asp Thr Asp Asp Pro Pro Arg Ile Thr Gln Asn Pro Val Ile Asn
        30                  35                  40

ggg aat gtg gcc ctg agt gat gga cac aac acc gcg gag gag gac atg       376
Gly Asn Val Ala Leu Ser Asp Gly His Asn Thr Ala Glu Glu Asp Met
    45                  50                  55

gag gat gac acc agt tgg cgc tcc gag gca acc ttt cag ttc act gtg       424
Glu Asp Asp Thr Ser Trp Arg Ser Glu Ala Thr Phe Gln Phe Thr Val
60                  65                  70                  75

gag cgc ttc agc aga ctg agt gag tcg gtc ctt agc cct ccg tgt ttt       472
Glu Arg Phe Ser Arg Leu Ser Glu Ser Val Leu Ser Pro Pro Cys Phe
                80                  85                  90

gtg cga aat ctg cca tgg aag att atg gtg atg cca cgc ttt tat cca       520
Val Arg Asn Leu Pro Trp Lys Ile Met Val Met Pro Arg Phe Tyr Pro
            95                  100                 105

gac aga cca cac caa aaa agc gta gga ttc ttt ctc cag tgc aat gct       568
Asp Arg Pro His Gln Lys Ser Val Gly Phe Phe Leu Gln Cys Asn Ala
        110                 115                 120

gaa tct gat tcc acg tca tgg tct tgc cat gca caa gca gtg ctg aag       616
Glu Ser Asp Ser Thr Ser Trp Ser Cys His Ala Gln Ala Val Leu Lys
    125                 130                 135
```

```
ata ata aat tac aga gat gat gaa aag tcg ttc agt cgt cgt att agt      664
Ile Ile Asn Tyr Arg Asp Asp Glu Lys Ser Phe Ser Arg Arg Ile Ser
140                 145                 150                 155

cat ttg ttc ttc cat aaa gaa aat gat tgg gga ttt tcc aat ttt atg      712
His Leu Phe Phe His Lys Glu Asn Asp Trp Gly Phe Ser Asn Phe Met
                160                 165                 170

gcc tgg agt gaa gtg acc gat cct gag aaa gga ttt ata gat gat gac      760
Ala Trp Ser Glu Val Thr Asp Pro Glu Lys Gly Phe Ile Asp Asp Asp
            175                 180                 185

aaa gtt acc ttt gaa gtc ttt gta cag gcg gat gct ccc cat gga gtt      808
Lys Val Thr Phe Glu Val Phe Val Gln Ala Asp Ala Pro His Gly Val
        190                 195                 200

gcg tgg gat tca aag aag cac aca ggc tac gtc ggc tta aag aat cag      856
Ala Trp Asp Ser Lys Lys His Thr Gly Tyr Val Gly Leu Lys Asn Gln
    205                 210                 215

gga gcg act tgt tac atg aac agc ctg cta cag acg tta ttt ttc acg      904
Gly Ala Thr Cys Tyr Met Asn Ser Leu Leu Gln Thr Leu Phe Phe Thr
220                 225                 230                 235

aat cag cta cga aag gct gtg tac atg atg cca acc gag ggg gat gat      952
Asn Gln Leu Arg Lys Ala Val Tyr Met Met Pro Thr Glu Gly Asp Asp
                240                 245                 250

tcg tct aaa agc gtc cct tta gca tta caa aga gtg ttc tat gaa tta     1000
Ser Ser Lys Ser Val Pro Leu Ala Leu Gln Arg Val Phe Tyr Glu Leu
            255                 260                 265

cag cat agt gat aaa cct gta gga aca aaa aag tta aca aag tca ttt     1048
Gln His Ser Asp Lys Pro Val Gly Thr Lys Lys Leu Thr Lys Ser Phe
        270                 275                 280

ggg tgg gaa act tta gat agc ttc atg caa cat gat gtt cag gag ctt     1096
Gly Trp Glu Thr Leu Asp Ser Phe Met Gln His Asp Val Gln Glu Leu
    285                 290                 295

tgt cga gtg ttg ctc gat aat gtg gaa aat aag atg aaa ggc acc tgt     1144
Cys Arg Val Leu Leu Asp Asn Val Glu Asn Lys Met Lys Gly Thr Cys
300                 305                 310                 315

gta gag ggc acc ata ccc aaa tta ttc cgc ggc aaa atg gtg tcc tat     1192
Val Glu Gly Thr Ile Pro Lys Leu Phe Arg Gly Lys Met Val Ser Tyr
                320                 325                 330

atc cag tgt aaa gaa gta gac tat cgg tct gat aga aga gaa gat tat     1240
Ile Gln Cys Lys Glu Val Asp Tyr Arg Ser Asp Arg Arg Glu Asp Tyr
            335                 340                 345

tat gat atc cag cta agt atc aaa gga aag aaa aat ata ttt gaa tca     1288
Tyr Asp Ile Gln Leu Ser Ile Lys Gly Lys Lys Asn Ile Phe Glu Ser
        350                 355                 360

ttt gtg gat tat gtg gca gta gaa cag ctc gat ggg gac aat aaa tac     1336
Phe Val Asp Tyr Val Ala Val Glu Gln Leu Asp Gly Asp Asn Lys Tyr
    365                 370                 375

gac gct ggg gaa cat ggc tta cag gaa gca gag aaa ggt gtg aaa ttc     1384
Asp Ala Gly Glu His Gly Leu Gln Glu Ala Glu Lys Gly Val Lys Phe
380                 385                 390                 395

cta aca ttg cca cca gtg tta cat cta caa ctg atg aga ttt atg tat     1432
Leu Thr Leu Pro Pro Val Leu His Leu Gln Leu Met Arg Phe Met Tyr
                400                 405                 410

gac cct cag acg gac caa aat atc aag atc aat gat agg ttt gaa ttc     1480
Asp Pro Gln Thr Asp Gln Asn Ile Lys Ile Asn Asp Arg Phe Glu Phe
            415                 420                 425

cca gag cag tta cca ctt gat gaa ttt ttg caa aaa aca gat cct aag     1528
Pro Glu Gln Leu Pro Leu Asp Glu Phe Leu Gln Lys Thr Asp Pro Lys
        430                 435                 440

gac cct gca aat tat att ctt cat gca gtc ctg gtt cat agt gga gat     1576
Asp Pro Ala Asn Tyr Ile Leu His Ala Val Leu Val His Ser Gly Asp
    445                 450                 455
```

```
aat cat ggt gga cat tat gtg gtt tat cta aac ccc aaa ggg gat ggc      1624
Asn His Gly Gly His Tyr Val Val Tyr Leu Asn Pro Lys Gly Asp Gly
460                 465                 470                 475

aaa tgg tgt aaa ttt gat gac gac gtg gtg tca agg tgt act aaa gag      1672
Lys Trp Cys Lys Phe Asp Asp Asp Val Val Ser Arg Cys Thr Lys Glu
                480                 485                 490

gaa gca att gag cac aat tat ggg ggt cac gat gac gac ctg tct gtt      1720
Glu Ala Ile Glu His Asn Tyr Gly Gly His Asp Asp Asp Leu Ser Val
            495                 500                 505

cga cac tgc act aat gct tac atg tta gtc tac atc agg gaa tca aaa      1768
Arg His Cys Thr Asn Ala Tyr Met Leu Val Tyr Ile Arg Glu Ser Lys
        510                 515                 520

ctg agt gaa gtt tta cag gcg gtc acc gac cat gat att cct cag cag      1816
Leu Ser Glu Val Leu Gln Ala Val Thr Asp His Asp Ile Pro Gln Gln
    525                 530                 535

ttg gtg gag cga tta caa gaa gag aaa agg atc gag gct cag aag cgg      1864
Leu Val Glu Arg Leu Gln Glu Glu Lys Arg Ile Glu Ala Gln Lys Arg
540                 545                 550                 555

aag gag cgg cag gaa gcc cat ctc tat atg caa gtg cag ata gtc gca      1912
Lys Glu Arg Gln Glu Ala His Leu Tyr Met Gln Val Gln Ile Val Ala
                560                 565                 570

gag gac cag ttt tgt ggc cac caa ggg aat gac atg tac gat gaa gaa      1960
Glu Asp Gln Phe Cys Gly His Gln Gly Asn Asp Met Tyr Asp Glu Glu
            575                 580                 585

aaa gtg aaa tac act gtg ttc aaa gta ttg aag aac tcc tcg ctt gct      2008
Lys Val Lys Tyr Thr Val Phe Lys Val Leu Lys Asn Ser Ser Leu Ala
        590                 595                 600

gag ttt gtt cag agc ctc tct cag acc atg gga ttt cca caa gat caa      2056
Glu Phe Val Gln Ser Leu Ser Gln Thr Met Gly Phe Pro Gln Asp Gln
    605                 610                 615

att cga ttg tgg ccc atg caa gca agg agt aat gga aca aaa cga cca      2104
Ile Arg Leu Trp Pro Met Gln Ala Arg Ser Asn Gly Thr Lys Arg Pro
620                 625                 630                 635

gca atg tta gat aat gaa gcc gac ggc aat aaa aca atg att gag ctc      2152
Ala Met Leu Asp Asn Glu Ala Asp Gly Asn Lys Thr Met Ile Glu Leu
                640                 645                 650

agt gat aat gaa aac cct tgg aca ata ttc ctg gaa aca gtt gat ccc      2200
Ser Asp Asn Glu Asn Pro Trp Thr Ile Phe Leu Glu Thr Val Asp Pro
            655                 660                 665

gag ctg gct gct agt gga gcg acc tta ccc aag ttt gat aaa gat cat      2248
Glu Leu Ala Ala Ser Gly Ala Thr Leu Pro Lys Phe Asp Lys Asp His
        670                 675                 680

gat gta atg tta ttt ttg aag atg tat gat ccc aaa acg cgg agc ttg      2296
Asp Val Met Leu Phe Leu Lys Met Tyr Asp Pro Lys Thr Arg Ser Leu
    685                 690                 695

aat tac tgt ggg cat atc tac aca cca ata tcc tgt aaa ata cgt gac      2344
Asn Tyr Cys Gly His Ile Tyr Thr Pro Ile Ser Cys Lys Ile Arg Asp
700                 705                 710                 715

ttg ctc cca gtt atg tgt gac aga gca gga ttt att caa gat act agc      2392
Leu Leu Pro Val Met Cys Asp Arg Ala Gly Phe Ile Gln Asp Thr Ser
                720                 725                 730

ctt atc ctc tat gag gaa gtt aaa ccg aat tta aca gag aga att cag      2440
Leu Ile Leu Tyr Glu Glu Val Lys Pro Asn Leu Thr Glu Arg Ile Gln
            735                 740                 745

gac tat gac gtg tct ctt gat aaa gcc ctt gat gaa cta atg gat ggt      2488
Asp Tyr Asp Val Ser Leu Asp Lys Ala Leu Asp Glu Leu Met Asp Gly
        750                 755                 760

gac atc ata gta ttt cag aag gat gac cct gaa aat gat aac agt gaa      2536
Asp Ile Ile Val Phe Gln Lys Asp Asp Pro Glu Asn Asp Asn Ser Glu
    765                 770                 775
```

```
tta ccc acc gca aag gag tat ttc cga gat ctc tac cac cgc gtt gat     2584
Leu Pro Thr Ala Lys Glu Tyr Phe Arg Asp Leu Tyr His Arg Val Asp
780                 785                 790                 795

gtc att ttc tgt gat aaa aca atc cct aat gat cct gga ttt gtg gtt     2632
Val Ile Phe Cys Asp Lys Thr Ile Pro Asn Asp Pro Gly Phe Val Val
                800                 805                 810

acg tta tca aat aga atg aat tat ttt cag gtt gca aag aca gtt gca     2680
Thr Leu Ser Asn Arg Met Asn Tyr Phe Gln Val Ala Lys Thr Val Ala
            815                 820                 825

cag agg ctc aac aca gat cca atg ttg ctg cag ttt ttc aag tct caa     2728
Gln Arg Leu Asn Thr Asp Pro Met Leu Leu Gln Phe Phe Lys Ser Gln
        830                 835                 840

ggt tat agg gat ggc cca ggt aat cct ctt aga cat aat tat gaa ggt     2776
Gly Tyr Arg Asp Gly Pro Gly Asn Pro Leu Arg His Asn Tyr Glu Gly
    845                 850                 855

act tta aga gat ctt cta cag ttc ttc aag cct aga caa cct aag aaa     2824
Thr Leu Arg Asp Leu Leu Gln Phe Phe Lys Pro Arg Gln Pro Lys Lys
860                 865                 870                 875

ctt tac tat cag cag ctt aag atg aaa atc aca gac ttt gag aac agg     2872
Leu Tyr Tyr Gln Gln Leu Lys Met Lys Ile Thr Asp Phe Glu Asn Arg
                880                 885                 890

cga agt ttt aaa tgt ata tgg tta aac agc caa ttt agg gaa gag gaa     2920
Arg Ser Phe Lys Cys Ile Trp Leu Asn Ser Gln Phe Arg Glu Glu Glu
            895                 900                 905

ata aca cta tat cca gac aag cat ggg tgt gtc cgg gac ctg tta gaa     2968
Ile Thr Leu Tyr Pro Asp Lys His Gly Cys Val Arg Asp Leu Leu Glu
        910                 915                 920

gaa tgt aaa aag gcc gtg gag ctt ggg gag aaa gca tca ggg aaa ctt     3016
Glu Cys Lys Lys Ala Val Glu Leu Gly Glu Lys Ala Ser Gly Lys Leu
    925                 930                 935

agg ctg cta gaa att gta agc tac aaa atc att ggt gtt cat caa gaa     3064
Arg Leu Leu Glu Ile Val Ser Tyr Lys Ile Ile Gly Val His Gln Glu
940                 945                 950                 955

gat gaa cta tta gaa tgt tta tct cct gca acg agc cgg acg ttt cga     3112
Asp Glu Leu Leu Glu Cys Leu Ser Pro Ala Thr Ser Arg Thr Phe Arg
                960                 965                 970

ata gag gaa atc cct ttg gac cag gtg gac ata gac aaa gag aat gag     3160
Ile Glu Glu Ile Pro Leu Asp Gln Val Asp Ile Asp Lys Glu Asn Glu
            975                 980                 985

atg ctt gtc aca gtg gcg cat ttc cac aaa gag gtc ttc  gga acg ttc    3208
Met Leu Val Thr Val Ala His Phe His Lys Glu Val Phe  Gly Thr Phe
        990                 995                 1000

gga atc  ccg ttt ttg ctg agg  ata cac cag ggc gag  cat ttt cga     3253
Gly Ile  Pro Phe Leu Leu Arg  Ile His Gln Gly Glu  His Phe Arg
    1005                 1010                 1015

gaa gtg  atg aag cga atc cag  agc ctg ctg gac atc  cag gag aag     3298
Glu Val  Met Lys Arg Ile Gln  Ser Leu Leu Asp Ile  Gln Glu Lys
    1020                 1025                 1030

gag ttt  gag aag ttt aaa ttt  gca att gta atg atg  ggc cga cac     3343
Glu Phe  Glu Lys Phe Lys Phe  Ala Ile Val Met Met  Gly Arg His
    1035                 1040                 1045

cag tac  ata aat gaa gac gag  tat gaa gta aat ttg  aaa gac ttt     3388
Gln Tyr  Ile Asn Glu Asp Glu  Tyr Glu Val Asn Leu  Lys Asp Phe
    1050                 1055                 1060

gag cca  cag ccc ggt aat atg  tct cat cct cgg cct  tgg cta ggg     3433
Glu Pro  Gln Pro Gly Asn Met  Ser His Pro Arg Pro  Trp Leu Gly
    1065                 1070                 1075

ctc gac  cac ttc aac aaa gcc  cca aag agg agt cgc  tac act tac     3478
Leu Asp  His Phe Asn Lys Ala  Pro Lys Arg Ser Arg  Tyr Thr Tyr
    1080                 1085                 1090
```

```
ctt gaa  aag gcc att aaa atc  cat aac tga tttccaagct ggtgtgttca     3528
Leu Glu  Lys Ala Ile Lys Ile  His Asn
    1095                 1100

aggcgaggac ggtgtgtggg tggcccctta acagcctaga actttggtgc acgtgccctc   3588

tagccgaagt cttcagcaag aggattcgct gctggtgtta attttatttt attgaggctg   3648

ttcagtttgg cttctctgta tctattgact gccctttttg agcaaaatga agatgttttt   3708

ataaagcttg gatgccaatg agagttattt tatggtaacc acagtgcaag gcaactgtca   3768

gcgcaatggg ggagaagagg ttagtggatc gggggtccct ggctcaaggt ctctgggctg   3828

tccctagtgg gcacgagtgg ctcggctgcc ttcctggggt cccgtgcacc agccctgcag   3888

ctagcaagtc ttgtgtttag gctcgtctga cctatttcct tcagttatac tttcaatgac   3948

cttttgtgca tctgttaagg caaaacagag aaactcacaa cctaataaat agcgctcttc   4008

ccttcattgt gtgcattgtc ggcccttcct cgggttctcc tcctccagct gcctgggggc   4068

tttttaataa acttgtctca cctcgtcagc cactactgtc tgcagcccct ttgcaaagtg   4128

gatgcactga atacagtccg gacagacatt gtggggggtct ttttattaaa tcaagaacat  4188

tgttaaattc aattaaggtt tactctgctg ccttggcaga cttacgatct caacagttca   4248

tacgagcagg tgaaaggatt ataaatagaa tttcgttaaa gtggaacaga cgacaagaaa   4308

gccttttagc aagagggcat gctcactagt ggttagtaag ctgtcgactt tgtaaaaaag   4368

ttaaaaatga aaaaaaaagg aaaaatgaat tgtatattta atgaatgaac atgtacaatt   4428

tgccactggg aggaggttcc tttttgttgg gtgagtctgc aagtgaattt cactgatgtt   4488

gatattcatt gtgtgtagtt ttatttcggt cccagccccg tttccttta ttttggagct    4548

aatgccagct gcgtgtctag ttttgagtgc agtaaaatag aatcagcaaa tcactcttat   4608

ttttcatcct tttccggtat tttttgggtt gtttctgtgg gagcagtgta caccaactct   4668

tcctgtatat tgccttttttg ctggaaaatg ttgtatgttg aataaaattt tctataaaaa  4728

ttataattca gtgagttacg tggaagtgga ggaagatttc tactctccct ggaaacaggc   4788

ctgggaaacc ttggcatttg taacaaggtt tcactgagat gtacttttcc ttctaattcc   4848

gttttgcggg ggcagggtct cttgtttctt tttttttttt tttttttttt tagcctctaa   4908

ctagtcacat ttactcttaa gaaatgaaag gttttccagg agagaactgt gtacaaataa   4968

ggtgactgga gatgtgacct gatgtgtcac gaggcccttc ggggcggcag gcgctatcgt   5028

gggcgtggtc cttgcaccgt cccatcggcc ttgccttcca gctccgtggc acggtttcct   5088

ggtctttggg ccagtgtgta ccttggagtg acttcctttc tcaacttcca ctgcagtgtg   5148

tgtgccttct gctctgagag ctgccttgtg acccgtgtga tagaaagcag ggagtgaggg   5208

tccccgcgga cctggccctt ccctccttcc tcccccagaa agaggagtta gagcaggggt   5268

gcgagagccg ttcgctgtgg gtttgtcttt gaacaaacat taaggtgtct tgtttttgtt   5328

ctgggctggg ggttggctgt agtcttaggt aactgaaagt tcctactctc ccttaaggta   5388

ttaaatgact ctttttccaa agaa                                          5412
```

<210> SEQ ID NO 6
<211> LENGTH: 1102
<212> TYPE: PRT
<213> ORGANISM: Homo sapiens

<400> SEQUENCE: 6

```
Met Asn His Gln Gln Gln Gln Gln Gln Gln Lys Ala Gly Glu Gln Gln
1               5                   10                  15
```

```
Leu Ser Glu Pro Glu Asp Met Glu Met Glu Ala Gly Asp Thr Asp Asp
            20                  25                  30

Pro Pro Arg Ile Thr Gln Asn Pro Val Ile Asn Gly Asn Val Ala Leu
        35                  40                  45

Ser Asp Gly His Asn Thr Ala Glu Glu Asp Met Glu Asp Asp Thr Ser
    50                  55                  60

Trp Arg Ser Glu Ala Thr Phe Gln Phe Thr Val Glu Arg Phe Ser Arg
65                  70                  75                  80

Leu Ser Glu Ser Val Leu Ser Pro Pro Cys Phe Val Arg Asn Leu Pro
                85                  90                  95

Trp Lys Ile Met Val Met Pro Arg Phe Tyr Pro Asp Arg Pro His Gln
            100                 105                 110

Lys Ser Val Gly Phe Phe Leu Gln Cys Asn Ala Glu Ser Asp Ser Thr
        115                 120                 125

Ser Trp Ser Cys His Ala Gln Ala Val Leu Lys Ile Ile Asn Tyr Arg
    130                 135                 140

Asp Asp Glu Lys Ser Phe Ser Arg Arg Ile Ser His Leu Phe Phe His
145                 150                 155                 160

Lys Glu Asn Asp Trp Gly Phe Ser Asn Phe Met Ala Trp Ser Glu Val
                165                 170                 175

Thr Asp Pro Glu Lys Gly Phe Ile Asp Asp Asp Lys Val Thr Phe Glu
            180                 185                 190

Val Phe Val Gln Ala Asp Ala Pro His Gly Val Ala Trp Asp Ser Lys
        195                 200                 205

Lys His Thr Gly Tyr Val Gly Leu Lys Asn Gln Gly Ala Thr Cys Tyr
    210                 215                 220

Met Asn Ser Leu Leu Gln Thr Leu Phe Phe Thr Asn Gln Leu Arg Lys
225                 230                 235                 240

Ala Val Tyr Met Met Pro Thr Glu Gly Asp Asp Ser Ser Lys Ser Val
                245                 250                 255

Pro Leu Ala Leu Gln Arg Val Phe Tyr Glu Leu Gln His Ser Asp Lys
            260                 265                 270

Pro Val Gly Thr Lys Lys Leu Thr Lys Ser Phe Gly Trp Glu Thr Leu
        275                 280                 285

Asp Ser Phe Met Gln His Asp Val Gln Glu Leu Cys Arg Val Leu Leu
    290                 295                 300

Asp Asn Val Glu Asn Lys Met Lys Gly Thr Cys Val Glu Gly Thr Ile
305                 310                 315                 320

Pro Lys Leu Phe Arg Gly Lys Met Val Ser Tyr Ile Gln Cys Lys Glu
                325                 330                 335

Val Asp Tyr Arg Ser Asp Arg Arg Glu Asp Tyr Tyr Asp Ile Gln Leu
            340                 345                 350

Ser Ile Lys Gly Lys Lys Asn Ile Phe Glu Ser Phe Val Asp Tyr Val
        355                 360                 365

Ala Val Glu Gln Leu Asp Gly Asp Asn Lys Tyr Asp Ala Gly Glu His
    370                 375                 380

Gly Leu Gln Glu Ala Glu Lys Gly Val Lys Phe Leu Thr Leu Pro Pro
385                 390                 395                 400

Val Leu His Leu Gln Leu Met Arg Phe Met Tyr Asp Pro Gln Thr Asp
                405                 410                 415

Gln Asn Ile Lys Ile Asn Asp Arg Phe Glu Phe Pro Glu Gln Leu Pro
            420                 425                 430

Leu Asp Glu Phe Leu Gln Lys Thr Asp Pro Lys Asp Pro Ala Asn Tyr
        435                 440                 445
```

```
Ile Leu His Ala Val Leu Val His Ser Gly Asp Asn His Gly Gly His
    450                 455                 460

Tyr Val Val Tyr Leu Asn Pro Lys Gly Asp Gly Lys Trp Cys Lys Phe
465                 470                 475                 480

Asp Asp Asp Val Val Ser Arg Cys Thr Lys Glu Glu Ala Ile Glu His
                485                 490                 495

Asn Tyr Gly Gly His Asp Asp Asp Leu Ser Val Arg His Cys Thr Asn
            500                 505                 510

Ala Tyr Met Leu Val Tyr Ile Arg Glu Ser Lys Leu Ser Glu Val Leu
        515                 520                 525

Gln Ala Val Thr Asp His Asp Ile Pro Gln Gln Leu Val Glu Arg Leu
    530                 535                 540

Gln Glu Glu Lys Arg Ile Glu Ala Gln Lys Arg Lys Glu Arg Gln Glu
545                 550                 555                 560

Ala His Leu Tyr Met Gln Val Gln Ile Val Ala Glu Asp Gln Phe Cys
                565                 570                 575

Gly His Gln Gly Asn Asp Met Tyr Asp Glu Glu Lys Val Lys Tyr Thr
            580                 585                 590

Val Phe Lys Val Leu Lys Asn Ser Ser Leu Ala Glu Phe Val Gln Ser
        595                 600                 605

Leu Ser Gln Thr Met Gly Phe Pro Gln Asp Gln Ile Arg Leu Trp Pro
    610                 615                 620

Met Gln Ala Arg Ser Asn Gly Thr Lys Arg Pro Ala Met Leu Asp Asn
625                 630                 635                 640

Glu Ala Asp Gly Asn Lys Thr Met Ile Glu Leu Ser Asp Asn Glu Asn
                645                 650                 655

Pro Trp Thr Ile Phe Leu Glu Thr Val Asp Pro Glu Leu Ala Ala Ser
            660                 665                 670

Gly Ala Thr Leu Pro Lys Phe Asp Lys Asp His Asp Val Met Leu Phe
        675                 680                 685

Leu Lys Met Tyr Asp Pro Lys Thr Arg Ser Leu Asn Tyr Cys Gly His
    690                 695                 700

Ile Tyr Thr Pro Ile Ser Cys Lys Ile Arg Asp Leu Leu Pro Val Met
705                 710                 715                 720

Cys Asp Arg Ala Gly Phe Ile Gln Asp Thr Ser Leu Ile Leu Tyr Glu
                725                 730                 735

Glu Val Lys Pro Asn Leu Thr Glu Arg Ile Gln Asp Tyr Asp Val Ser
            740                 745                 750

Leu Asp Lys Ala Leu Asp Glu Leu Met Asp Gly Asp Ile Ile Val Phe
        755                 760                 765

Gln Lys Asp Asp Pro Glu Asn Asp Asn Ser Glu Leu Pro Thr Ala Lys
    770                 775                 780

Glu Tyr Phe Arg Asp Leu Tyr His Arg Val Asp Val Ile Phe Cys Asp
785                 790                 795                 800

Lys Thr Ile Pro Asn Asp Pro Gly Phe Val Val Thr Leu Ser Asn Arg
                805                 810                 815

Met Asn Tyr Phe Gln Val Ala Lys Thr Val Ala Gln Arg Leu Asn Thr
            820                 825                 830

Asp Pro Met Leu Leu Gln Phe Phe Lys Ser Gln Gly Tyr Arg Asp Gly
        835                 840                 845

Pro Gly Asn Pro Leu Arg His Asn Tyr Glu Gly Thr Leu Arg Asp Leu
    850                 855                 860

Leu Gln Phe Phe Lys Pro Arg Gln Pro Lys Lys Leu Tyr Tyr Gln Gln
```

-continued

```
865                 870                 875                 880

Leu Lys Met Lys Ile Thr Asp Phe Glu Asn Arg Arg Ser Phe Lys Cys
                885                 890                 895

Ile Trp Leu Asn Ser Gln Phe Arg Glu Glu Ile Thr Leu Tyr Pro
            900                 905                 910

Asp Lys His Gly Cys Val Arg Asp Leu Leu Glu Glu Cys Lys Lys Ala
        915                 920                 925

Val Glu Leu Gly Glu Lys Ala Ser Gly Lys Leu Arg Leu Leu Glu Ile
    930                 935                 940

Val Ser Tyr Lys Ile Ile Gly Val His Gln Glu Asp Glu Leu Leu Glu
945                 950                 955                 960

Cys Leu Ser Pro Ala Thr Ser Arg Thr Phe Arg Ile Glu Glu Ile Pro
                965                 970                 975

Leu Asp Gln Val Asp Ile Asp Lys Glu Asn Glu Met Leu Val Thr Val
            980                 985                 990

Ala His Phe His Lys Glu Val Phe  Gly Thr Phe Gly Ile  Pro Phe Leu
        995                 1000                1005

Leu Arg  Ile His Gln Gly Glu  His Phe Arg Glu Val  Met Lys Arg
    1010                1015                1020

Ile Gln  Ser Leu Leu Asp Ile  Gln Glu Lys Glu Phe  Glu Lys Phe
    1025                1030                1035

Lys Phe  Ala Ile Val Met Met  Gly Arg His Gln Tyr  Ile Asn Glu
    1040                1045                1050

Asp Glu  Tyr Glu Val Asn Leu  Lys Asp Phe Glu Pro  Gln Pro Gly
    1055                1060                1065

Asn Met  Ser His Pro Arg Pro  Trp Leu Gly Leu Asp  His Phe Asn
    1070                1075                1080

Lys Ala  Pro Lys Arg Ser Arg  Tyr Thr Tyr Leu Glu  Lys Ala Ile
    1085                1090                1095

Lys Ile  His Asn
    1100


<210> SEQ ID NO 7
<211> LENGTH: 1675
<212> TYPE: DNA
<213> ORGANISM: Homo sapiens
<220> FEATURE:
<221> NAME/KEY: CDS
<222> LOCATION: (1005)..(1208)

<400> SEQUENCE: 7

acagcaatca aatcagtgac tgccagggac tgggaggtgg gggtgataga tatattctac      60

ttcttaaaaa aaaaaaatca aagtatatat cctaaaacag tgattttact gtatgtaaat     120

tacactccca gaaacctttt ttttaattaa gtattatttc aaaattctgt ttttggacaa     180

aaccaagagc cattccaaaa cgttcaagac cgtcagcact gatagatgtt gaagcaattt     240

actcagtcac aatttaacaa acagctatat aaaatcaaag ctaaccactg aggcactatt     300

taaccatgtt tcccttttttt cagtaagact ggactattat tattacagtt cctcattccc     360

taaagttagc gtttcttttc accactttgt taccagttct caaattactg tcccaaaaaa     420

ctgtagtcta ctcaagaaat ctcacaagga gatatttttt cctacaagat gctgcggcca     480

tttgcacatt cttatgcaaa aattaacaac ttgacagtca agcagcacct tcatagcccg     540

tttcaaccta tatatggcct aaatatatat ggcaaaaata ccaatattgg tatttttgaa     600

atgcacaaag ttccattact gttctgagca acttttaaaa gtctgaaaac atttaattac     660
```

```
atatttctta agattaacaa agtcaaatcc tttttccata aaaatcttgc caaaaaaaaa     720

aatcaacccc aaatttctca atcttcaaaa ccagtaaggc acaaaatcta aacccaccgt     780

taccaagaat gcacaaatgg gcaagaacgt ttacttacac atcttcatgt catcacaaag     840

ggaggggat taactccaga aaggaaccac cataaaacaa acctatggac tcaaaactct     900

caacagaatt cctgccagca acctataatc aaatatagga tccttttaac agaaaacact     960

tgatcaaatt gctagagaag agcagcacgt taacatgcgc gcag atg act ccg att    1016
                                                 Met Thr Pro Ile
                                                 1

agc aag ctt tca agc act tca aaa cta tat aga ctg cca cgc ttt caa     1064
Ser Lys Leu Ser Ser Thr Ser Lys Leu Tyr Arg Leu Pro Arg Phe Gln
5                   10                  15                  20

atg cct aac tca aga atc ttt tcc ata aag ttc gtc cca ctt ccg act     1112
Met Pro Asn Ser Arg Ile Phe Ser Ile Lys Phe Val Pro Leu Pro Thr
                25                  30                  35

gta gta caa aaa aca tca act ctt atc ttc cct caa tgt ctt ttc cag     1160
Val Val Gln Lys Thr Ser Thr Leu Ile Phe Pro Gln Cys Leu Phe Gln
            40                  45                  50

agg gag gca agg ctc agc cgt ctt cca gct caa cgc ttc tca acc tga     1208
Arg Glu Ala Arg Leu Ser Arg Leu Pro Ala Gln Arg Phe Ser Thr
        55                  60                  65

gcactactga ctttaggggc aggataattc ttcgctgaga gggggccggg gcggttatct    1268

tgggcactgc aggaccttca gcagcctcta tacactgggt gcccaacaac agccccttct    1328

aggagaagcc aaccaaaaac gtccccaggc gttgccatct gtcccggggg gcggagggag    1388

gtgtcaaaat cgcctccggt ggatctagct agagcaccgc cgcgattctc aagttgcaag    1448

gtattcaagg ttagcagctg ggctggggag cagaaaacac acttggaacg cagggcagac    1508

accctgacgc aggcggccct tccctgaatc ggcaatgcag caaggttatc tttacctttg    1568

tagagattgg tgacggcggt ggctgcgttt tggaagggga cccagagaga aagtcctggc    1628

tgctgacaca ctcggtctga aaagcaagcc aaaaaaaaaa aaaaaaa                  1675


<210> SEQ ID NO 8
<211> LENGTH: 67
<212> TYPE: PRT
<213> ORGANISM: Homo sapiens

<400> SEQUENCE: 8

Met Thr Pro Ile Ser Lys Leu Ser Ser Thr Ser Lys Leu Tyr Arg Leu
1               5                   10                  15

Pro Arg Phe Gln Met Pro Asn Ser Arg Ile Phe Ser Ile Lys Phe Val
            20                  25                  30

Pro Leu Pro Thr Val Val Gln Lys Thr Ser Thr Leu Ile Phe Pro Gln
        35                  40                  45

Cys Leu Phe Gln Arg Glu Ala Arg Leu Ser Arg Leu Pro Ala Gln Arg
    50                  55                  60

Phe Ser Thr
65


<210> SEQ ID NO 9
<211> LENGTH: 2540
<212> TYPE: DNA
<213> ORGANISM: Homo sapiens
<220> FEATURE:
<221> NAME/KEY: CDS
<222> LOCATION: (287)..(736)

<400> SEQUENCE: 9
```

```
attgggctgt tgagcggggg ccgaccgacg gccaggagtt tcttttctgc gcttgtgcgt     60

tttctgttcg gtttccttcc cgctagcggg gccacgaggg ttgctaggca acagcccctg    120

ggtgacttgg tcttagggtc ctgtccggct tggggctgat gaaaggagct gtccgcgccc    180

gggctcttcc gagaagtggt tgctgacagc cacaaagtga aagggagtga ggcggcgtgg    240

acgagtaagg agtgacagtg aggattcaca tttgggttat ttcaag atg agc ttc       295
                                                    Met Ser Phe
                                                    1

cta ctg ccc aag ctg act agc aaa aag gaa gta gac cag gcg ata aaa      343
Leu Leu Pro Lys Leu Thr Ser Lys Lys Glu Val Asp Gln Ala Ile Lys
    5                   10                  15

agt act gct gag aag gtg ttg gtt ctc agg ttt ggg aga gat gaa gat      391
Ser Thr Ala Glu Lys Val Leu Val Leu Arg Phe Gly Arg Asp Glu Asp
20                  25                  30                  35

cct gtc tgt ctg cag cta gat gat att ctt tct aag acc tct tct gac      439
Pro Val Cys Leu Gln Leu Asp Asp Ile Leu Ser Lys Thr Ser Ser Asp
                40                  45                  50

tta agt aaa atg gct gct ata tac ctg gtg gat gtg gac caa act gca      487
Leu Ser Lys Met Ala Ala Ile Tyr Leu Val Asp Val Asp Gln Thr Ala
            55                  60                  65

gtt tat aca cag tat ttt gac atc agt tat att cca tct act gtc ttt      535
Val Tyr Thr Gln Tyr Phe Asp Ile Ser Tyr Ile Pro Ser Thr Val Phe
        70                  75                  80

ttc ttc aat ggg cag cat atg aaa gtg gat tat gga tct cca gat cac      583
Phe Phe Asn Gly Gln His Met Lys Val Asp Tyr Gly Ser Pro Asp His
    85                  90                  95

act aag ttt gtg gga agc ttc aaa acc aaa caa gac ttc ata gat ttg      631
Thr Lys Phe Val Gly Ser Phe Lys Thr Lys Gln Asp Phe Ile Asp Leu
100                 105                 110                 115

att gaa gta atc tat cga gga gca atg agg ggg aag ctt att gtc caa      679
Ile Glu Val Ile Tyr Arg Gly Ala Met Arg Gly Lys Leu Ile Val Gln
                120                 125                 130

agt cct att gat ccc aag aat att ccc aaa tat gac ctt ctc tat caa      727
Ser Pro Ile Asp Pro Lys Asn Ile Pro Lys Tyr Asp Leu Leu Tyr Gln
            135                 140                 145

gac att tag tacattaatt gctgtcaaag atgaagaaga aggcacatct              776
Asp Ile

tgacacagta cctgaatcca gctgtgctgt gtttctggag tcctttggaa acatgtgtcc    836

cagaggagaa gaggtttgac ttgcgtgtag aaaacccggc ccctgaggaa aagaccccac    896

tggttctctg atgacctggg atgcctaact gtctactccc tgcaagcctc agagcagcca    956

agtcattggt gttcattttc cccacagtga tttttgtaac ttctctttct aatgtttttc   1016

tttatccctt taatacagaa ccctcccaaa cattggctag tacaacttga tttcatcatg   1076

ttcatttgat acacaagtga actggaaagt cacttcccat agaagcaaaa gtacttattt   1136

tctaccctag ctgggtgcat gtgtgtgcac acacacacac acacacaccc ccacacccct   1196

ttgccggttc ctcgactcat acatccctcg tgctttccca tctccagtct gtattactgt   1256

aggttctctt caaataatta attgagcaga caagtttgtt ttattttgga gccttttggg   1316

ctctggcttt taaacattgt cctggttggc tcatttaatt tttttttttt ttttgagacc   1376

gagtcactct tgtcacccag gctggagtgc agtggcgcga tctcggctca ctgcaagctc   1436

cacctcctgg gttcatgcca ttctcctgct tcagcctcct gagtagctgg gactacaggc   1496

gcccgccacc atgcccagct aattttttgt atttttatag aggcgcagtt tcaccgtgtt   1556

agccaagatg gtctcgatct cctgacctcg tgatctgccc tcctcagcct cccaggtgct   1616

gggattatag gcgtgagcca ccgcgcgcac cccatttaat tattttttat gttataaaat   1676
```

```
ttaatatgga aagtgagaat ttgaaccttc accatccacc actctattca ggtaaaacaa   1736

tgaatgagcc accttagcag gagcagattt ttcccagaag ctgctgcctc ttcctgaggc   1796

agaaaattgg attactaagg ctcaaaacta aaagagatgt cagcattgtt ggatagaaat   1856

gtcacctata tgggatttgc ctgttttaat aactttgtaa ggaattcttg ctcttctagg   1916

ggtgcctggc gcaaccgtgg gcaagttact gctcctcttt aaacctcgtg gtggttattg   1976

aaacagattt attagaagga gagggtaggt gcagagctgg agagccatgg gtgaggcagc   2036

ttgtgacctg cctagcagcc gctgaccacc tctccaacag aagcctagtc ctgttcagag   2096

cagcactgtc actgcaagtc cagcccccctt tgccaggggc tccattccac ccctttcctg   2156

cagggagggg tgccatgagt cttgcttttg gctcatacag gagagaggga aggctgccag   2216

gcactgcttg tatccctgct gataagagga gggagtcact ccaggaataa gacaaaagga   2276

gaggaggagg ccatcacctc tggcctcttc catcgtacac ttcctgtctc tggtttaatc   2336

atgatgcatg gagctacaac agccatctta ggtccccgag gtgcccagca tcacgtaaaa   2396

catcgatatg ctaagaagaa caaaaagagc ccaatctctg atgttattga gctcctgcat   2456

gaactctgga cctgcctgcc tcagacttct gtgaaagaat aaaatttctt tttgcctaaa   2516

aaaaaaaaaa aaaaaaaaaa aaaa                                          2540
```

<210> SEQ ID NO 10
<211> LENGTH: 149
<212> TYPE: PRT
<213> ORGANISM: Homo sapiens

<400> SEQUENCE: 10

```
Met Ser Phe Leu Leu Pro Lys Leu Thr Ser Lys Lys Glu Val Asp Gln
1               5                   10                  15

Ala Ile Lys Ser Thr Ala Glu Lys Val Leu Val Leu Arg Phe Gly Arg
            20                  25                  30

Asp Glu Asp Pro Val Cys Leu Gln Leu Asp Asp Ile Leu Ser Lys Thr
        35                  40                  45

Ser Ser Asp Leu Ser Lys Met Ala Ala Ile Tyr Leu Val Asp Val Asp
    50                  55                  60

Gln Thr Ala Val Tyr Thr Gln Tyr Phe Asp Ile Ser Tyr Ile Pro Ser
65                  70                  75                  80

Thr Val Phe Phe Phe Asn Gly Gln His Met Lys Val Asp Tyr Gly Ser
                85                  90                  95

Pro Asp His Thr Lys Phe Val Gly Ser Phe Lys Thr Lys Gln Asp Phe
            100                 105                 110

Ile Asp Leu Ile Glu Val Ile Tyr Arg Gly Ala Met Arg Gly Lys Leu
        115                 120                 125

Ile Val Gln Ser Pro Ile Asp Pro Lys Asn Ile Pro Lys Tyr Asp Leu
    130                 135                 140

Leu Tyr Gln Asp Ile
145
```

<210> SEQ ID NO 11
<211> LENGTH: 3779
<212> TYPE: DNA
<213> ORGANISM: Homo sapiens
<220> FEATURE:
<221> NAME/KEY: CDS
<222> LOCATION: (26)..(3637)

<400> SEQUENCE: 11

```
gcgtcgagct cgccgcggac tcaag atg gcg gcg tgt gga cgt gta cgg agg        52
                            Met Ala Ala Cys Gly Arg Val Arg Arg
                            1               5

atg ttc cgc ttg tcg gcg gcg ctg cat ctg ctg ctg cta ttc gcg gcc       100
Met Phe Arg Leu Ser Ala Ala Leu His Leu Leu Leu Leu Phe Ala Ala
10                  15                  20                  25

ggg gcc gag aaa ctc ccc ggc cag ggc gtc cac agc cag ggc cag ggt       148
Gly Ala Glu Lys Leu Pro Gly Gln Gly Val His Ser Gln Gly Gln Gly
                30                  35                  40

ccc ggg gcc aac ttt gtg tcc ttc gta ggg cag gcc gga ggc ggc ggc       196
Pro Gly Ala Asn Phe Val Ser Phe Val Gly Gln Ala Gly Gly Gly Gly
            45                  50                  55

ccg gcg ggt cag cag ctg ccc cag ctg cct cag tca tcg cag ctt cag       244
Pro Ala Gly Gln Gln Leu Pro Gln Leu Pro Gln Ser Ser Gln Leu Gln
        60                  65                  70

cag caa cag cag cag cag caa cag caa cag cag cct cag ccg ccg cag       292
Gln Gln Gln Gln Gln Gln Gln Gln Gln Gln Gln Pro Gln Pro Pro Gln
    75                  80                  85

ccg cct ttc ccg gcg ggt ggg cct ccg gcc cgg cgg gga gga gcg ggg       340
Pro Pro Phe Pro Ala Gly Gly Pro Pro Ala Arg Arg Gly Gly Ala Gly
90                  95                  100                 105

gct ggt ggg ggc tgg aag ctg gcg gag gaa gag tcc tgc agg gag gac       388
Ala Gly Gly Gly Trp Lys Leu Ala Glu Glu Glu Ser Cys Arg Glu Asp
                110                 115                 120

gtg acc cgc gtg tgc cct aag cac acc tgg agc aac aac ctg gcg gtg       436
Val Thr Arg Val Cys Pro Lys His Thr Trp Ser Asn Asn Leu Ala Val
            125                 130                 135

ctc gag tgc ctg cag gat gtg agg gag cct gaa aat gaa att tct tca       484
Leu Glu Cys Leu Gln Asp Val Arg Glu Pro Glu Asn Glu Ile Ser Ser
        140                 145                 150

gac tgc aat cat ttg ttg tgg aat tat aag ctg aac cta act aca gat       532
Asp Cys Asn His Leu Leu Trp Asn Tyr Lys Leu Asn Leu Thr Thr Asp
    155                 160                 165

ccc aaa ttt gaa tct gtg gcc aga gag gtt tgc aaa tct act ata aca       580
Pro Lys Phe Glu Ser Val Ala Arg Glu Val Cys Lys Ser Thr Ile Thr
170                 175                 180                 185

gag att aaa gaa tgt gct gat gaa ccg gtt gga aaa ggt tac atg gtt       628
Glu Ile Lys Glu Cys Ala Asp Glu Pro Val Gly Lys Gly Tyr Met Val
                190                 195                 200

tcc tgc ttg gtg gat cac cga ggc aac atc act gag tat cag tgt cac       676
Ser Cys Leu Val Asp His Arg Gly Asn Ile Thr Glu Tyr Gln Cys His
            205                 210                 215

cag tac att acc aag atg acg gcc atc att ttt agt gat tac cgt tta       724
Gln Tyr Ile Thr Lys Met Thr Ala Ile Ile Phe Ser Asp Tyr Arg Leu
        220                 225                 230

atc tgt ggc ttc atg gat gac tgc aaa aat gac atc aac att ctg aaa       772
Ile Cys Gly Phe Met Asp Asp Cys Lys Asn Asp Ile Asn Ile Leu Lys
    235                 240                 245

tgt ggc agt att cgg ctt gga gaa aag gat gca cat tca caa ggt gag       820
Cys Gly Ser Ile Arg Leu Gly Glu Lys Asp Ala His Ser Gln Gly Glu
250                 255                 260                 265

gtg gta tca tgc ttg gag aaa ggc ctg gtg aaa gaa gca gaa gaa aga       868
Val Val Ser Cys Leu Glu Lys Gly Leu Val Lys Glu Ala Glu Glu Arg
                270                 275                 280

gaa ccc aag att caa gtt tct gaa ctc tgc aag aaa gcc att ctc cgg       916
Glu Pro Lys Ile Gln Val Ser Glu Leu Cys Lys Lys Ala Ile Leu Arg
            285                 290                 295

gtg gct gag ctg tca tcg gat gac ttt cac tta gac cgg cat tta tat       964
Val Ala Glu Leu Ser Ser Asp Asp Phe His Leu Asp Arg His Leu Tyr
        300                 305                 310
```

```
ttt gct tgc cga gat gat cgg gag cgt ttt tgt gaa aat aca caa gct      1012
Phe Ala Cys Arg Asp Asp Arg Glu Arg Phe Cys Glu Asn Thr Gln Ala
    315                 320                 325

ggt gag ggc aga gtg tat aag tgc ctc ttt aac cat aaa ttt gaa gaa      1060
Gly Glu Gly Arg Val Tyr Lys Cys Leu Phe Asn His Lys Phe Glu Glu
330                 335                 340                 345

tcc atg agt gaa aag tgt cga gaa gca ctt aca acc cgc caa aag ctg      1108
Ser Met Ser Glu Lys Cys Arg Glu Ala Leu Thr Thr Arg Gln Lys Leu
                350                 355                 360

att gcc cag gat tat aaa gtc agt tat tca ttg gcc aaa tcc tgt aaa      1156
Ile Ala Gln Asp Tyr Lys Val Ser Tyr Ser Leu Ala Lys Ser Cys Lys
            365                 370                 375

agt gac ttg aag aaa tac cgg tgc aat gtg gaa aac ctt ccg cga tcg      1204
Ser Asp Leu Lys Lys Tyr Arg Cys Asn Val Glu Asn Leu Pro Arg Ser
        380                 385                 390

cgt gaa gcc agg ctc tcc tac ttg tta atg tgc ctg gag tca gct gta      1252
Arg Glu Ala Arg Leu Ser Tyr Leu Leu Met Cys Leu Glu Ser Ala Val
    395                 400                 405

cac aga ggg cga caa gtc agc agt gag tgc cag ggg gag atg ctg gat      1300
His Arg Gly Arg Gln Val Ser Ser Glu Cys Gln Gly Glu Met Leu Asp
410                 415                 420                 425

tac cga cgc atg ttg atg gaa gac ttt tct ctg agc cct gag atc atc      1348
Tyr Arg Arg Met Leu Met Glu Asp Phe Ser Leu Ser Pro Glu Ile Ile
                430                 435                 440

cta agc tgt cgg ggg gag att gaa cac cat tgt tcc gga tta cat cga      1396
Leu Ser Cys Arg Gly Glu Ile Glu His His Cys Ser Gly Leu His Arg
            445                 450                 455

aaa ggg cgg acc cta cac tgt ctg atg aaa gta gtt cga ggg gag aag      1444
Lys Gly Arg Thr Leu His Cys Leu Met Lys Val Val Arg Gly Glu Lys
        460                 465                 470

ggg aac ctt gga atg aac tgc cag cag gcg ctt caa aca ctg att cag      1492
Gly Asn Leu Gly Met Asn Cys Gln Gln Ala Leu Gln Thr Leu Ile Gln
    475                 480                 485

gag act gac cct ggt gca gat tac cgc att gat cga gct ttg aat gaa      1540
Glu Thr Asp Pro Gly Ala Asp Tyr Arg Ile Asp Arg Ala Leu Asn Glu
490                 495                 500                 505

gct tgt gaa tct gta atc cag aca gcc tgc aaa cat ata aga tct gga      1588
Ala Cys Glu Ser Val Ile Gln Thr Ala Cys Lys His Ile Arg Ser Gly
                510                 515                 520

gac cca atg atc ttg tcg tgc ctg atg gaa cat tta tac aca gag aag      1636
Asp Pro Met Ile Leu Ser Cys Leu Met Glu His Leu Tyr Thr Glu Lys
            525                 530                 535

atg gta gaa gac tgt gaa cac cgt ctc tta gag ctg cag tat ttc atc      1684
Met Val Glu Asp Cys Glu His Arg Leu Leu Glu Leu Gln Tyr Phe Ile
        540                 545                 550

tcc cgg gat tgg aag ctg gac cct gtc ctg tac cgc aag tgc cag gga      1732
Ser Arg Asp Trp Lys Leu Asp Pro Val Leu Tyr Arg Lys Cys Gln Gly
    555                 560                 565

gac gct tct cgt ctt tgc cac acc cac ggt tgg aat gag acc agt gaa      1780
Asp Ala Ser Arg Leu Cys His Thr His Gly Trp Asn Glu Thr Ser Glu
570                 575                 580                 585

ttt atg cct cag gga gct gtg ttc tct tgt tta tac aga cac gcc tac      1828
Phe Met Pro Gln Gly Ala Val Phe Ser Cys Leu Tyr Arg His Ala Tyr
                590                 595                 600

cgc act gag gaa cag gga agg agg ctc tca cgg gag tgc cga gct gaa      1876
Arg Thr Glu Glu Gln Gly Arg Arg Leu Ser Arg Glu Cys Arg Ala Glu
            605                 610                 615

gtc caa agg atc cta cac cag cgt gcc atg gat gtc aag ctg gat cct      1924
Val Gln Arg Ile Leu His Gln Arg Ala Met Asp Val Lys Leu Asp Pro
        620                 625                 630
```

```
gcc ctc cag gat aag tgc ctg att gat ctg gga aaa tgg tgc agt gag      1972
Ala Leu Gln Asp Lys Cys Leu Ile Asp Leu Gly Lys Trp Cys Ser Glu
    635                 640                 645

aaa aca gag act gga cag gag ctg gag tgc ctt cag gac cat ctg gat      2020
Lys Thr Glu Thr Gly Gln Glu Leu Glu Cys Leu Gln Asp His Leu Asp
650                 655                 660                 665

gac ttg gtg gtg gag tgt aga gat ata gtt ggc aac ctc act gag tta      2068
Asp Leu Val Val Glu Cys Arg Asp Ile Val Gly Asn Leu Thr Glu Leu
                670                 675                 680

gaa tca gag gat att caa ata gaa gcc ttg ctg atg aga gcc tgt gag      2116
Glu Ser Glu Asp Ile Gln Ile Glu Ala Leu Leu Met Arg Ala Cys Glu
            685                 690                 695

ccc ata att cag aac ttc tgc cac gat gtg gca gat aac cag ata gac      2164
Pro Ile Ile Gln Asn Phe Cys His Asp Val Ala Asp Asn Gln Ile Asp
        700                 705                 710

tct ggg gac ctg atg gag tgt ctg ata cag aac aaa cac cag aag gac      2212
Ser Gly Asp Leu Met Glu Cys Leu Ile Gln Asn Lys His Gln Lys Asp
    715                 720                 725

atg aac gag aag tgt gcc atc gga gtt acc cac ttc cag ctg gtg cag      2260
Met Asn Glu Lys Cys Ala Ile Gly Val Thr His Phe Gln Leu Val Gln
730                 735                 740                 745

atg aag gat ttt cgg ttt tct tac aag ttt aaa atg gcc tgc aag gag      2308
Met Lys Asp Phe Arg Phe Ser Tyr Lys Phe Lys Met Ala Cys Lys Glu
                750                 755                 760

gac gtg ttg aag ctt tgc cca aac ata aaa aag aag gtg gac gtg gtg      2356
Asp Val Leu Lys Leu Cys Pro Asn Ile Lys Lys Lys Val Asp Val Val
            765                 770                 775

atc tgc ctg agc acg acc gtg cgc aat gac act ctg cag gaa gcc aag      2404
Ile Cys Leu Ser Thr Thr Val Arg Asn Asp Thr Leu Gln Glu Ala Lys
        780                 785                 790

gag cac agg gtg tcc ctg aag tgc cgc agg cag ctc cgt gtg gag gag      2452
Glu His Arg Val Ser Leu Lys Cys Arg Arg Gln Leu Arg Val Glu Glu
    795                 800                 805

ctg gag atg acg gag gac atc cgc ttg gag cca gat cta tac gaa gcc      2500
Leu Glu Met Thr Glu Asp Ile Arg Leu Glu Pro Asp Leu Tyr Glu Ala
810                 815                 820                 825

tgc aag agt gac atc aaa aac ttc tgt tcc gct gtg caa tat ggc aac      2548
Cys Lys Ser Asp Ile Lys Asn Phe Cys Ser Ala Val Gln Tyr Gly Asn
                830                 835                 840

gct cag att atc gaa tgt ctg aaa gaa aac aag aag cag cta agc acc      2596
Ala Gln Ile Ile Glu Cys Leu Lys Glu Asn Lys Lys Gln Leu Ser Thr
            845                 850                 855

cgc tgc cac caa aaa gta ttt aag ctg cag gag aca gag atg atg gac      2644
Arg Cys His Gln Lys Val Phe Lys Leu Gln Glu Thr Glu Met Met Asp
        860                 865                 870

cca gag cta gac tac acc ctc atg agg gtc tgc aag cag atg ata aag      2692
Pro Glu Leu Asp Tyr Thr Leu Met Arg Val Cys Lys Gln Met Ile Lys
    875                 880                 885

agg ttc tgt ccg gaa gca gat tct aaa acc atg ttg cag tgc ttg aag      2740
Arg Phe Cys Pro Glu Ala Asp Ser Lys Thr Met Leu Gln Cys Leu Lys
890                 895                 900                 905

caa aat aaa aac agt gaa ttg atg gat ccc aaa tgc aaa cag atg ata      2788
Gln Asn Lys Asn Ser Glu Leu Met Asp Pro Lys Cys Lys Gln Met Ile
                910                 915                 920

acc aag cgc cag atc acc cag aac aca gat tac cgc tta aac ccc atg      2836
Thr Lys Arg Gln Ile Thr Gln Asn Thr Asp Tyr Arg Leu Asn Pro Met
            925                 930                 935

tta aga aaa gcc tgt aaa gct gac att cct aaa ttc tgt cac ggt atc      2884
Leu Arg Lys Ala Cys Lys Ala Asp Ile Pro Lys Phe Cys His Gly Ile
        940                 945                 950
```

```
ctg act aag gcc aag gat gat tca gaa tta gaa gga caa gtc atc tct      2932
Leu Thr Lys Ala Lys Asp Asp Ser Glu Leu Glu Gly Gln Val Ile Ser
    955                 960                 965

tgc ctg aag ctg aga tat gct gac cag cgc ctg tct tca gac tgt gaa      2980
Cys Leu Lys Leu Arg Tyr Ala Asp Gln Arg Leu Ser Ser Asp Cys Glu
970                 975                 980                 985

gac cag atc cga atc att atc cag gag tcc gcc ctg gac tac cgc  ctg     3028
Asp Gln Ile Arg Ile Ile Ile Gln Glu Ser Ala Leu Asp Tyr Arg  Leu
                990                 995                 1000

gat cct cag ctc  cag ctg cac tgc tca  gac gag atc tcc agt  cta       3073
Asp Pro Gln Leu  Gln Leu His Cys Ser  Asp Glu Ile Ser Ser  Leu
            1005                 1010                 1015

tgt gct gaa gaa  gca gca gcc caa gag  cag aca ggt cag gtg  gag       3118
Cys Ala Glu Glu  Ala Ala Ala Gln Glu  Gln Thr Gly Gln Val  Glu
            1020                 1025                 1030

gag tgc ctc aag  gtc aac ctg ctc aag  atc aaa aca gaa ttg  tgt       3163
Glu Cys Leu Lys  Val Asn Leu Leu Lys  Ile Lys Thr Glu Leu  Cys
            1035                 1040                 1045

aaa aag gaa gtg  cta aac atg ctg aag  gaa agc aaa gca gac  atc       3208
Lys Lys Glu Val  Leu Asn Met Leu Lys  Glu Ser Lys Ala Asp  Ile
            1050                 1055                 1060

ttt gtt gac ccg  gta ctt cat act gct  tgt gcc ctg gac att  aaa       3253
Phe Val Asp Pro  Val Leu His Thr Ala  Cys Ala Leu Asp Ile  Lys
            1065                 1070                 1075

cac cac tgc gca  gcc atc acc cct ggc  cgc ggg cgt caa atg  tcc       3298
His His Cys Ala  Ala Ile Thr Pro Gly  Arg Gly Arg Gln Met  Ser
            1080                 1085                 1090

tgt ctc atg gaa  gca ctg gag gat aag  cgg gtg agg tta cag  ccc       3343
Cys Leu Met Glu  Ala Leu Glu Asp Lys  Arg Val Arg Leu Gln  Pro
            1095                 1100                 1105

gag tgc aaa aag  cgc ctc aat gac cgg  att gag atg tgg agt  tac       3388
Glu Cys Lys Lys  Arg Leu Asn Asp Arg  Ile Glu Met Trp Ser  Tyr
            1110                 1115                 1120

gca gca aag gtg  gcc cca gca gat ggc  ttc tct gat ctt gcc  atg       3433
Ala Ala Lys Val  Ala Pro Ala Asp Gly  Phe Ser Asp Leu Ala  Met
            1125                 1130                 1135

caa gta atg acg  tct cca tct aag aac  tac att ctc tct gtg  atc       3478
Gln Val Met Thr  Ser Pro Ser Lys Asn  Tyr Ile Leu Ser Val  Ile
            1140                 1145                 1150

agt ggg agc atc  tgt ata ttg ttc ctg  att ggc ctg atg tgt  gga       3523
Ser Gly Ser Ile  Cys Ile Leu Phe Leu  Ile Gly Leu Met Cys  Gly
            1155                 1160                 1165

cgg atc acc aag  cga gtg aca cga gag  ctc aag gac agg cta  caa       3568
Arg Ile Thr Lys  Arg Val Thr Arg Glu  Leu Lys Asp Arg Leu  Gln
            1170                 1175                 1180

tac agg tca gag  aca atg gct tat aaa  ggt tta gtg tgg tct  cag       3613
Tyr Arg Ser Glu  Thr Met Ala Tyr Lys  Gly Leu Val Trp Ser  Gln
            1185                 1190                 1195

gat gtg aca ggc  agt cca gcc tga cctttctgca cactccagac aaacttccca    3667
Asp Val Thr Gly  Ser Pro Ala
            1200

gacaagctcc tttgtgcctc tacgtggaga gggtgtggaa agttatcaca ttaaaagatg    3727

gaggatttaa aaaaaaaaaa aaaaaaaaaa aaaaaagaaa aaaaaaaaaa aa            3779
```

<210> SEQ ID NO 12
<211> LENGTH: 1203
<212> TYPE: PRT
<213> ORGANISM: Homo sapiens

<400> SEQUENCE: 12

```
Met Ala Ala Cys Gly Arg Val Arg Arg Met Phe Arg Leu Ser Ala Ala
1               5                   10                  15

Leu His Leu Leu Leu Leu Phe Ala Ala Gly Ala Glu Lys Leu Pro Gly
            20                  25                  30

Gln Gly Val His Ser Gln Gly Gln Gly Pro Gly Ala Asn Phe Val Ser
        35                  40                  45

Phe Val Gly Gln Ala Gly Gly Gly Gly Pro Ala Gly Gln Gln Leu Pro
    50                  55                  60

Gln Leu Pro Gln Ser Ser Gln Leu Gln Gln Gln Gln Gln Gln Gln Gln
65                  70                  75                  80

Gln Gln Gln Gln Pro Gln Pro Pro Gln Pro Pro Phe Pro Ala Gly Gly
                85                  90                  95

Pro Pro Ala Arg Arg Gly Gly Ala Gly Ala Gly Gly Gly Trp Lys Leu
            100                 105                 110

Ala Glu Glu Glu Ser Cys Arg Glu Asp Val Thr Arg Val Cys Pro Lys
        115                 120                 125

His Thr Trp Ser Asn Asn Leu Ala Val Leu Glu Cys Leu Gln Asp Val
    130                 135                 140

Arg Glu Pro Glu Asn Glu Ile Ser Ser Asp Cys Asn His Leu Leu Trp
145                 150                 155                 160

Asn Tyr Lys Leu Asn Leu Thr Thr Asp Pro Lys Phe Glu Ser Val Ala
                165                 170                 175

Arg Glu Val Cys Lys Ser Thr Ile Thr Glu Ile Lys Glu Cys Ala Asp
            180                 185                 190

Glu Pro Val Gly Lys Gly Tyr Met Val Ser Cys Leu Val Asp His Arg
        195                 200                 205

Gly Asn Ile Thr Glu Tyr Gln Cys His Gln Tyr Ile Thr Lys Met Thr
    210                 215                 220

Ala Ile Ile Phe Ser Asp Tyr Arg Leu Ile Cys Gly Phe Met Asp Asp
225                 230                 235                 240

Cys Lys Asn Asp Ile Asn Ile Leu Lys Cys Gly Ser Ile Arg Leu Gly
                245                 250                 255

Glu Lys Asp Ala His Ser Gln Gly Glu Val Val Ser Cys Leu Glu Lys
            260                 265                 270

Gly Leu Val Lys Glu Ala Glu Glu Arg Glu Pro Lys Ile Gln Val Ser
        275                 280                 285

Glu Leu Cys Lys Lys Ala Ile Leu Arg Val Ala Glu Leu Ser Ser Asp
    290                 295                 300

Asp Phe His Leu Asp Arg His Leu Tyr Phe Ala Cys Arg Asp Asp Arg
305                 310                 315                 320

Glu Arg Phe Cys Glu Asn Thr Gln Ala Gly Glu Gly Arg Val Tyr Lys
                325                 330                 335

Cys Leu Phe Asn His Lys Phe Glu Glu Ser Met Ser Glu Lys Cys Arg
            340                 345                 350

Glu Ala Leu Thr Thr Arg Gln Lys Leu Ile Ala Gln Asp Tyr Lys Val
        355                 360                 365

Ser Tyr Ser Leu Ala Lys Ser Cys Lys Ser Asp Leu Lys Lys Tyr Arg
    370                 375                 380

Cys Asn Val Glu Asn Leu Pro Arg Ser Arg Glu Ala Arg Leu Ser Tyr
385                 390                 395                 400

Leu Leu Met Cys Leu Glu Ser Ala Val His Arg Gly Arg Gln Val Ser
                405                 410                 415

Ser Glu Cys Gln Gly Glu Met Leu Asp Tyr Arg Arg Met Leu Met Glu
            420                 425                 430
```

```
Asp Phe Ser Leu Ser Pro Glu Ile Ile Leu Ser Cys Arg Gly Glu Ile
        435                 440                 445

Glu His His Cys Ser Gly Leu His Arg Lys Gly Arg Thr Leu His Cys
    450                 455                 460

Leu Met Lys Val Val Arg Gly Glu Lys Gly Asn Leu Gly Met Asn Cys
465                 470                 475                 480

Gln Gln Ala Leu Gln Thr Leu Ile Gln Glu Thr Asp Pro Gly Ala Asp
                485                 490                 495

Tyr Arg Ile Asp Arg Ala Leu Asn Glu Ala Cys Glu Ser Val Ile Gln
            500                 505                 510

Thr Ala Cys Lys His Ile Arg Ser Gly Asp Pro Met Ile Leu Ser Cys
        515                 520                 525

Leu Met Glu His Leu Tyr Thr Glu Lys Met Val Glu Asp Cys Glu His
    530                 535                 540

Arg Leu Leu Glu Leu Gln Tyr Phe Ile Ser Arg Asp Trp Lys Leu Asp
545                 550                 555                 560

Pro Val Leu Tyr Arg Lys Cys Gln Gly Asp Ala Ser Arg Leu Cys His
                565                 570                 575

Thr His Gly Trp Asn Glu Thr Ser Glu Phe Met Pro Gln Gly Ala Val
            580                 585                 590

Phe Ser Cys Leu Tyr Arg His Ala Tyr Arg Thr Glu Glu Gln Gly Arg
        595                 600                 605

Arg Leu Ser Arg Glu Cys Arg Ala Glu Val Gln Arg Ile Leu His Gln
    610                 615                 620

Arg Ala Met Asp Val Lys Leu Asp Pro Ala Leu Gln Asp Lys Cys Leu
625                 630                 635                 640

Ile Asp Leu Gly Lys Trp Cys Ser Glu Lys Thr Glu Thr Gly Gln Glu
                645                 650                 655

Leu Glu Cys Leu Gln Asp His Leu Asp Asp Leu Val Val Glu Cys Arg
            660                 665                 670

Asp Ile Val Gly Asn Leu Thr Glu Leu Glu Ser Glu Asp Ile Gln Ile
        675                 680                 685

Glu Ala Leu Leu Met Arg Ala Cys Glu Pro Ile Ile Gln Asn Phe Cys
    690                 695                 700

His Asp Val Ala Asp Asn Gln Ile Asp Ser Gly Asp Leu Met Glu Cys
705                 710                 715                 720

Leu Ile Gln Asn Lys His Gln Lys Asp Met Asn Glu Lys Cys Ala Ile
                725                 730                 735

Gly Val Thr His Phe Gln Leu Val Gln Met Lys Asp Phe Arg Phe Ser
            740                 745                 750

Tyr Lys Phe Lys Met Ala Cys Lys Glu Asp Val Leu Lys Leu Cys Pro
        755                 760                 765

Asn Ile Lys Lys Lys Val Asp Val Val Ile Cys Leu Ser Thr Thr Val
    770                 775                 780

Arg Asn Asp Thr Leu Gln Glu Ala Lys Glu His Arg Val Ser Leu Lys
785                 790                 795                 800

Cys Arg Arg Gln Leu Arg Val Glu Glu Leu Glu Met Thr Glu Asp Ile
                805                 810                 815

Arg Leu Glu Pro Asp Leu Tyr Glu Ala Cys Lys Ser Asp Ile Lys Asn
            820                 825                 830

Phe Cys Ser Ala Val Gln Tyr Gly Asn Ala Gln Ile Ile Glu Cys Leu
        835                 840                 845

Lys Glu Asn Lys Lys Gln Leu Ser Thr Arg Cys His Gln Lys Val Phe
```

```
    850                 855                 860

Lys Leu Gln Glu Thr Glu Met Met Asp Pro Glu Leu Asp Tyr Thr Leu
865                 870                 875                 880

Met Arg Val Cys Lys Gln Met Ile Lys Arg Phe Cys Pro Glu Ala Asp
                885                 890                 895

Ser Lys Thr Met Leu Gln Cys Leu Lys Gln Asn Lys Asn Ser Glu Leu
            900                 905                 910

Met Asp Pro Lys Cys Lys Gln Met Ile Thr Lys Arg Gln Ile Thr Gln
        915                 920                 925

Asn Thr Asp Tyr Arg Leu Asn Pro Met Leu Arg Lys Ala Cys Lys Ala
    930                 935                 940

Asp Ile Pro Lys Phe Cys His Gly Ile Leu Thr Lys Ala Lys Asp Asp
945                 950                 955                 960

Ser Glu Leu Glu Gly Gln Val Ile Ser Cys Leu Lys Leu Arg Tyr Ala
                965                 970                 975

Asp Gln Arg Leu Ser Ser Asp Cys Glu Asp Gln Ile Arg Ile Ile Ile
            980                 985                 990

Gln Glu Ser Ala Leu Asp Tyr Arg  Leu Asp Pro Gln Leu  Gln Leu His
        995                 1000                1005

Cys Ser  Asp Glu Ile Ser Ser  Leu Cys Ala Glu Glu  Ala Ala Ala
    1010                1015                1020

Gln Glu  Gln Thr Gly Gln Val  Glu Glu Cys Leu Lys  Val Asn Leu
    1025                1030                1035

Leu Lys  Ile Lys Thr Glu Leu  Cys Lys Lys Glu Val  Leu Asn Met
    1040                1045                1050

Leu Lys  Glu Ser Lys Ala Asp  Ile Phe Val Asp Pro  Val Leu His
    1055                1060                1065

Thr Ala  Cys Ala Leu Asp Ile  Lys His His Cys Ala  Ala Ile Thr
    1070                1075                1080

Pro Gly  Arg Gly Arg Gln Met  Ser Cys Leu Met Glu  Ala Leu Glu
    1085                1090                1095

Asp Lys  Arg Val Arg Leu Gln  Pro Glu Cys Lys Lys  Arg Leu Asn
    1100                1105                1110

Asp Arg  Ile Glu Met Trp Ser  Tyr Ala Ala Lys Val  Ala Pro Ala
    1115                1120                1125

Asp Gly  Phe Ser Asp Leu Ala  Met Gln Val Met Thr  Ser Pro Ser
    1130                1135                1140

Lys Asn  Tyr Ile Leu Ser Val  Ile Ser Gly Ser Ile  Cys Ile Leu
    1145                1150                1155

Phe Leu  Ile Gly Leu Met Cys  Gly Arg Ile Thr Lys  Arg Val Thr
    1160                1165                1170

Arg Glu  Leu Lys Asp Arg Leu  Gln Tyr Arg Ser Glu  Thr Met Ala
    1175                1180                1185

Tyr Lys  Gly Leu Val Trp Ser  Gln Asp Val Thr Gly  Ser Pro Ala
    1190                1195                1200


<210> SEQ ID NO 13
<211> LENGTH: 4633
<212> TYPE: DNA
<213> ORGANISM: Homo sapiens
<220> FEATURE:
<221> NAME/KEY: CDS
<222> LOCATION: (656)..(1339)

<400> SEQUENCE: 13

gccctccatt gtctccacgg cggcgaggag cgccggcgag cgcagcccgg gaccgagcgg      60
```

```
ggcggcgcgg ctggcggggc cggcggcggc tgaagcgaga gcgcgacgcg acgcgaccgc    120

ggcttcccga gctgcgcctg gccgcccagc gccgcggccc gcccgaggcc tggaggggtc    180

cgggccgccg tccatggtcg cggcgtcctg aggcggggga cgcgcccggc gcccccggcc    240

ctcctccgcc tcctcccgcg gggcgggcgg cctcctccgg cgcctccccg cgcccgcccg    300

ccgctcgccg ccgcctccct ccctccttcc ctgcggctcc cccggctttc ggagcccggg    360

ggcggcctgt ggcgcgcgga gcccgcgccg gactgcgcct ctttggacct tgaggggaaa    420

catgcgtttg ccttggatcg tttgaaattc tgagtttggg atccccgccc gcccgcctgc    480

ctcttccgcc ccgcgggttt tttcctttt tccttttgct tttttcctt ttctccctcc    540

gggtctcctt tttgactccc tccccctta tgctcgccca gccctccccc tgctgctgag    600

aagtggggga gggtctcggc ctccaggttc ccgccccacc ggggcccggg cgagc atg    658
                                                             Met
                                                             1

ggg ggc aag cag agc acg gcg gcc cgc tcc cgg ggc ccc ttc ccg ggg      706
Gly Gly Lys Gln Ser Thr Ala Ala Arg Ser Arg Gly Pro Phe Pro Gly
            5                   10                  15

gtc tcc acc gat gac agc gcc gtg ccg ccg ccg gga ggg gcg ccc cat      754
Val Ser Thr Asp Asp Ser Ala Val Pro Pro Pro Gly Gly Ala Pro His
        20                  25                  30

ttc ggg cac tac cgg acg ggc ggc ggg gcc atg ggg ctg cgc agc cgc      802
Phe Gly His Tyr Arg Thr Gly Gly Gly Ala Met Gly Leu Arg Ser Arg
    35                  40                  45

tcg gtc agc tcg gtg gca ggc atg ggc atg gac ccc agc acg gcc ggg      850
Ser Val Ser Ser Val Ala Gly Met Gly Met Asp Pro Ser Thr Ala Gly
50                  55                  60                  65

ggg gtg ccc ttt ggc ctc tac acc ccc gcc tcc cgg ggc acc ggc gac      898
Gly Val Pro Phe Gly Leu Tyr Thr Pro Ala Ser Arg Gly Thr Gly Asp
                70                  75                  80

tcc gag agg gcg ccc ggc ggc gga ggg tct gcg tcc gac tcc acc tat      946
Ser Glu Arg Ala Pro Gly Gly Gly Gly Ser Ala Ser Asp Ser Thr Tyr
            85                  90                  95

gcc cat ggc aat ggt tac cag gag acg ggc ggc ggt cac cat aga gac      994
Ala His Gly Asn Gly Tyr Gln Glu Thr Gly Gly Gly His His Arg Asp
        100                 105                 110

ggg atg ctg tac ctg ggc tcc cga gcc tcg ctg gcg gat gct cta cct     1042
Gly Met Leu Tyr Leu Gly Ser Arg Ala Ser Leu Ala Asp Ala Leu Pro
    115                 120                 125

ctg cac atc gca ccc agg tgg ttc agc tcg cat agt ggt ttc aag tgc     1090
Leu His Ile Ala Pro Arg Trp Phe Ser Ser His Ser Gly Phe Lys Cys
130                 135                 140                 145

ccc att tgc tcc aag tct gtg gct tct gac gag atg gaa atg cac ttt     1138
Pro Ile Cys Ser Lys Ser Val Ala Ser Asp Glu Met Glu Met His Phe
                150                 155                 160

ata atg tgt ttg agc aaa cct cgc ctc tcc tac aac gat gat gtg ctg     1186
Ile Met Cys Leu Ser Lys Pro Arg Leu Ser Tyr Asn Asp Asp Val Leu
            165                 170                 175

act aaa gac gcg ggt gag tgt gtg atc tgc ctg gag gag ctg ctg cag     1234
Thr Lys Asp Ala Gly Glu Cys Val Ile Cys Leu Glu Glu Leu Leu Gln
        180                 185                 190

ggg gac acg ata gcc agg ctg ccc tgc ctg tgc atc tat cac aaa agc     1282
Gly Asp Thr Ile Ala Arg Leu Pro Cys Leu Cys Ile Tyr His Lys Ser
    195                 200                 205

tgc ata gac tcg tgg ttt gaa gtg aac aga tct tgt ccg gaa cac cct     1330
Cys Ile Asp Ser Trp Phe Glu Val Asn Arg Ser Cys Pro Glu His Pro
210                 215                 220                 225

gcg gac tga cctgcgggct tgcttgctga ctcctctcaa agggacagag             1379
```

```
Ala Asp

cgcccctgct ccagggagga ggctcaccgg accctggggc agagctgagc ttgggacacc   1439
agcgggaaca gggcacccct tctgcactga cttccagatc atggttctcc cttcctccct   1499
gaggacacca aattggatga gagcaagttt gagagaagaa tgaatcaact gctatccttc   1559
ccctcacccc tcagcccagg agggaaaggg cattttcttt ttcatctttg aaaggcattg   1619
tgggtctgtc tttaaagtgt ttacaaaaaa aaattatata aaaaaaaagt ctagtgtcga   1679
ctggtgtttt ccctcgtgat gtttacagct tgctgtttgc tgcccagcca taacccactc   1739
agtgacagac gaacacagct aaggcctcgc tgccagcctt ctgacggcgg gcgagcacac   1799
ggtctcttcc cctgccccaa ctggccctct ccaccaccaa cttctctact ttgggtttgt   1859
ttggtttttt ccctctattt ttctggctgg ttttttgctc ttttctcccc ttgagaccct   1919
aatatcttga cttcattgcc aaaaaacaac ccattgagaa ctttcttcct actgatccca   1979
tctcttttcc cttctttcct cctggttccg gtcagttcag aggatttaac aatcacaagt   2039
gtcctgcaaa aatgcctgaa cattattctt aggccctcgt ggattttttt tttcagaaaa   2099
cttaaacaaa aaaagactta ctaagaaata tgtacagcta cccctgtttt caggcactat   2159
gtttgagaac attttagcca ttgatgttca cacgtggcat cagcccatgc aagataggtt   2219
tctgtattta tatattaaaa tacaaaaaaa aacttataaa atgtttaaaa aaatgttcaa   2279
agcttgggag aaaagctttc ttcattagtc aaggtgtttt gatatggtat taaaatgtct   2339
aataaaagat ggcactgcgt gattttattt taatgaagtg ttatacaatc aagaaatggg   2399
ggcaagggcc tgccccccac tccctcacct acctccttag cattccttca ggctgctact   2459
cggggctcca ggtgtgtgaa ttggtcctca gatagtcagg cctgggtgga gggagtggca   2519
agtcaggcgt gcctcctaca agcttcctaa cctcttaagc atcatggaac cagtcagccc   2579
tctgtggagt cattgtgctg gacctctgaa aagatctgca ggggccaaga tgttgcagcc   2639
accggaggct gcaaggatgt gggttcttcc aggtgtgggc ccagcccccc tccttccagc   2699
ctttgctccc catcccacgt tccactcgcc ctgcctgttg ttcagtttgc gtctcagtgc   2759
tgactcacgg gcatgcttca ttgaggccca ggaagaggcc ctggtttggg gctgtgccag   2819
ctcagagccc ttgaaccaga accaactgct caggctcaca aaagttggca aaatgcgggc   2879
tgggcaggca gctcggggca gggagcagca gtgcaggcct ggcctgtgtc cccgtgccca   2939
gcgggctccc ggagcagcat tccagagcct cctgcagagc cagcgaagga aagctctaga   2999
gggagacgac tccaccgcct ctctgctctg acccttctca ggcccgcctg atgtgctgga   3059
ccatccccct gctgccacgg cccctggctc cgcagtcacc ctccatcaga tgcttccaga   3119
agcacctact ctgtgcaagg gcattcacaa caggccagtg ggcaaacgtg agccagggcc   3179
agcggagaaa cactaaagaa gactcggtgg ttcagagcct gggtctcagc gcgggacccg   3239
tctggggtga agaccttggg gctgttgtga gtcggtggca ggaacgtggg ctctagactg   3299
tgcattcagg ctctcctact tggcagaatg atcttgggga aacgacttca tctgaacttc   3359
agatatttca catgtgaagc ggggacaaaa ccatgcagct cagaggtccc tgtgggggct   3419
gggggagctg ccctgcaggt cttggcacat gcacagcagg ctccccatag ctttgtcacc   3479
acaaagggca ctgttctatt cacagcacct cctgcttctg cctggcaact gtgtctccct   3539
gtgctatatt taattccacc agcaaagctg gcgaggcagg gcccagccct gaaggagatc   3599
tccttgcctg acccctggac ctggaaatgg aggcttcatg tgcccgcctt ggcggcttaa   3659
gcctgctgct ttggcagtgc catgggtgag ccgagcagct gtgaggtggg tggggcaggg   3719
```

```
ctgtagccca cgccgggtgc tattccaggc tctaggggct ggtgctcatc cccaccccca   3779

gcgacttccg tcctacctgg catgctgcag ccctctgccg gctgtggtgt cctctgaatt   3839

tggacccagg ttgcctgctc ttgttgtggg ggtgggattg ggctgtctg tgtttcccag   3899

gtggagctca tgtttgtgat cctctatctg gacagctctc cagaatcctg tgttgcccct   3959

gttctgcctt tctgggatgg gagagaaggt gagggagccg gcgagcaggt tctaccctct   4019

ctgctaaggg cctagcacac tttgatgagg ttcctggacg tgagaccctc acaaagacca   4079

accattcctc taatagccat ttaacggtac tgcagttcat gggaaaatgt cctcattctt   4139

aggagataga tgctggatta tataggtgaa tgccttcaag aaatgtgtaa tttaattcca   4199

aatagttccc cccaaaatac acaaagcaaa taaggccaaa atgttcattg ttgaatctgc   4259

agtggctggt atttcagtga acagtgtact tgttctttca acttttctgt atgtttggaa   4319

tttttcttaa taaaagattg tgggaaatgg tcatttgctg agcgcctcct agttgccagg   4379

cactggaggg cgcatcaaag aagagtccta cccaggaggg agagcgcagc tgctgcagga   4439

ttctcgcctg gaagagtggg tggctggctg gctggctgga aggggagggg cgagagggct   4499

gtctcggtga tgagcacacg cgtgctgggg tggtttgggg agagggctga gatttgtcac   4559

cagtgagccc ttggcacggt ctctgctccc caccagggca gcacgggaca gaaacgtcac   4619

ggaggagtag cctc                                                     4633
```

<210> SEQ ID NO 14
<211> LENGTH: 227
<212> TYPE: PRT
<213> ORGANISM: Homo sapiens

<400> SEQUENCE: 14

```
Met Gly Gly Lys Gln Ser Thr Ala Ala Arg Ser Arg Gly Pro Phe Pro
1               5                   10                  15

Gly Val Ser Thr Asp Asp Ser Ala Val Pro Pro Pro Gly Gly Ala Pro
            20                  25                  30

His Phe Gly His Tyr Arg Thr Gly Gly Gly Ala Met Gly Leu Arg Ser
        35                  40                  45

Arg Ser Val Ser Ser Val Ala Gly Met Gly Met Asp Pro Ser Thr Ala
    50                  55                  60

Gly Gly Val Pro Phe Gly Leu Tyr Thr Pro Ala Ser Arg Gly Thr Gly
65                  70                  75                  80

Asp Ser Glu Arg Ala Pro Gly Gly Gly Gly Ser Ala Ser Asp Ser Thr
                85                  90                  95

Tyr Ala His Gly Asn Gly Tyr Gln Glu Thr Gly Gly Gly His His Arg
            100                 105                 110

Asp Gly Met Leu Tyr Leu Gly Ser Arg Ala Ser Leu Ala Asp Ala Leu
        115                 120                 125

Pro Leu His Ile Ala Pro Arg Trp Phe Ser Ser His Ser Gly Phe Lys
    130                 135                 140

Cys Pro Ile Cys Ser Lys Ser Val Ala Ser Asp Glu Met Glu Met His
145                 150                 155                 160

Phe Ile Met Cys Leu Ser Lys Pro Arg Leu Ser Tyr Asn Asp Asp Val
                165                 170                 175

Leu Thr Lys Asp Ala Gly Glu Cys Val Ile Cys Leu Glu Glu Leu Leu
            180                 185                 190

Gln Gly Asp Thr Ile Ala Arg Leu Pro Cys Leu Cys Ile Tyr His Lys
        195                 200                 205

Ser Cys Ile Asp Ser Trp Phe Glu Val Asn Arg Ser Cys Pro Glu His
```

```
    210                 215                 220

Pro Ala Asp
225


<210> SEQ ID NO 15
<211> LENGTH: 2907
<212> TYPE: DNA
<213> ORGANISM: Homo sapiens
<220> FEATURE:
<221> NAME/KEY: CDS
<222> LOCATION: (78)..(542)

<400> SEQUENCE: 15

gctccaggaa gtgcgggggc tccagccgcc cggccggccg cgatgcattc tggggaagga      60

gcagcaccaa atccaag atg gcg gcc agc agg agg ctg atg aag gag ctt        110
                   Met Ala Ala Ser Arg Arg Leu Met Lys Glu Leu
                   1               5                   10

gaa gaa atc cgc aaa tgt ggg atg aaa aac ttc cgt aac atc cag gtt       158
Glu Glu Ile Arg Lys Cys Gly Met Lys Asn Phe Arg Asn Ile Gln Val
            15                  20                  25

gat gaa gct aat tta ttg act tgg caa ggg ctt att gtt cct gac aac       206
Asp Glu Ala Asn Leu Leu Thr Trp Gln Gly Leu Ile Val Pro Asp Asn
        30                  35                  40

cct cca tat gat aag gga gcc ttc aga atc gaa atc aac ttt cca gca       254
Pro Pro Tyr Asp Lys Gly Ala Phe Arg Ile Glu Ile Asn Phe Pro Ala
    45                  50                  55

gag tac cca ttc aaa cca ccg aag atc aca ttt aaa aca aag atc tat       302
Glu Tyr Pro Phe Lys Pro Pro Lys Ile Thr Phe Lys Thr Lys Ile Tyr
60                  65                  70                  75

cac cca aac atc gac gaa aag ggg cag gtc tgt ctg cca gta att agt       350
His Pro Asn Ile Asp Glu Lys Gly Gln Val Cys Leu Pro Val Ile Ser
                80                  85                  90

gcc gaa aac tgg aag cca gca acc aaa acc gac caa gta atc cag tcc       398
Ala Glu Asn Trp Lys Pro Ala Thr Lys Thr Asp Gln Val Ile Gln Ser
            95                  100                 105

ctc ata gca ctg gtg aat gac ccc cag cct gag cac ccg ctt cgg gct       446
Leu Ile Ala Leu Val Asn Asp Pro Gln Pro Glu His Pro Leu Arg Ala
        110                 115                 120

gac cta gct gaa gaa tac tct aag gac cgt aaa aaa ttc tgt aag aat       494
Asp Leu Ala Glu Glu Tyr Ser Lys Asp Arg Lys Lys Phe Cys Lys Asn
    125                 130                 135

gct gaa gag ttt aca aag aaa tat ggg gaa aag cga cct gtg gac taa       542
Ala Glu Glu Phe Thr Lys Lys Tyr Gly Glu Lys Arg Pro Val Asp
140                 145                 150

aatctgccac gattggttcc agcaagtgtg agcagagacc ccgtgcagtg cattcagaca     602

ccccgcaaag caggactctg tggaaattga cacgtgccac cgcctggcgt tcgcttgtgg     662

cagttactaa ctttctacag ttttcttaat caaaagtggt ctaggtaacc tgtaaagaaa     722

ggattaaaaa tttaagatgt tctagttctg ctctctttgt tttaaaaatc actgcttcaa     782

tctacttcaa aagaatggtg tttcttttct tgtccaattt tatccaaaat cttcaagtta     842

catttaaccc ataaggttta aaaaaaagga aaaaaaacgg ttgtggttcc ctttcttccc     902

taccettgcc actcccactt tctggcaccg agtttatttt tcacttactt acttccccag     962

accccgggct cgcctccaca aaggagaaga gactgccctg gcggtcctgg tggcttttct    1022

tagcatgtgt ggcactgttg cccagtgtgg gagttggttt aaattctcct gactccagtt    1082

tataacatcc ttttaaaaaa tttaaaaaca aacagccaca cccctcctcc agtccttctc    1142

ctcagttctt gtgtgaaact ccagctgatg ttaccacagt aacatcagtt aattgggcaa    1202
```

```
gccctgatgt cagtgtgtgt aactgacctc tggcctggcc tgcacagaga agccctataa   1262

tcacaggtct gtggtggccc cgaaatgggg ggcctgctag tcaggaggat gctgtgcaca   1322

ctgtgtgtga tgaatctcgc cagaaaggct cctgaggtcc caggttggca cttctccctg   1382

cagccattgt agaagatctg ctggtccttg caggcaaagc tacagccaga atgtccgttt   1442

gaaactccta gctcatctgt caccgagctt catccgaatg tgccacggag cttgctctcc   1502

acttcctccg tgcagtggcc ctgccacagc cctccctcgg cacactttga ccctttgtag   1562

gattggaatt agcaggactc ggctatttaa agcaccagtc tggggtcgcc tgggcccctg   1622

ctgacccct cctccagagc agccagccca gcccgggaac aagacggact tcctctccct    1682

tcggactcac agcctttgca gagtcaagct ccacttgaag ctcactcagt aatatccttt   1742

caatgtgttt tatattgttt tgactgcctt tttttgtaga aataaaaatt gaccttagaa   1802

tttatcgtca gataaacttg taaagatttg aatattaatg tcttttcaag gcaaatggga   1862

ttgtccccgc actagtagag aatccatgtc gctctgacac cccaaggaag ccgacgatcc   1922

aaatgccgtg tgtcaccaac cccgcttctg ccactggcgg cttcccttct tggctcttgg   1982

gggggactag atcctgtgga gaagatgact taaactttgc tttttgtttt aattttaatt   2042

ctataacttg agatctttcc ggggcctaca ggcgtgtaag acagcttggt ctggtctgtg   2102

cagaagtggg gagtgatggg caggttcggc agcctaacat tgttcaggcg catggcccct   2162

gcggtgtgta cacgaactcg gcttcttttg tcctaggtac gccaagggca ggtttctgga   2222

gactcccttg tgcccgggat ggcaagggca ccgggctggc gtttccacat ctgtcttcat   2282

tagcagaaaa gtgatgatgg attttatttc actcacactc cagtttgtaa taaaatgcca   2342

aattctgtca gctatccaaa caagccacca tttgttcttg ttgcttctct ggatccagaa   2402

atgttgccat tcttggaaac tgtcccattg cttcgtattt ctgccaacgt agctctgcct   2462

gcctgtcaac ccctcactgc actctgctca tcacgggagg atacctgtgt gccggcagcc   2522

cctcagggac tctcagccct ggcactggca ccccagggtt ggccccgtca gcagaggctt   2582

ggctttcgag ccagtgggtg tctctccttt gggcctgggc ggcttgctcc tgccagccat   2642

gccttcaggg taggctctga gcaagctggc gaacagccct ggctgctcca aaaccaaaaa   2702

gctgggtcct ctggaggagg ggcgagctgt ggagcagcca cccactgctg ccccaagctc   2762

actcaggaat tcacacccgc ctggtttctt gaagtgtgct gggtccttcc ctctgctccc   2822

tactccccac cacggcagag aataggcttt ctaagatgct gcgatcccgt tctgctgccc   2882

gtaataaaaa tgctctcaga cactg                                         2907
```

<210> SEQ ID NO 16
<211> LENGTH: 154
<212> TYPE: PRT
<213> ORGANISM: Homo sapiens

<400> SEQUENCE: 16

```
Met Ala Ala Ser Arg Arg Leu Met Lys Glu Leu Glu Glu Ile Arg Lys
1               5                   10                  15

Cys Gly Met Lys Asn Phe Arg Asn Ile Gln Val Asp Glu Ala Asn Leu
            20                  25                  30

Leu Thr Trp Gln Gly Leu Ile Val Pro Asp Asn Pro Pro Tyr Asp Lys
        35                  40                  45

Gly Ala Phe Arg Ile Glu Ile Asn Phe Pro Ala Glu Tyr Pro Phe Lys
    50                  55                  60

Pro Pro Lys Ile Thr Phe Lys Thr Lys Ile Tyr His Pro Asn Ile Asp
65                  70                  75                  80
```

-continued

```
Glu Lys Gly Gln Val Cys Leu Pro Val Ile Ser Ala Glu Asn Trp Lys
                85                  90                  95

Pro Ala Thr Lys Thr Asp Gln Val Ile Gln Ser Leu Ile Ala Leu Val
            100                 105                 110

Asn Asp Pro Gln Pro Glu His Pro Leu Arg Ala Asp Leu Ala Glu Glu
        115                 120                 125

Tyr Ser Lys Asp Arg Lys Lys Phe Cys Lys Asn Ala Glu Glu Phe Thr
    130                 135                 140

Lys Lys Tyr Gly Glu Lys Arg Pro Val Asp
145                 150
```